United States Patent
Kaluza et al.

(10) Patent No.: US 9,670,274 B2
(45) Date of Patent: Jun. 6, 2017

(54) ANTI-ALPHA-SYNUCLEIN ANTIBODIES AND METHODS OF USE

(71) Applicant: Hoffmann-La Roche Inc., Little Falls, NJ (US)

(72) Inventors: Klaus Kaluza, Weilheim (DE); Olaf Mundigl, Weilheim (DE); Thomas Kremer, Grenzach-Wyhlen (DE); Markus Britschgi, Allschwil (CH); Sylwia Huber, Rheinfelden (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/284,464

(22) Filed: Oct. 3, 2016

(65) Prior Publication Data
US 2017/0114123 A1    Apr. 27, 2017

Related U.S. Application Data

(63) Continuation of application No. 14/549,102, filed on Nov. 20, 2014, now Pat. No. 9,493,553.

(30) Foreign Application Priority Data

Nov. 21, 2013    (EP) .................................... 13193892

(51) Int. Cl.
C07K 16/18    (2006.01)
C07K 16/28    (2006.01)
A61K 39/00    (2006.01)

(52) U.S. Cl.
CPC .............. *C07K 16/18* (2013.01); *C07K 16/28* (2013.01); *C07K 16/2881* (2013.01); *A61K 2039/505* (2013.01); *C07K 2317/24* (2013.01); *C07K 2317/32* (2013.01); *C07K 2317/33* (2013.01); *C07K 2317/34* (2013.01); *C07K 2317/51* (2013.01); *C07K 2317/515* (2013.01); *C07K 2317/622* (2013.01); *C07K 2317/76* (2013.01); *C07K 2317/94* (2013.01); *C07K 2319/02* (2013.01); *C07K 2319/33* (2013.01)

(58) Field of Classification Search
None
See application file for complete search history.

(56) References Cited

FOREIGN PATENT DOCUMENTS

| WO | 2007011907 A2 | 1/2007 |
|---|---|---|
| WO | 2007012061 A2 | 1/2007 |
| WO | 2007021255 A1 | 2/2007 |
| WO | 2010069603 A1 | 6/2010 |
| WO | 2011020133 A1 | 2/2011 |
| WO | 2011104696 A1 | 9/2011 |
| WO | 2014033074 A1 | 3/2014 |

OTHER PUBLICATIONS

Bae et al., "Antibody-aided clearance of extracellular α-synuclein prevents cell-to-cell aggregate transmission," J. Neurosci. 32(39):13454-13469 (2012).

(Continued)

*Primary Examiner* — Adam M Weidner
(74) *Attorney, Agent, or Firm* — Jones Day

(57) ABSTRACT

The invention provides anti-human alpha-synuclein antibodies and methods of using the same.

8 Claims, 16 Drawing Sheets

(56) References Cited

OTHER PUBLICATIONS

Barkhordarian et al., "Isolating recombinant antibodies against specific protein morphologies using atomic force microscopy and phage display technologies," Protein Eng. Des. Sel. 19(11):497-502 (2006) (Epub Sep. 19, 2006).

Bartels et al., "N-alpha-acetylation of α-synuclein increases its helical folding propensity, GM1 binding specificity and resistance to aggregation," PLoS One 9(7):e103727 (2014).

Covance: "alpha-synuclein (Syn303) Monoclonal Antibody, Purified," Retrieved from the Internet: <URL:http://www.funakoshi.co.jp/data/datasheet/BAB/MMS-5085.pdf> [retrieved on Feb. 11, 2015] (2 pages).

Duda et al., "Novel antibodies to synuclein show abundant striatal pathology in Lewy body diseases," Ann. Neurol. 52(2):205-210 (2002).

El-Agnaf et al., "A strategy for designing inhibitors of α-synuclein aggregation and toxicity as a novel treatment for Parkinson's disease and related disorders," FASEB J. 18(11):1315-1317 (2004) (Epub Jun. 4, 2004).

Emadi et al., "Detecting morphologically distinct oligomeric forms of α-synuclein," J. Biol. Chem. 284(17):11048-11058 (2009) (Epub Jan. 13, 2009).

Emadi et al., "Inhibiting aggregation of α-synuclein with human single chain antibody fragments," Biochemistry 43(10):2871-2878 (2004).

Emadi et al., "Isolation of a human single chain antibody fragment against oligomeric alpha-synuclein that inhibits aggregation and prevents alpha-synuclein-induced toxicity," J. Mol. Biol. 368(4):1132-1144 (2007) (Epub Mar. 7, 2007).

Joshi et al., "Fusion to a highly charged proteasomal retargeting sequence increases soluble cytoplasmic expression and efficacy of diverse anti-synuclein intrabodies," mAbs 4(6):686-693 (2012) (Epub Aug. 28, 2012).

Kellie et al., "Quantitative measurement of intact alpha-synuclein proteoforms from post-mortem control and Parkinson's disease brain tissue by intact protein mass spectrometry," Sci. Rep. 4:5797 (2014).

Kussie "A Signel Engineered Amino Acid Subsitution Changes Antibody Fine Specificity" J Immunology, 146-152 (1994).

Kvam et al., 2009, "Conformational targeting of fibrillar polyglutamine proteins in live cells escalates aggregation and cytotoxicity," PLoS One 4(5): e5727.

Ladiwala et al., 2012, "Rational design of potent domain antibody inhibitors of amyloid fibril assembly," PNAS 110(4): 19965-19970.

Lynch et al., "An scFv intrabody against the nonamyloid component of alpha-synuclein reduces intracellular aggregation and toxicity," J. Mol. Biol. 377(1):136-147 (2008) (Epub Dec. 5, 2007).

Masliah et al., "Effects of α-synuclein immunization in a mouse model of Parkinson's disease," Neuron. 46(6):857-868 (2005).

Masliah et al., "Passive immunization reduces behavioral and neuropathological deficits in an alpha-synuclein transgenic model of Lewy body disease," PLoS One 6(4):e19338 (2011).

Näsström et al., "Antibodies against alpha-synuclein reduce oligomerization in living cells," PLoS One. 6(10): e27230 (2011) (Epub Oct. 31, 2011).

O'Nuallain et al., 2002, "Conformational Abs recognizing a generic amyloid fibril epitope," PNAS 99(3): 1485-1490.

Paul "Fundamental Immunology—Chapter 7—Antigen-Antibody Interations and Monoclonal Antibodies" 7th Edition, 199 (2013).

Perrin et al., "Epitope mapping and specificity of the anti-alpha-synuclein monoclonal antibody Syn-1 in mouse brain and cultured cell lines," Neurosci. Lett. 349(2):133-135 (2003).

Santa Cruz Biotechnology, Inc.: "Nitrated alpha-synuclein (Syn514): sc-32279." Retrieved from the Internet: <URL:http://datasheets.scbt.com/sc-32279.pdf> [retrieved on Feb. 11, 2015].

Sekigawa et al., "Distinct mechanisms of axonal globule formation in mice expressing human wild type α-synuclein or dementia with Lewy bodies-linked P123H β-synuclein," Mol. Brain 5:34 (2012).

Smith et al., "Effects of intravenous immunoglobulin on alpha synuclein aggregation and neurotoxicity," Int. Immunopharmacol. Dec. 2012;14(4):550-557 (2012) (Epub Sep. 29, 2012).

Soper et al., "α-synuclein-induced aggregation of cytoplasmic vesicles in *Saccharomyces cerevisiae*," Mol. Biol. Cell. 19(3):1093-1103 (2008) (Epub Jan. 2, 2008).

Tran et al., "A-synuclein immunotherapy blocks uptake and templated propagation of misfolded α-synuclein and neurodegeneration," Cell. Rep. 7(6):2054-2065 (2014) (Epub Jun. 12, 2014).

Vekrelis and Stefanis, "Targeting intracellular and extracellular alpha-synuclein as a therapeutic strategy in Parkinson's disease and other synucleinopathies," Expert Opin. Ther. Targets. 16(4):421-432 (2012).

Wagner et al., "Anle138b: a novel oligomer modulator for disease-modifying therapy of neurodegenerative diseases such as prion and Parkinson's disease," Acta Neuropathol. 125(6):795-813 (2013) (Epub Apr. 19, 2013).

Waxman and Giasson, "Characterization of antibodies that selectively detect alpha-synuclein in pathological inclusions," Acta Neuropathol. 116(1):37-46 (2008) (Epub Apr. 15, 2008).

Yu and Watts, "Developing Therapeutic Antibodies for Neurodegenerative Disease," Neurotherapeutics 10:459-472 (2013).

Zhou et al., "A human single-chain Fv intrabody blocks aberrant cellular effects of overexpressed alpha-synuclein," Mol Ther. 10(6):1023-1031 (2004).

ANTI-ALPHA-SYNUCLEIN ANTIBODIES AND METHODS OF USE

This application is a continuation of U.S. application Ser. No. 14/549,102, filed on Nov. 20, 2014, which claims the benefit of priority of European Patent Application No. 13193892.0, filed Nov. 21, 2013, the disclosures of each of which are incorporated by reference herein in their entireties.

This application incorporates by reference the Computer Readable Form (CRF) of a Sequence Listing in ASCII text format submitted via EFS-Web.

FIELD OF THE INVENTION

The present invention relates to anti-human alpha-synuclein antibodies and methods of using the same.

BACKGROUND

Parkinson's disease is characterized by a progressive loss of dopamine (DA) neurons of the nigrostriatal system and by the presence of Lewy bodies (LB) and neurites (LN), proteinaceous intraneuronal inclusions mainly composed of filamentous alpha-synuclein aggregates. Alpha-synuclein is a protein which in the brain plays a central role in the control of dopaminergic neuronal functions and which is thought to be critically implicated in PD pathophysiology. Indeed, besides the fact that alpha-synuclein is the main protein component of LB, genetic studies showed that certain point mutations in and multiplications of the alpha-synuclein gene cause familial forms of PD. A large body of evidence indicates that alpha-synuclein pathology at dopaminergic synapses may underlie the onset of neuronal cell dysfunction and degeneration in the PD brain (Bellucci, A., et al., Brain Res. 1432 (2012) 95-113).

Lewy bodies, which are deposits of alpha-synuclein, are the pathological sign of Parkinson's Disease (PD) (Goedert, M., Nat. Rev. Neurosci 2 (2001) 492-501). The staging of brain pathology related to sporadic PD is reported by Braak et al. (Neurobiology of aging 24 (2003) 197-211).

Alpha-synuclein fibrillar aggregates are the main component of Lewy bodies and Lewy neurites. Recent scientific work suggests that prefibrillar oligomers of alpha-synuclein may be key contributors in the progression of Parkinson's disease (Luk, K. C., et al., Science 338 (2012) 949-953; Auluck, P. K., et al., Science 295 (2002) 865-868; Bodner, R. A., et al., Proc. Natl. Acad. Sci. USA 103 (2006) 4246-4251; Bucciantini, M., et al., J. Biol. Chem. 279 (2004) 31374-31382; El-Agnaf, O. M., et al., FASEB J. 20 (2006) 419-425; Kayed, R., et al., Science 300 (2003) 486-489; Lashuel, H. A., et al., J. Mol. Biol. 322 (2002) 1089-1102; Masliah, E., et al., Science 287 (2000) 1265-1269.).

Chai, Y.-J., et al., report that the secreted oligomeric form of α-synuclein affects multiple steps of membrane trafficking (FEBS Lett. 587 (2013) 452-459). Exosomes of BV-2 cells induced by alpha-synuclein: important mediator of neurodegeneration in PD is reported by Chang, C., et al., Neurosci. Lett. 548 (2013) 190-195). Feng, R. L., et al. report that alpha-synuclein mediates alterations in membrane conductance: a potential role for alpha-synuclein oligomers in cell vulnerability (Eur. J. Neurosci. 32 (2010) 10-17). Lee, H-J., et al. report that autophagic failure promotes the exocytosis and intercellular transfer of alpha-synuclein (Exp. Mol. Med. 45 (2013) e22). The synaptic pathology of alpha-synuclein aggregation in dementia with Lewy bodies, Parkinson's Disease and Parkinson's Disease Dementia is reported by Schulz-Schaeffer, W. J. (Acta Neuropathol. 120 (2010) 131-143).

The vast majority of alpha-synuclein in human brain is N-terminally acetylated (Kellie, J. F., et al., Sci. Rep. 4 (2014) 5797) and this N-terminal acetylation inhibits alpha-synuclein from aggregation (Bartels, T., et al., PLoS One 9 (2014) e103727).

Different oligomeric forms of recombinant alpha-synuclein have been reported: type A oligomers (cytotoxic, effect on $Ca^{2+}$ influx), type C oligomers (aggregate seeding species), fibrils mixed with lipids (seed the aggregation of intracellular aggregates), triple proline (TP) mutant A30P/A56P/A76P (forms predominantly toxic oligomers) (see e.g. Danzer, K. M., et al., J. Neurosci. 27 (2007) 9220-9232; Danzer, K. M., et al. J. Neurochem. 111 (2009) 192-203; Luk, C. K., et al. Proc. Natl. Acad. Sci. USA 106 (2009) 20051-20056; Desplates, P., et al. Proc. Natl. Acad. Sci. USA 106 (2009) 13010-13015; Karpinar, D. P., et al., EMBO J. 28 (2009) 3256-3268; Lee, H-J., et al., J. Biol. Chem. 285 (2010) 9262-9272; Hansen, C., et al., J. Clin. Invest. 121 (2011) 715-725).

Pathological alpha-synuclein transmission initiates Parkinson-like neurodegeneration in non-transgenic mice is reported by Luk, K. C., et al. (Science 338 (2012) 949-953). The seeding induced by alpha-synuclein oligomers provides evidence for spreading of alpha-synuclein pathology and the exosomal cell-to-cell transmission of alpha synuclein oligomers is reported by Danzer, K. M., et al. (J. Neurochem. 111 (2009) 192-203; Mol. Neurodegen. 7 (2012) 42). Braidy et al. report alpha-synuclein transmission and mitochondrial toxicity in primary human foetal enteric neurons in vitro (Neurotox. Res. (2013) epub on Oct. 5, 2013). Desplats, P., et al. report inclusion formation and neuronal cell death through neuron-to-neuron transmission of alpha-synuclein (Proc. Natl. Acad. Sci. USA 106 (2009) 13010-13015). Direct transfer of alpha-synuclein from neuron to astroglia causes inflammatory responses in synucleinopathies is reported by Lee et al. (J. Biol. Chem. 285 (2010) 9262-9272). Lee, S.-J., et al. report the cell-to-cell transmission of alpha-synuclein aggregates (Meth. Mol. Biol. 849 (2012) 347-359; Nat. Rev. Neurol. 6 (2010) 702-706). The probably strongest evidence of a progression of alpha-synuclein pathology by a possible transmission of an alpha-synuclein aggregation seed comes from postmortem analysis of brains of certain PD patients who presented with Lewy pathology in fetal neurons which were grafted to their brain 11-16 years earlier (Li, J-Y., et al., Nat. Med. 14 (2008) 501-503).

Aggregated alpha-synuclein mediates dopaminergic neurotoxicity in vivo (Periquet, M., et al., J. Neurosci. 27 (2007) 3338-3346). Pieri, L., et al. report that fibrillar alpha-synuclein and huntingtin exon 1 assemblies are toxic to the cells (Biophys. J. 102 (2012) 2894-2905). Van Rooijen et al. report that membrane permeabilization by oligomeric alpha-synuclein: in search of the mechanism (PLoS One 5 (2010) e14292).

Very recently, Wagner et al. demonstrated in cellular assays and in an alpha-synuclein transgenic mouse model that the small molecule Anle138b acts as a protective alpha-synuclein oligomer modulator which may be useful for disease-modifying therapy of Parkinson's disease (Wagner, J, et al., Acta Neuropathol. 125 (2013) 795-813). Lynch, S. M., et al. report that a scFv intrabody against the non-amyloid component of alpha-synuclein reduces intracellular aggregation and toxicity (J. Mol. Biol. 377 (2008) 136-147). A strategy for designing inhibitors of alpha-synuclein aggregation and toxicity as a novel treatment for Parkinson's Disease and related disorders is reported by El-Agnaf, O. M., et al. (FASEB J. (2004)). Emadi, S., et al. report inhibiting aggregation of alpha-synuclein with human single chain antibody fragments and the isolation of a human single chain antibody fragment against oligomeric alpha-synuclein that inhibits aggregation and prevents alpha-synuclein-induced toxicity (Biochem. 43 (2004) 2871-2878; J. Mol. Biol. 368 (2007) 1132-1144). Smith et al. report effects of intravenous immunoglobulin on alpha-synuclein aggregation and neurotoxicity (Int. Immunopharmacol. 14 (2012) 550-557). Targeting intracellular and extracellular alpha-synuclein as a therapeutic strategy in Parkinson's Disease and other synucleinopathies is reported by Vekrelis, K. and Stefanis, L. (Expert. Opin. Ther. Targets 16 (2012) 421-432).

Antibody-aided clearance of cerebral synucleinopathy in respective transgenic mice was demonstrated in an active (Masliah, E., et al., Neuron 46 (2005) 857-868) and a passive (Masliah, E., et al., PLoS One 6 (2011) e19338) immunization paradigm. Binding of extracellular alpha-synuclein by specific antibodies prevents cell-to-cell aggregate transmission was reported by Bae, E-J., et al. (J. Neurosci. 32 (2012) 13454-13469).

The use of mimotopes of alpha-synuclein epitopes for treating Lewy body diseases is reported in WO 2011/020133. In WO 2007/011907 alpha-synuclein antibodies and methods related thereto are reported. Fusion to a highly charged proteasomal retargeting sequence increases soluble cytoplasmic expression and efficacy of diverse anti-synuclein intrabodies is reported by Joshi et al. (MABS 4 (2012) 686-693). Emadi et al. (J. Mol. Biol. 368 (2007) 1132-1144) report the isolation of a human single chain antibody fragment against oligomeric alpha-synuclein that inhibits aggregation and prevents alpha-synuclein-induced toxicity. The detection of morphologically distinct oligomeric forms of alpha-synuclein is reported by Emadi et al. (J. Biol. Chem. 284 (2009) 11048-11058). Zhou et al. (Mol. Ther. 10 (2004) 1023-1031) report that a human single-chain Fv intrabody blocks aberrant cellular effects of overexpressed alpha-synuclein. That antibodies against alpha-synuclein reduce oligomerization in living cells is reported by Nasstrom et al. (PLoS One 6 (2011) e27230). Protofibril-binding antibodies and their use in therapeutic and diagnostic methods for Parkinson's Disease, dementia with Lewy bodies and other alpha-synucleinopathies are reported in WO 2011/104696. Isolating recombinant antibodies against specific protein morphologies using atomic force microscopy and phage display technologies is reported by Barkhordarian et al. (Prot. Eng. Des. Select. 19 (2006) 497-502). Kvam et al. (PLoS One 4 (2009) e5727) report that conformational targeting of fibrillar polyglutamine proteins in live cells escalates aggregation and cytotoxicity.

SUMMARY

The invention provides anti-human alpha-synuclein antibodies and methods of using the same.

One aspect as reported herein is an antibody that specifically binds to human alpha-synuclein wherein the human alpha-synuclein has a free N-terminal methionine residue.

The term "free N-terminal methionine residue" denotes a methionine residue in a polypeptide that is located at the N-terminus of the polypeptide and that is not modified except for the amide-bond with which it is conjugated to the remainder of the polypeptide. Such a free N-terminal methionine residue is in one embodiment an un-modified methionine residue. Such a free N-terminal methionine residue has in one embodiment a free amino group. Human alpha-synuclein has the amino acid sequence of SEQ ID NO: 40.

In one embodiment the antibody specifically binds to human and mouse alpha-synuclein wherein the human and mouse alpha-synuclein have a free N-terminal methionine residue.

In one embodiment the alpha-synuclein is monomeric alpha-synuclein.

In one embodiment the alpha-synuclein is monomeric and oligomeric alpha-synuclein.

In one embodiment the antibody binds to the same epitope or an overlapping epitope as an antibody comprising in the heavy chain the HVRs of SEQ ID NO: 15 to 17 and in the light chain the HVRs of SEQ ID NO: 18 to 20.

In one embodiment the antibody binds to the same epitope or an overlapping epitope as an antibody comprising in the heavy chain the HVRs of SEQ ID NO: 21, 22 and 17 and in the light chain the HVRs of SEQ ID NO: 23 to 25.

In one embodiment the antibody binds to the same epitope or an overlapping epitope as an antibody comprising a heavy chain variable domain of SEQ ID NO: 26 and a light chain variable domain of SEQ ID NO: 27.

In one embodiment the antibody comprises in the heavy chain the HVRs of SEQ ID NO: 15 to 17 and in the light chain the HVRs of SEQ ID NO: 18 to 20.

In one embodiment the antibody comprises in the heavy chain the HVRs of SEQ ID NO: 21, 22 and 17 and in the light chain the HVRs of SEQ ID NO: 23 to 25.

In one embodiment the antibody has been obtained by humanizing an antibody comprising a heavy chain variable domain of SEQ ID NO: 26 and a light chain variable domain of SEQ ID NO: 27.

In one embodiment the antibody is a humanized antibody and comprises in the heavy chain variable domain the HVRs of SEQ ID NO: 15 to 17 and in the light chain variable domain the HVRs of SEQ ID NO: 18 to 20, wherein in each HVR 0 to 3 amino acid residues have been changed.

In one embodiment the antibody is a humanized antibody and comprises in the heavy chain variable domain the HVRs of SEQ ID NO: 21, 22 and 17 and in the light chain variable domain the HVRs of SEQ ID NO: 23 to 25, wherein in each HVR 0 to 3 amino acid residues have been changed.

In one embodiment the antibody is a humanized antibody and the heavy chain variable domain is derived from a heavy chain variable domain of SEQ ID NO: 26 and the light chain variable domain is derived from a light chain variable domain of SEQ ID NO: 27.

One aspect as reported herein is an antibody that binds to the same epitope or an overlapping epitope as an antibody comprising in the heavy chain the HVRs of SEQ ID NO: 15 to 17 and in the light chain the HVRs of SEQ ID NO: 18 to 20.

One aspect as reported herein is an antibody that binds to the same or an overlapping epitope as an antibody comprising a heavy chain variable domain of SEQ ID NO: 26 and a light chain variable domain of SEQ ID NO: 27.

One aspect as reported herein is an antibody comprising in the heavy chain the HVRs of SEQ ID NO: 15 to 17 and in the light chain the HVRs of SEQ ID NO: 18 to 20.

One aspect as reported herein is an antibody comprising in the heavy chain the HVRs of SEQ ID NO: 21, 22 and 17 and in the light chain the HVRs of SEQ ID NO: 23 to 25.

One aspect as reported herein is a variant antibody that has been obtained from an antibody comprising a heavy chain variable domain of SEQ ID NO: 26 and a light chain variable domain of SEQ ID NO: 27.

In one embodiment the variant antibody is a humanized antibody that has been obtained by humanizing an antibody comprising a heavy chain variable domain of SEQ ID NO: 26 and a light chain variable domain of SEQ ID NO: 27.

One aspect as reported herein is a humanized antibody comprising in the heavy chain variable domain the HVRs of SEQ ID NO: 15 to 17 and in the light chain variable domain the HVRs of SEQ ID NO: 18 to 20, wherein in each HVR 0 to 3 amino acid residues have been changed.

One aspect as reported herein is a humanized antibody comprising in the heavy chain variable domain the HVRs of SEQ ID NO: 21, 22 and 17 and in the light chain variable domain the HVRs of SEQ ID NO: 23 to 25, wherein in each HVR 0 to 3 amino acid residues have been changed.

One aspect as reported herein is a humanized antibody wherein the heavy chain variable domain is derived from a heavy chain variable domain of SEQ ID NO: 26 and the light chain variable domain is derived from a light chain variable domain of SEQ ID NO: 27.

In one embodiment of all previous aspects the antibody is conjugated to a blood-brain-barrier shuttle module.

In one embodiment the blood-brain-barrier shuttle module is an antibody or antibody fragment that specifically binds to LRP1, LRP8, human transferrin receptor or human insulin-like growth factor receptor.

In one embodiment of all previous aspects the antibody is a monoclonal antibody.

In one embodiment of all previous aspects the antibody is a humanized antibody or a chimeric antibody.

In one embodiment of all previous aspects the antibody is
a) a full length antibody of the human subclass IgG1, or
b) a full length antibody of the human subclass IgG4, or
c) a full length antibody of the human subclass IgG1 with the mutations L234A, L235A and P329G,
d) a full length antibody of the human subclass IgG4 with the mutations S228P, L235E and P329G,
e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain.

One aspect as reported herein is an anti-human alpha-synuclein antibody, characterized in that
a) the antibody comprises two antibody heavy chains each comprising a heavy chain variable domain and a heavy chain constant region, wherein
  i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
  ii) the constant region is a human kappa light chain constant region or a human lambda light chain constant region.

One aspect as reported herein is an anti-human alpha-synuclein antibody, characterized in that
a) the antibody comprises two antibody heavy chains each comprising a heavy chain variable domain and a heavy chain constant region, wherein
  i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
  ii) the constant region is a human kappa light chain constant region or a human lambda light chain constant region.

One aspect as reported herein is an anti-human alpha-synuclein antibody, characterized in that
a) the antibody comprises two antibody heavy chains each comprising a heavy chain variable domain and a heavy chain constant region, wherein
  i) the variable domain is a humanized form of the non-human (rabbit) variable domain of SEQ ID NO: 26,
  ii) the constant region is a human IgG1 constant region, wherein the C-terminal lysine residue can be present or absent, and
  iii) the constant region comprises the amino acid changes L234A, L235A and P329G,
b) the antibody comprises two antibody light chains each comprising a light chain variable domain and a light chain constant domain, wherein
  i) the variable domain is a humanized form of the non-human (rabbit) variable domain of SEQ ID NO: 27,
  ii) the constant region is a human kappa light chain constant region or a human lambda light chain constant region.

One aspect as reported herein is an anti-human alpha-synuclein antibody, characterized in that
a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
  i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
  ii) the constant region is a human IgG1 constant region, wherein the C-terminal lysine residue can be present or absent, and
  iii) the constant region comprises the amino acid changes L234A, L235A and P329G, b) the antibody comprises two antibody light chains each comprising a light chain variable domain and a light chain constant domain, wherein
  i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
  ii) the constant region is a human kappa light chain constant region or a human lambda light chain constant region.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
    ii) the constant region is a human kappa light chain constant region or a human lambda light chain constant region.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain is a humanized form of the rabbit variable domain of SEQ ID NO: 26,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain is a humanized form of the rabbit variable domain of SEQ ID NO: 27,
    ii) the constant region is a human kappa light chain constant region or a human lambda light chain constant region.

One aspect as reported herein is an anti-human alpha-synuclein antibody, characterized in that
  a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent,
    iii) the constant region comprises the amino acid changes L234A, L235A and P329G, and
    iv) the constant region comprises either the amino acid changes T366W and S354C or the amino acid changes T366S, L368A, Y407V and Y349C,
  b) the antibody comprises a second antibody heavy chain comprising in N- to C-terminal direction a heavy chain variable domain and a heavy chain constant region, wherein
    i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent,
    iii) the constant region comprises the amino acid changes L234A, L235A and P329G, and
    iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
  c) the antibody comprises two antibody light chains each comprising a light chain variable domain and a light chain constant domain, wherein
    i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
    ii) the constant region is a human kappa light chain constant region or a human lambda light chain constant region.

One aspect as reported herein is an anti-human alpha-synuclein antibody, characterized in that
  a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent,
    iii) the constant region comprises the amino acid changes L234A, L235A and P329G, and
    iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein
   i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
   ii) the constant region is a human IgG1 constant region, wherein the C-terminal lysine residue can be present or absent,
   iii) the constant region comprises the amino acid changes L234A, L235A and P329G, and
   iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
   i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
   ii) the constant region is a human kappa light chain constant region or a human lambda light chain constant region.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
   i) the variable domain is a humanized form of the rabbit variable domain of SEQ ID NO: 26,
   ii) the constant region is a human IgG1 constant region, wherein the C-terminal lysine residue can be present or absent,
   iii) the constant region comprises the amino acid changes L234A, L235A and P329G, and
   iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
   i) the variable domain is a humanized form of the rabbit variable domain of SEQ ID NO: 26,
   ii) the constant region is a human IgG1 constant region, wherein the C-terminal lysine residue can be present or absent,
   iii) the constant region comprises the amino acid changes L234A, L235A and P329G, and
   iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
   i) the variable domain is a humanized form of the rabbit variable domain of SEQ ID NO: 27,
   ii) the constant region is a human kappa light chain constant region or a human lambda light chain constant region.

In one embodiment the antibody fragment, which specifically binds to human transferrin receptor, comprises a heavy chain variable domain that is a humanized form of the heavy chain variable domain of SEQ ID NO: 56 and a light chain variable domain that is a humanized form of the light chain variable domain of SEQ ID NO: 57.

In one embodiment of all previous aspects the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells, and/or
   iv) specifically binds to alpha-synuclein that has a free N-terminal methionine residue and does not specifically bind to alpha-synuclein has a modified N-terminal methionine residue.

One aspect as reported herein is an antibody that specifically binds to human alpha-synuclein, wherein the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

In one embodiment of all aspects and embodiments the human neuronal cell is a tetracycline-controlled, v-myc-overexpressing human mesencephalic-derived cell line. In one embodiment of all aspects and embodiments the human neuronal cells are Lund human mesencephalic (LUHMES) cells.

In one embodiment the caspase activity is caspase 3 and/or caspase 7 activity.

In one embodiment the antibody is for use in the treatment of synucleinopathies.

In one embodiment the antibody is for use in the treatment of Parkinson's Disease.

In one embodiment the antibody is effector function silent. In one embodiment the antibody has no effector function.

In one embodiment the antibody specifically binds to a peptide consisting of the amino acid sequence GKNEE-GAPQEG (SEQ ID NO: 01).

In one embodiment the antibody has a binding affinity for monomeric human alpha-synuclein of less than $10^{-09}$ M and more than $10^{-07}$ M.

In one embodiment the antibody specifically binds to monomeric and oligomeric human alpha-synuclein.

In one embodiment the antibody comprises in the heavy chain variable domain the HVRs of SEQ ID NO: 02 to 04 and in the light chain variable domain the HVRs of SEQ ID NO: 05 to 07.

In one embodiment the antibody comprises in the heavy chain variable domain the HVRs of SEQ ID NO: 08, 09 and 04 and in the light chain variable domain the HVRs of SEQ ID NO: 10 to 12.

In one embodiment the antibody comprises a heavy chain variable domain consisting of SEQ ID NO: 13 and a light chain variable domain consisting of SEQ ID NO: 14.

In one embodiment the antibody has been obtained by humanizing an antibody comprising a heavy chain variable domain consisting of SEQ ID NO: 13 and a light chain variable domain consisting of SEQ ID NO: 14.

In one embodiment the antibody is a humanized antibody and comprises in the heavy chain variable domain the HVRs of SEQ ID NO: 02 to 04 and in the light chain variable domain the HVRs of SEQ ID NO: 05 to 07, wherein in each HVR up to 3 amino acid residues can be changed.

In one embodiment the antibody is a humanized antibody and comprises in the heavy chain variable domain the HVRs of SEQ ID NO: 08, 09 and 04 and in the light chain variable domain the HVRs of SEQ ID NO: 10 to 12, wherein in each HVR up to 3 amino acid residues can be changed.

In one embodiment the antibody is a humanized antibody and the heavy chain variable domain is derived from a heavy chain variable domain consisting of SEQ ID NO: 13 and a light chain variable domain is derived from a light chain variable domain consisting of SEQ ID NO: 14.

In one embodiment the antibody binds to the same epitope as an antibody comprising in the heavy chain the HVRs of SEQ ID NO: 15 to 17 and in the light chain the HVRs of SEQ ID NO: 18 to 20.

In one embodiment the antibody binds to the same epitope as an antibody comprising in the heavy chain the HVRs of SEQ ID NO: 21, 22 and 17 and in the light chain the HVRs of SEQ ID NO: 23 to 25.

In one embodiment the antibody comprises a heavy chain variable domain consisting of SEQ ID NO: 26 and a light chain variable domain consisting of SEQ ID NO: 27.

In one embodiment the antibody has been obtained by humanizing an antibody comprising a heavy chain variable domain consisting of SEQ ID NO: 26 and a light chain variable domain consisting of SEQ ID NO: 27.

In one embodiment the antibody is a humanized antibody and comprises in the heavy chain variable domain the HVRs of SEQ ID NO: 15 to 17 and in the light chain variable domain the HVRs of SEQ ID NO: 18 to 20, wherein in each HVR up to 3 amino acid residues can be changed.

In one embodiment the antibody is a humanized antibody and comprises in the heavy chain variable domain the HVRs of SEQ ID NO: 21, 22 and 17 and in the light chain variable domain the HVRs of SEQ ID NO: 23 to 25, wherein in each HVR up to 3 amino acid residues can be changed.

In one embodiment the antibody is a humanized antibody and the heavy chain variable domain is derived from a heavy chain variable domain consisting of SEQ ID NO: 26 and a light chain variable domain is derived from a light chain variable domain consisting of SEQ ID NO: 27.

In one embodiment the antibody binds to the same epitope as an antibody comprising in the heavy chain the HVRs of SEQ ID NO: 28 to 30 and in the light chain the HVRs of SEQ ID NO: 31 to 33.

In one embodiment the antibody binds to the same epitope as an antibody comprising in the heavy chain the HVRs of SEQ ID NO: 28, 34 and 30 and in the light chain the HVRs of SEQ ID NO: 35 to 37.

In one embodiment the antibody comprises a heavy chain variable domain consisting of SEQ ID NO: 38 and a light chain variable domain consisting of SEQ ID NO: 39.

In one embodiment the antibody has been obtained by humanizing an antibody comprising a heavy chain variable domain consisting of SEQ ID NO: 38 and a light chain variable domain consisting of SEQ ID NO: 39.

In one embodiment the antibody is a humanized antibody and comprises in the heavy chain variable domain the HVRs of SEQ ID NO: 28 to 30 and in the light chain variable domain the HVRs of SEQ ID NO: 31 to 33, wherein in each HVR up to 3 amino acid residues can be changed.

In one embodiment the antibody is a humanized antibody and comprises in the heavy chain variable domain the HVRs of SEQ ID NO: 28, 34 and 30 and in the light chain variable domain the HVRs of SEQ ID NO: 35 to 37, wherein in each HVR up to 3 amino acid residues can be changed.

In one embodiment the antibody is a humanized antibody and the heavy chain variable domain is derived from a heavy chain variable domain consisting of SEQ ID NO: 38 and a light chain variable domain is derived from a light chain variable domain consisting of SEQ ID NO: 39.

In one embodiment the antibody specifically binds to fibrillar human alpha-synuclein and does not bind to non-fibrillar human alpha-synuclein In one embodiment the antibody is conjugated to a blood-brain-barrier shuttle module.

In one embodiment the blood-brain-barrier shuttle module is an antibody or antibody fragment that specifically binds to LRP1, LRP8, human transferrin receptor or human insulin-like growth factor receptor.

In one embodiment the antibody is a monoclonal antibody.

In one embodiment the antibody is a humanized antibody or a chimeric antibody.

In one embodiment the antibody is an antibody fragment that binds to human alpha-synuclein and
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

In one embodiment the antibody is
  a) a full length antibody of the human subclass IgG1, or
  b) a full length antibody of the human subclass IgG4, or
  c) a full length antibody of the human subclass IgG1 with the mutations L234A, L235A and P329G,
  d) a full length antibody of the human subclass IgG4 with the mutations S228P, L235E and P329G,
  e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
  f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain.

One aspect as reported herein is an anti-human alpha-synuclein antibody, characterized in that
  a) the antibody comprises two antibody heavy chains each comprising a heavy chain variable domain and a heavy chain constant region, wherein
    i) the variable domain comprises the HVRs of SEQ ID NO: 02, SEQ ID NO: 03 and SEQ ID NO: 04, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G, b) the antibody comprises two antibody light chains each comprising a light chain variable domain and a light chain constant domain, wherein
   i) the variable domain comprises the HVRs of SEQ ID NO: 05, SEQ ID NO: 06 and SEQ ID NO: 07, wherein in each HVR independently of each other 0, 1, 2 or 3 amino acid residues are changed,
   ii) the constant region is a human kappa light chain constant region or a human lambda light chain constant region, and c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
   a) the antibody comprises two antibody heavy chains each comprising a heavy chain variable domain and a heavy chain constant region, wherein
      i) the variable domain comprises the HVRs of SEQ ID NO: 08, SEQ ID NO: 09 and SEQ ID NO: 04, wherein in each HVR independently of each other 0, 1, 2 or 3 amino acid residues are changed,
      ii) the constant region is a human IgG1 constant region, wherein the C-terminal lysine residue can be present or absent, and
      iii) the constant region comprises the amino acid changes L234A, L235A and P329G,
   b) the antibody comprises two antibody light chains each comprising a light chain variable domain and a light chain constant domain, wherein
      i) the variable domain comprises the HVRs of SEQ ID NO: 10, SEQ ID NO: 11 and SEQ ID NO: 12, wherein in each HVR independently of each other 0, 1, 2 or 3 amino acid residues are changed,
      ii) the constant region is a human kappa light chain constant region or a human lambda light chain constant region, and c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
   a) the antibody comprises two antibody heavy chains each comprising a heavy chain variable domain and a heavy chain constant region, wherein
      i) the variable domain is a humanized form of the non-human (rabbit) variable domain of SEQ ID NO: 13,
      ii) the constant region is a human IgG1 constant region, wherein the C-terminal lysine residue can be present or absent, and
      iii) the constant region comprises the amino acid changes L234A, L235A and P329G,
   b) the antibody comprises two antibody light chains each comprising a light chain variable domain and a light chain constant domain, wherein
      i) the variable domain is a humanized form of the non-human (rabbit) variable domain of SEQ ID NO: 14,
      ii) the constant region is a human kappa light chain constant region or a human lambda light chain constant region, and c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
   a) the antibody comprises two antibody heavy chains each comprising a heavy chain variable domain and a heavy chain constant region, wherein
      i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
      ii) the constant region is a human IgG1 constant region, wherein the C-terminal lysine residue can be present or absent, and
      iii) the constant region comprises the amino acid changes L234A, L235A and P329G,
   b) the antibody comprises two antibody light chains each comprising a light chain variable domain and a light chain constant domain, wherein
      i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
      ii) the constant region is a human kappa light chain constant region or a human lambda light chain constant region, and c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
   a) the antibody comprises two antibody heavy chains each comprising a heavy chain variable domain and a heavy chain constant region, wherein
      i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
      ii) the constant region is a human IgG1 constant region, wherein the C-terminal lysine residue can be present or absent, and
      iii) the constant region comprises the amino acid changes L234A, L235A and P329G, b) the antibody comprises two antibody light chains each comprising a light chain variable domain and a light chain constant domain, wherein
   i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
   ii) the constant region is a human kappa light chain constant region or a human lambda light chain constant region,
and
c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
a) the antibody comprises two antibody heavy chains each comprising a heavy chain variable domain and a heavy chain constant region, wherein
   i) the variable domain is a humanized form of the non-human (rabbit) variable domain of SEQ ID NO: 26,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain is a humanized form of the non-human (rabbit) variable domain of SEQ ID NO: 27,
   ii) the constant region is a human kappa light chain constant region or a human lambda light chain constant region,
and
c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
a) the antibody comprises two antibody heavy chains each comprising a heavy chain variable domain and a heavy chain constant region, wherein
   i) the variable domain comprises the HVRs of SEQ ID NO: 28, SEQ ID NO: 29 and SEQ ID NO: 30, wherein in each HVR independently of each other 0, 1, 2 or 3 amino acid residues are changed,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain comprises the HVRs of SEQ ID NO: 31, SEQ ID NO: 32 and SEQ ID NO: 33, wherein in each HVR independently of each other 0, 1, 2 or 3 amino acid residues are changed,
   ii) the constant region is a human kappa light chain constant region or a human lambda light chain constant region,
and
c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
a) the antibody comprises two antibody heavy chains each comprising a heavy chain variable domain and a heavy chain constant region, wherein
   i) the variable domain comprises the HVRs of SEQ ID NO: 28, SEQ ID NO: 34 and SEQ ID NO: 30, wherein in each HVR independently of each other 0, 1, 2 or 3 amino acid residues are changed,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain comprises the HVRs of SEQ ID NO: 35, SEQ ID NO: 36 and SEQ ID NO: 37, wherein in each HVR independently of each other 0, 1, 2 or 3 amino acid residues are changed,
   ii) the constant region is a human kappa light chain constant region or a human lambda light chain constant region,
and
c) the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells.

One aspect as reported herein is an anti-human alpha-synuclein antibody, characterized in that
a) the antibody comprises two antibody heavy chains each comprising a heavy chain variable domain and a heavy chain constant region, wherein
   i) the variable domain is a humanized form of the non-human (rabbit) variable domain of SEQ ID NO: 38,
   ii) the constant region is a human IgG1 constant region, wherein the C-terminal lysine residue can be present or absent, and
   iii) the constant region comprises the amino acid changes L234A, L235A and P329G,
b) the antibody comprises two antibody light chains each comprising a light chain variable domain and a light chain constant domain, wherein
   i) the variable domain is a humanized form of the non-human (rabbit) variable domain of SEQ ID NO: 39,
   ii) the constant region is a human kappa light chain constant region or a human lambda light chain constant region, and
c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 02, SEQ ID NO: 03 and SEQ ID NO: 04, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 05, SEQ ID NO: 06 and SEQ ID NO: 07, wherein in each HVR independently of each other 0, 1, 2 or 3 amino acid residues are changed,
    ii) the constant region is a human kappa light chain constant region or a human lambda light chain constant region,
and
c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 08, SEQ ID NO: 09 and SEQ ID NO: 04, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 10, SEQ ID NO: 11 and SEQ ID NO: 12, wherein in each HVR independently of each other 0, 1, 2 or 3 amino acid residues are changed,
    ii) the constant region is a human kappa light chain constant region or a human lambda light chain constant region,
and
c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain is a humanized form of the rabbit variable domain of SEQ ID NO: 13,
    ii) the constant region is a human IgG constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain is a humanized form of the rabbit variable domain of SEQ ID NO: 14,
    ii) the constant region is a human kappa light chain constant region or a human lambda light chain constant region,
and
c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 18, SEQ ID NO: 19 and SEQ ID NO: 20, wherein in each HVR independently of each other 0, 1, 2 or 3 amino acid residues are changed, ii) the constant region is a human kappa light chain constant region or a human lambda light chain constant region, and c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
    ii) the constant region is a human kappa light chain constant region or a human lambda light chain constant region,
  and
  c) the antibody
    i) inhibits alpha-synuclein induced cytotoxicity in human neurons and glia cells, and/or
    ii) inhibits cell-to-cell transmission of oligomeric human alpha-synuclein between neurons and glia cells, and/or
    iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain is a humanized form of the rabbit variable domain of SEQ ID NO: 26,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain is a humanized form of the rabbit variable domain of SEQ ID NO: 27, ii) the constant region is a human kappa light chain constant region or a human lambda light chain constant region, and c) the antibody
  i) inhibits alpha-synuclein induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 28, SEQ ID NO: 29 and SEQ ID NO: 30, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 31, SEQ ID NO: 32 and SEQ ID NO: 33, wherein in each HVR independently of each other 0, 1, 2 or 3 amino acid residues are changed,
    ii) the constant region is a human kappa light chain constant region or a human lambda light chain constant region,
  and
  c) the antibody
    i) inhibits alpha-synuclein induced cytotoxicity in human neurons and glia cells, and/or
    ii) inhibits cell-to-cell transmission of oligomeric human alpha-synuclein between neurons and glia cells, and/or
    iii) reduces alpha-synuclein-induced caspase activity in human neuronal cells.

One aspect as reported herein is an anti-human alpha-synuclein antibody, characterized in that
  a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
    i) the variable domain comprises the HVRs of SEQ ID NO: 28, SEQ ID NO: 34 and SEQ ID NO: 30, wherein in each HVR independently of each other 0, 1, 2 or 3 amino acid residues are changed,
    ii) the constant region is a human IgG1 constant region, wherein the C-terminal lysine residue can be present or absent, and
    iii) the constant region comprises the amino acid changes L234A, L235A and P329G,
  b) the antibody comprises two antibody light chains each comprising a light chain variable domain and a light chain constant domain, wherein
    i) the variable domain comprises the HVRs of SEQ ID NO: 35, SEQ ID NO: 36 and SEQ ID NO: 37, wherein in each HVR independently of each other 0, 1, 2 or 3 amino acid residues are changed, ii) the constant region is a human kappa light chain constant region or a human lambda light chain constant region, and c) the antibody i) inhibits alpha-synuclein induced cytotoxicity in human neurons and glia cells, and/or ii) inhibits cell-to-cell transmission of oligomeric human alpha-synuclein between neurons and glia cells, and/or iii) reduces alpha-synuclein-induced caspase activity in human neuronal cells.

One aspect as reported herein is an anti-human alpha-synuclein antibody, characterized in that a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein i) the variable domain is a humanized form of the rabbit variable domain of SEQ ID NO: 38, ii) the constant region is a human IgG1 constant region, wherein the C-terminal lysine residue can be present or absent, and iii) the constant region comprises the amino acid changes L234A, L235A and P329G, b) the antibody comprises two antibody light chains each comprising a light chain variable domain and a light chain constant domain, wherein i) the variable domain is a humanized form of the rabbit variable domain of SEQ ID NO: 39, ii) the constant region is a human kappa light chain constant region or a human lambda light chain constant region, and c) the antibody i) inhibits alpha-synuclein induced cytotoxicity in human neurons and glia cells, and/or ii) inhibits cell-to-cell transmission of oligomeric human alpha-synuclein between neurons and glia cells, and/or iii) reduces alpha-synuclein-induced caspase activity in human neuronal cells.

One aspect as reported herein is an anti-human alpha-synuclein antibody, characterized in that a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein i) the variable domain comprises the HVRs of SEQ ID NO: 02, SEQ ID NO: 03 and SEQ ID NO: 04, wherein in each HVR independently of each other 0, 1, 2 or 3 amino acid residues are changed, ii) the constant region is a human IgG1 constant region, wherein the C-terminal lysine residue can be present or absent, iii) the constant region comprises the amino acid changes L234A, L235A and P329G, and iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein i) the variable domain comprises the HVRs of SEQ ID NO: 02, SEQ ID NO: 03 and SEQ ID NO: 04, wherein in each HVR independently of each other 0, 1, 2 or 3 amino acid residues are changed, ii) the constant region is a human IgG1 constant region, wherein the C-terminal lysine residue can be present or absent, iii) the constant region comprises the amino acid changes L234A, L235A and P329G, and iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C, c) the antibody comprises two antibody light chains each comprising a light chain variable domain and a light chain constant domain, wherein i) the variable domain comprises the HVRs of SEQ ID NO: 05, SEQ ID NO: 06 and SEQ ID NO: 07, wherein in each HVR independently of each other 0, 1, 2 or 3 amino acid residues are changed, ii) the constant region is a human kappa light chain constant region or a human lambda light chain constant region, and d) the antibody i) inhibits alpha-synuclein induced cytotoxicity in human neurons and glia cells, and/or ii) inhibits cell-to-cell transmission of oligomeric human alpha-synuclein between neurons and glia cells, and/or iii) reduces alpha-synuclein-induced caspase activity in human neuronal cells.

One aspect as reported herein is an anti-human alpha-synuclein antibody, characterized in that a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein i) the variable domain comprises the HVRs of SEQ ID NO: 08, SEQ ID NO: 09 and SEQ ID NO: 04, wherein in each HVR independently of each other 0, 1, 2 or 3 amino acid residues are changed, ii) the constant region is a human IgG1 constant region, wherein the C-terminal lysine residue can be present or absent, iii) the constant region comprises the amino acid changes L234A, L235A and P329G, and iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein i) the variable domain comprises the HVRs of SEQ ID NO: 08, SEQ ID NO: 09 and SEQ ID NO: 04, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
i) the variable domain comprises the HVRs of SEQ ID NO: 10, SEQ ID NO: 11 and SEQ ID NO: 12, wherein in each HVR independently of each other 0, 1, 2 or 3 amino acid residues are changed,
ii) the constant region is a human kappa light chain constant region or a human lambda light chain constant region,
and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain is a humanized form of the rabbit variable domain of SEQ ID NO: 13,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
i) the variable domain is a humanized form of the rabbit variable domain of SEQ ID NO: 13,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
i) the variable domain is a humanized form of the rabbit variable domain of SEQ ID NO: 14,
ii) the constant region is a human kappa light chain constant region or a human lambda light chain constant region,
and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
ii) the constant region is a human kappa light chain constant region or a human lambda light chain constant region, and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
ii) the constant region is a human kappa light chain constant region or a human lambda light chain constant region, and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain is a humanized form of the rabbit variable domain of SEQ ID NO: 26,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
i) the variable domain is a humanized form of the rabbit variable domain of SEQ ID NO: 26,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
i) the variable domain is a humanized form of the rabbit variable domain of SEQ ID NO: 27,
ii) the constant region is a human kappa light chain constant region or a human lambda light chain constant region, and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFv or scFv antibody fragment, which specifically binds to human transferrin receptor, wherein
i) the variable domain comprises the HVRs of SEQ ID NO: 28, SEQ ID NO: 29 and SEQ ID NO: 30, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein
i) the variable domain comprises the HVRs of SEQ ID NO: 28, SEQ ID NO: 29 and SEQ ID NO: 30, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C, c) the antibody comprises two antibody light chains each comprising a light chain variable domain and a light chain constant domain, wherein
i) the variable domain comprises the HVRs of SEQ ID NO: 31, SEQ ID NO: 32 and SEQ ID NO: 33, wherein in each HVR independently of each other 0, 1, 2 or 3 amino acid residues are changed,
ii) the constant region is a human kappa light chain constant region or a human lambda light chain constant region, and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 28, SEQ ID NO: 34 and SEQ ID NO: 30, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein
i) the variable domain comprises the HVRs of SEQ ID NO: 28, SEQ ID NO: 34 and SEQ ID NO: 30, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C, c) the antibody comprises two antibody light chains each comprising a light chain variable domain and a light chain constant domain, wherein
i) the variable domain comprises the HVRs of SEQ ID NO: 35, SEQ ID NO: 36 and SEQ ID NO: 37, wherein in each HVR independently of each other 0, 1, 2 or 3 amino acid residues are changed,
ii) the constant region is a human kappa light chain constant region or a human lambda light chain constant region, and
d) the antibody
i) inhibits alpha-synuclein induced cytotoxicity in human neurons and glia cells, and/or
ii) inhibits cell-to-cell transmission of oligomeric human alpha-synuclein between neurons and glia cells, and/or
iii) reduces alpha-synuclein-induced caspase activity in human neuronal cells.

One aspect as reported herein is an anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain is a humanized form of the rabbit variable domain of SEQ ID NO: 38,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein
i) the variable domain is a humanized form of the rabbit variable domain of SEQ ID NO: 38, ii) the constant region is a human IgG1 constant region, wherein the C-terminal lysine residue can be present or absent, iii) the constant region comprises the amino acid changes L234A, L235A and P329G, and iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C, c) the antibody comprises two antibody light chains each comprising a light chain variable domain and a light chain constant domain, wherein i) the variable domain is a humanized form of the rabbit variable domain of SEQ ID NO: 39, ii) the constant region is a human kappa light chain constant region or a human lambda light chain constant region, and d) the antibody i) inhibits alpha-synuclein induced cytotoxicity in human neurons and glia cells, and/or ii) inhibits cell-to-cell transmission of oligomeric human alpha-synuclein between neurons and glia cells, and/or iii) reduces alpha-synuclein-induced caspase activity in human neuronal cells.

In one embodiment the antibody fragment comprises a heavy chain variable domain that is a humanized form of the heavy chain variable domain of SEQ ID NO: 56 and a light chain variable domain that is a humanized form of the light chain variable domain of SEQ ID NO: 57.

One aspect as reported herein is an isolated nucleic acid encoding the antibody as reported herein.

One aspect as reported herein is a host cell comprising the nucleic acid as reported herein.

One aspect as reported herein is a method of producing an antibody comprising the steps of culturing the host cell as reported herein so that the antibody is produced.

In one embodiment the method further comprises the step of recovering the antibody from the cell or the cultivation medium.

One aspect as reported herein is a pharmaceutical formulation comprising the antibody as reported herein and a pharmaceutically acceptable carrier.

In one embodiment the pharmaceutical formulation further comprises an additional therapeutic agent.

One aspect as reported herein is the antibody as reported herein for use as a medicament.

One aspect as reported herein is the antibody as reported herein for use in treating synucleinopathies.

One aspect as reported herein is the antibody as reported herein for use in treating Parkinson's Disease.

One aspect as reported herein is the antibody as reported herein for use in inhibiting alpha-synuclein induced cytotoxicity in human neurons and glia cells.

One aspect as reported herein is the antibody as reported herein for use in inhibiting cell-to-cell transmission of oligomeric human alpha-synuclein between neurons and glia cells.

One aspect as reported herein is the antibody as reported herein for use in reducing alpha-synuclein-induced caspase activity in neuronal cells or glia cells.

One aspect as reported herein is the use of the antibody as reported herein in the manufacture of a medicament.

In one embodiment the medicament is for treatment of Parkinson's Disease.

In one embodiment the medicament is for inhibiting alpha-synuclein induced cytotoxicity in human neurons and glia cells.

In one embodiment the medicament is for inhibiting cell-to-cell transmission of oligomeric human alpha-synuclein between neurons and glia cells.

In one embodiment the medicament is for reducing alpha-synuclein-induced caspase activity in neuronal cells or glia cells.

One aspect as reported herein is a method of treating an individual having Parkinson's Disease comprising administering to the individual an effective amount of the antibody as reported herein.

One aspect as reported herein is a method of inhibiting alpha-synuclein induced cytotoxicity in human neurons and glia cells in an individual comprising administering to the individual an effective amount of the antibody as reported herein to inhibit alpha-synuclein induced cytotoxicity in human neurons and glia cells.

One aspect as reported herein is a method of inhibiting cell-to-cell transmission of oligomeric human alpha-synuclein between neurons and glia cells in an individual comprising administering to the individual an effective amount of the antibody as reported herein to inhibit alpha-synuclein induced cytotoxicity in human neurons and glia cells.

One aspect as reported herein is the use of an anti-human alpha synuclein antibody as reported herein in the inhibition of alpha-synuclein induced cytotoxicity in human neurons and glia cells.

One aspect as reported herein is the use of an anti-human alpha synuclein antibody as reported herein in the inhibition of cell-to-cell transmission of oligomeric human alpha-synuclein between neurons and glia cells.

One aspect as reported herein is the use of an anti-human alpha synuclein antibody as reported herein in the reduction of alpha-synuclein-induced caspase activity in neuronal cells or glia cells.

The antibodies as reported herein can be used in the treatment of Parkinson disease. Without being bound by this theory the antibodies inhibit the spreading of toxic oligomeric alpha-synuclein, or inhibit the uptake of toxic oligomeric alpha-synuclein by neurons and glia cells, or reduce neuroinflammation.

With the antibodies as reported herein inhibition/reduction of progression of synucleinopathy and neuropathology can be affected.

The antibodies as reported herein can be used to protect from development of Parkinson's Disease or even be used to stop the progression of Parkinson's Disease. In one embodiment the antibody as reported herein i) binds to alpha-synuclein on brain sections of alpha-synuclein transgenic mice and Parkinson's Disease patients; and/or labels alpha-synuclein in LUHMES cells.

The antibodies as reported herein can be used for the treatment of a synucleinopathy. Some synucleinopathies are neurodegeneration with brain iron accumulation type 1 (NBIA1), pure autonomic failure, Down's syndrome, complex of Guam, and several Lewy body disorders, such as diffuse Lewy body disease (DLBD), the Lewy body variant of Alzheimer's disease (LBVAD), certain forms of Gaucher's Disease and Parkinson's Disease dementia (PDD).

One aspect as reported herein is an antibody that specifically binds to the amino acid sequence of SEQ ID NO: 01 in human alpha-synuclein.

One aspect as reported herein is an antibody that binds to the same epitope as an antibody comprising the heavy chain variable domain of SEQ ID NO: 13 and the light chain variable domain of SEQ ID NO: 14.

One aspect as reported herein is an antibody that binds to the same epitope as an antibody comprising the heavy chain variable domain of SEQ ID NO: 26 and the light chain variable domain of SEQ ID NO: 27.

One aspect as reported herein is an antibody that binds to the same epitope as an antibody comprising the heavy chain variable domain of SEQ ID NO: 38 and the light chain variable domain of SEQ ID NO: 39.

BRIEF DESCRIPTION OF THE FIGURES

(FIG. 7A) antibody 0017; (FIG. 7B) antibody 0018; (FIG. 7C) antibody 12F4 (reference).

Figure 1:
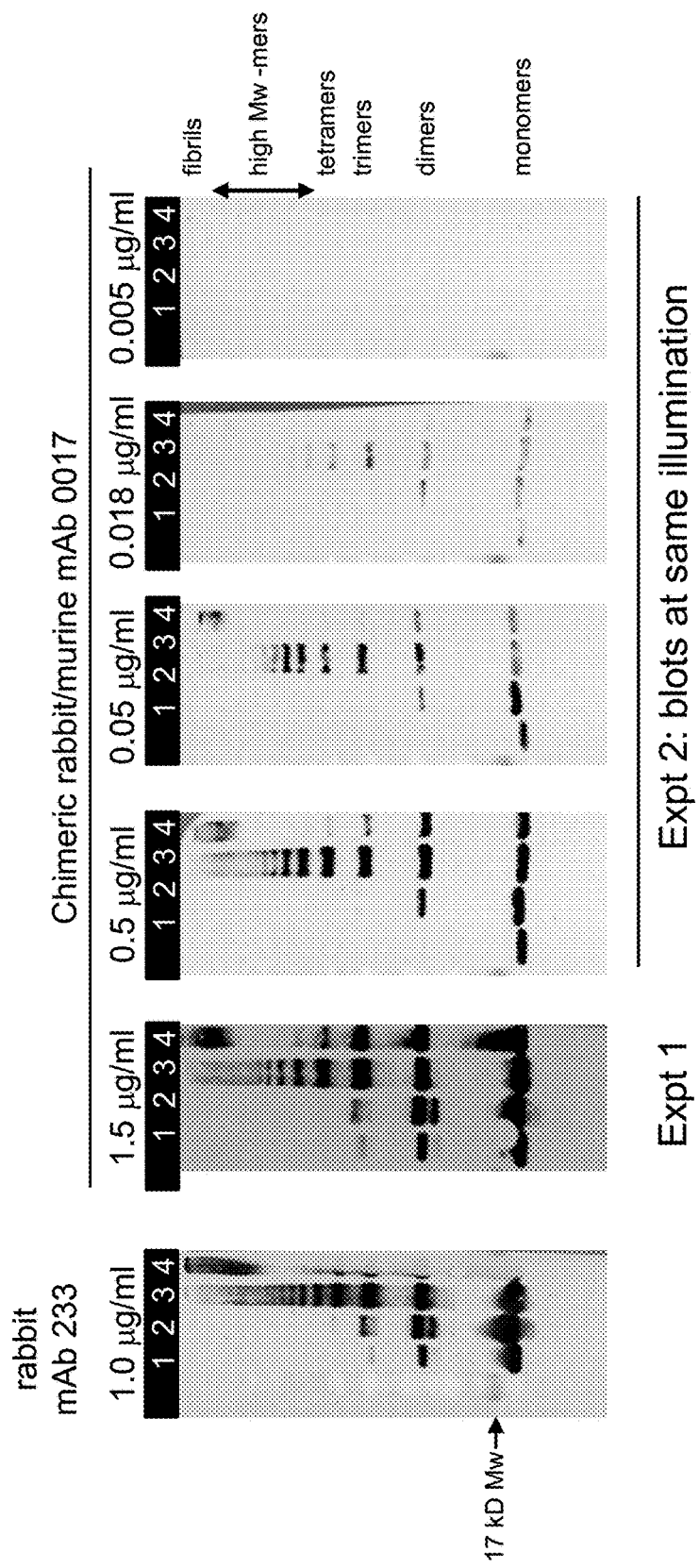
FIG. 1: Concentration dependent binding specificity of anti-alpha-synuclein-antibody 0017; Lane: 1) fibrillar alpha-synuclein preparation, 2) triple-proline mutant alpha-synuclein oligomers, 3) type A alpha-synuclein oligomers, 4) type C alpha-synuclein oligomers.

1: monomer, free N-terminus, 4.2 mg/mL, never thawed;
2: monomer, His-tagged N-terminus, 4.8 mg/mL;
3: dimer, free N-terminus, 1.6 mg/mL.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd).

Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-human alpha-synuclein antibody" and "an antibody that binds to human alpha-synuclein" refer to an antibody that is capable of binding human alpha-synuclein with sufficient affinity such that the antibody is useful as a diagnostic and/or therapeutic agent in targeting human alpha-synuclein. In one embodiment, the extent of binding of an anti-human alpha-synuclein antibody to an unrelated, non-human alpha-synuclein protein is less than about 10% of the binding of the antibody to human alpha-synuclein as measured, e.g., by a radioimmunoassay (RIA).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that has binding interactions with the same residues as the reference antibody on the antigen. The binding interaction can be determined using surface plasmon resonance and mutated antigen or X-ray structure analysis of the antibody-antigen complex.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region.

The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) and sometimes the C-terminal lysine-glycine dipeptide (Gly446Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s) such as a blood-brain-barrier shuttle module.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human alpha-synuclein antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

The term "human alpha-synuclein", as used herein, refers to native human alpha-synuclein (UniProt P37840). The term encompasses "full-length", unprocessed human alpha-synuclein as well as any form of human alpha-synuclein that results from processing in the cell. The term also encompasses naturally occurring variants of human alpha-synuclein, e.g., mutants, splice variants or allelic variants. The amino acid sequence of human alpha-synuclein is shown in SEQ ID NO: 40.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked.

Such vectors are referred to herein as "expression vectors".

II. Compositions and Methods

In one aspect, the invention is based, in part, on the finding that the antibodies as reported herein can be used to reduce/eliminate alpha-synuclein induced toxicity in neuronal and glia cells in the brain. In certain aspects, antibodies that bind to human alpha-synuclein are provided. Antibodies of the invention are useful, e.g., for the diagnosis or treatment of synucleinopathy and neuropathy, especially Parkinson's Disease and Alzheimer's Disease with Parkinson's Disease comorbidity.

A. Exemplary Anti-Human Alpha-Synuclein Antibodies

The antibodies as reported herein have been obtained by applying a deliberate immunization methodology and purposive selection of antibodies with specific binding properties.

At first rabbits have been immunized with a mixture of various assemblies and aggregates of recombinant alpha-synuclein. The isolated B-cells clones have been characterized by ELISA and the best binders have been selected. In the next step the antibodies have been characterized by epitope mapping using the peptide array methodology and by determining their selectivity towards monomeric and oligomeric recombinant alpha-synuclein e.g. using Western Blot. Also the binding of the antibodies to recombinant alpha-synuclein and physiological alpha-synuclein in human neuronal cells and to pathological alpha-synuclein in brain sections of human alpha-synuclein transgenic mice and Parkinson disease patients has been determined. Based on the data outlined before candidates were selected and acute in vivo binding to pathological alpha-synuclein after peripheral injection has been determined. The most efficient binders were selected thereafter. With the selected most efficient binder the clearance of alpha-synuclein pathology and/or stop of progression of alpha-synuclein pathology in Thy1-(A30P)aSYN transgenic mice will be determined.

One preferred antibody is the antibody 0017. This antibody has a broad alpha-synuclein specific binding profile, i.e. this antibody binds to monomeric and aggregated (oligomeric) human alpha-synuclein. In FIG. 1 the concentration dependent binding of antibody 0017 towards monomeric and multiple aggregated forms of human alpha-synuclein is shown. The antibody 0017 is a chimeric antibody with variable domains of a rabbit antibody 233 selected by the procedure as outlined before and murine constant regions.

Figure 2:
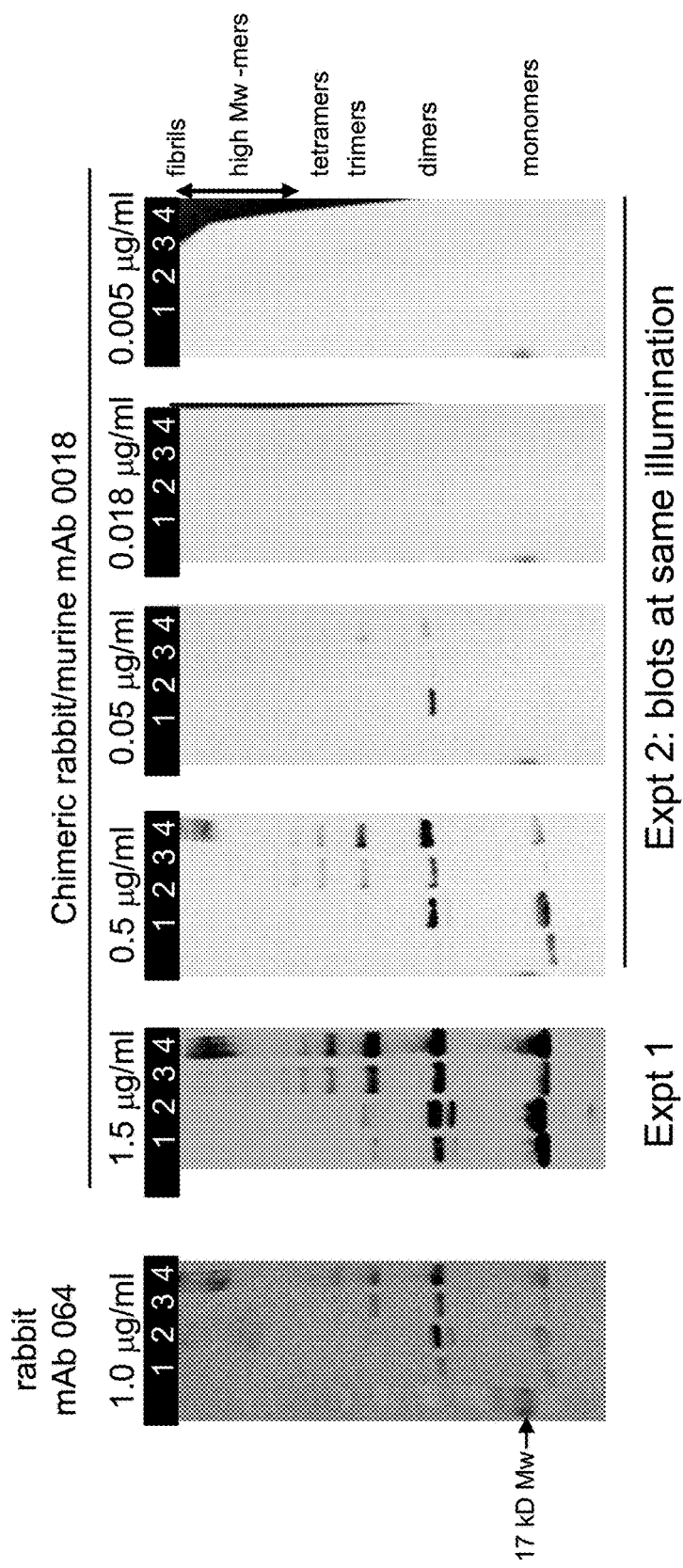
FIG. 2: Concentration dependent binding specificity of anti-alpha-synuclein-antibody 0018; Lane: 1) fibrillar alpha-synuclein preparation, 2) triple-proline mutant alpha-synuclein oligomers, 3) type A alpha-synuclein oligomers, 4) type C alpha-synuclein oligomers.

Another preferred antibody is the antibody 0018. This antibody has an alpha-synuclein aggregation dependent binding profile, i.e. this antibody binds to monomeric, dimeric and oligomeric human alpha-synuclein, whereby the binding to monomeric human and mouse alpha-synuclein is diminished if the N-terminal methionine residue is modified, e.g. by acetylation or biotinylation, or is absent. In FIG. 2 the concentration dependent binding of antibody 0018 towards differently aggregated forms of human alpha-synuclein is shown. The oligomer binding character becomes apparent below 0.5 µg/ml antibody concentration. The antibody 0018 is a chimeric antibody with variable domains of a rabbit antibody 064 selected by the procedure as outlined before and murine constant regions.

Upon using N-terminally modified peptides for the determination of the binding site of antibody 0018 on human alpha-synuclein no binding could be detected. Therefore the epitope analysis of antibody 0018 was carried out by means of a library of overlapping, immobilized peptide fragments (length: 15 amino acids, shift: I amino acids) corresponding to the sequences of α-Synuclein (1-140), β-Synuclein (60-

Figure 13:
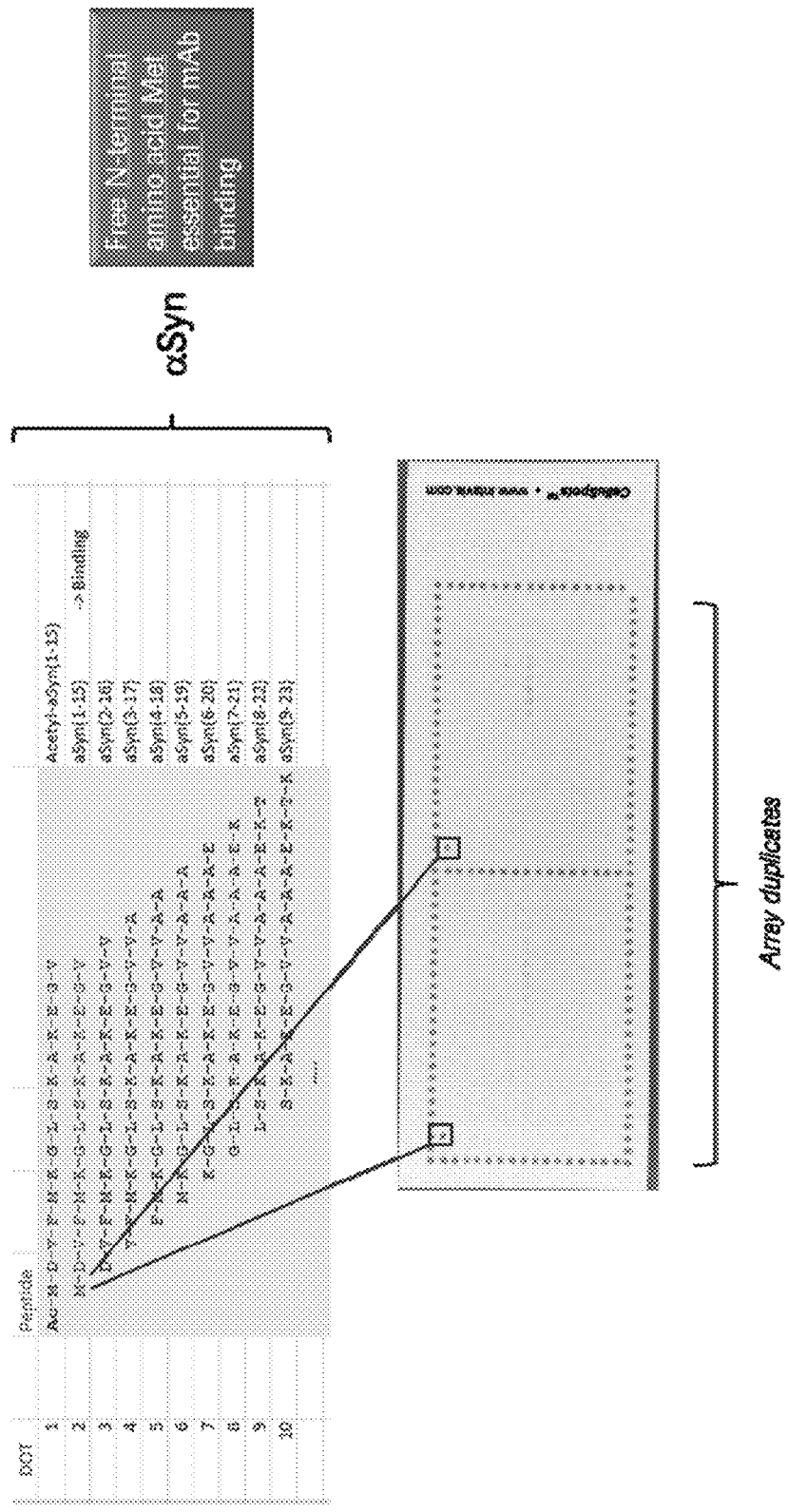
FIG. 13: CelluSpots™ epitope mapping of antibody 0018.

134), γ-Synuclein (60-127) and N-acetylated α-Synuclein peptide (1-15), and employing an ELISA-based detection method (see Example 14 and FIG. 13).

Figure 14:
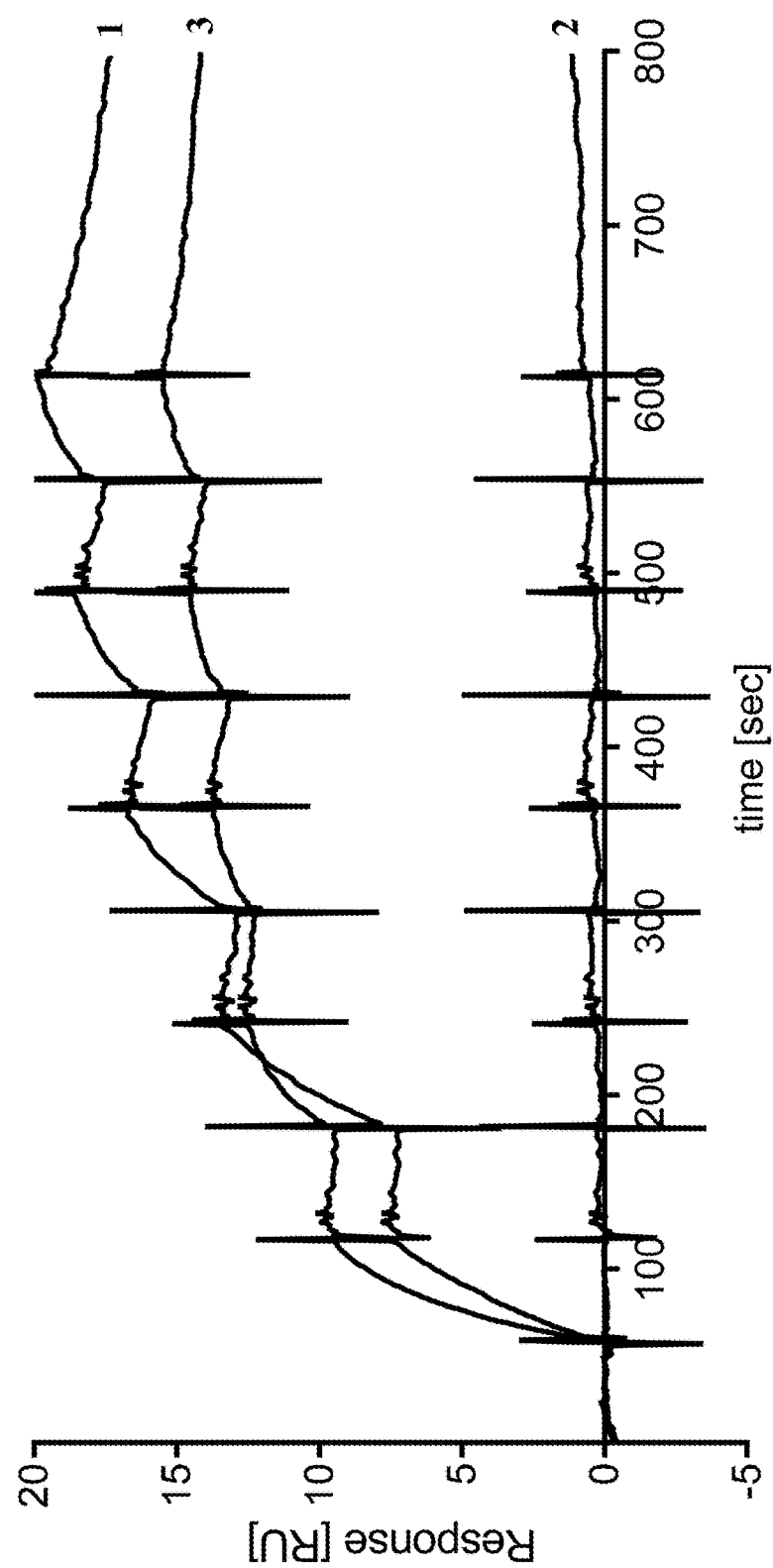
FIG. 14: Binding of monomeric (N-terminally free (1) and N-terminally His-tagged (2)) and dimeric (3) alpha-synuclein to antibody 0018. The results shown are a titration of 5 concentrations.

It has been found that antibody 0018 binds to a short (15 amino acids length) monomeric alpha-synuclein peptide presented on the peptide array. Antibody 0018 recognizes an epitope at the utmost N-terminus of alpha-synuclein. The N-terminal amino acid methionine (M, MET) is essential for binding, as removing (or blocking) thereof completely abolishes antibody 0018 binding. Further when the N-terminal methionine amino acid residue is capped by N-acetylation no binding can be observed. This is confirmed by surface plasmon resonance analysis (see FIG. 14).

Figure 3:
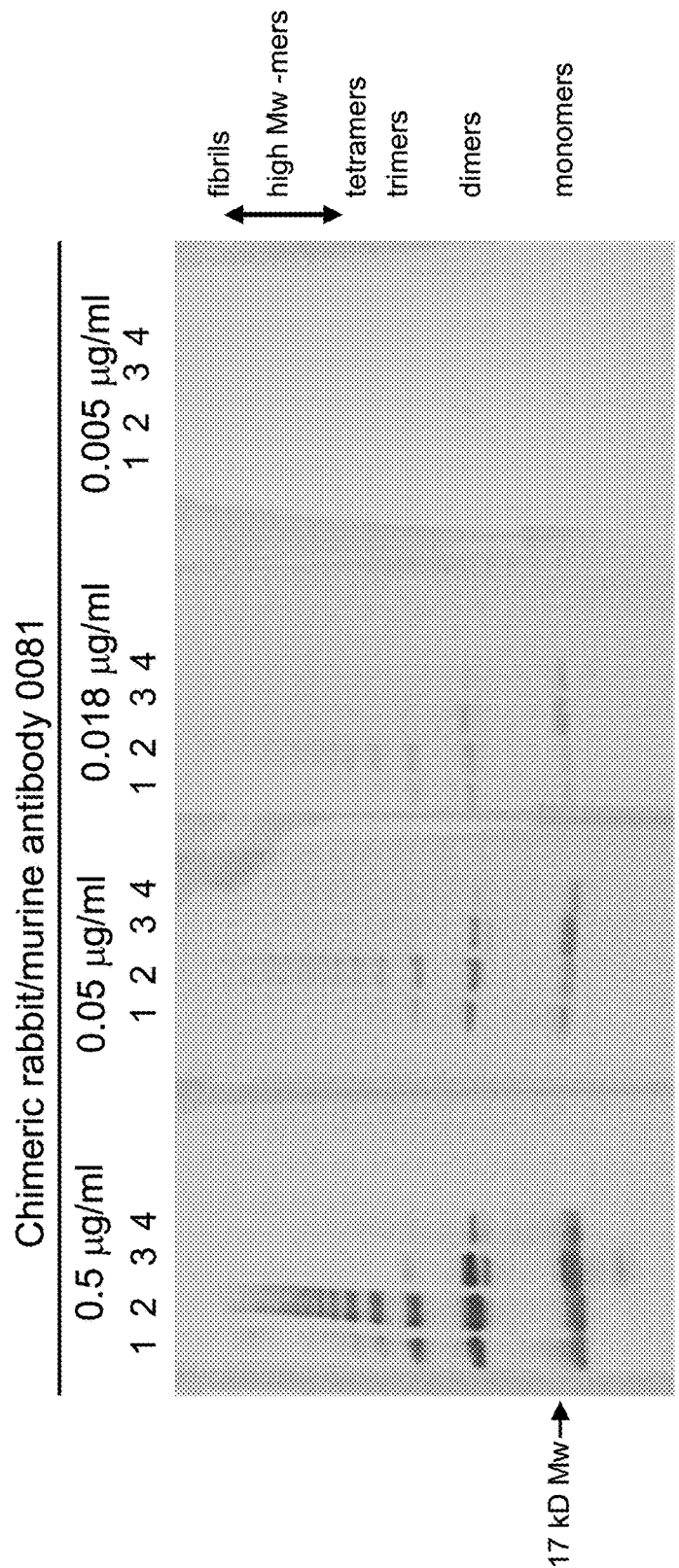
FIG. 3: Concentration dependent binding specificity of anti-alpha-synuclein-antibody 0081; Lane: 1) fibrillar alpha-synuclein preparation, 2) triple-proline mutant alpha-synuclein oligomers, 3) type A alpha-synuclein oligomers, 4) type C alpha-synuclein oligomers.

Another preferred antibody is the antibody 0081. The anti-alpha synuclein-antibody 0081 shows a dose-dependent reactivity pattern reminiscent of antibody 0018 with equal reduction of immunoreactivity for all forms of alpha-synuclein on the blot (FIG. 3).

Figure 4:
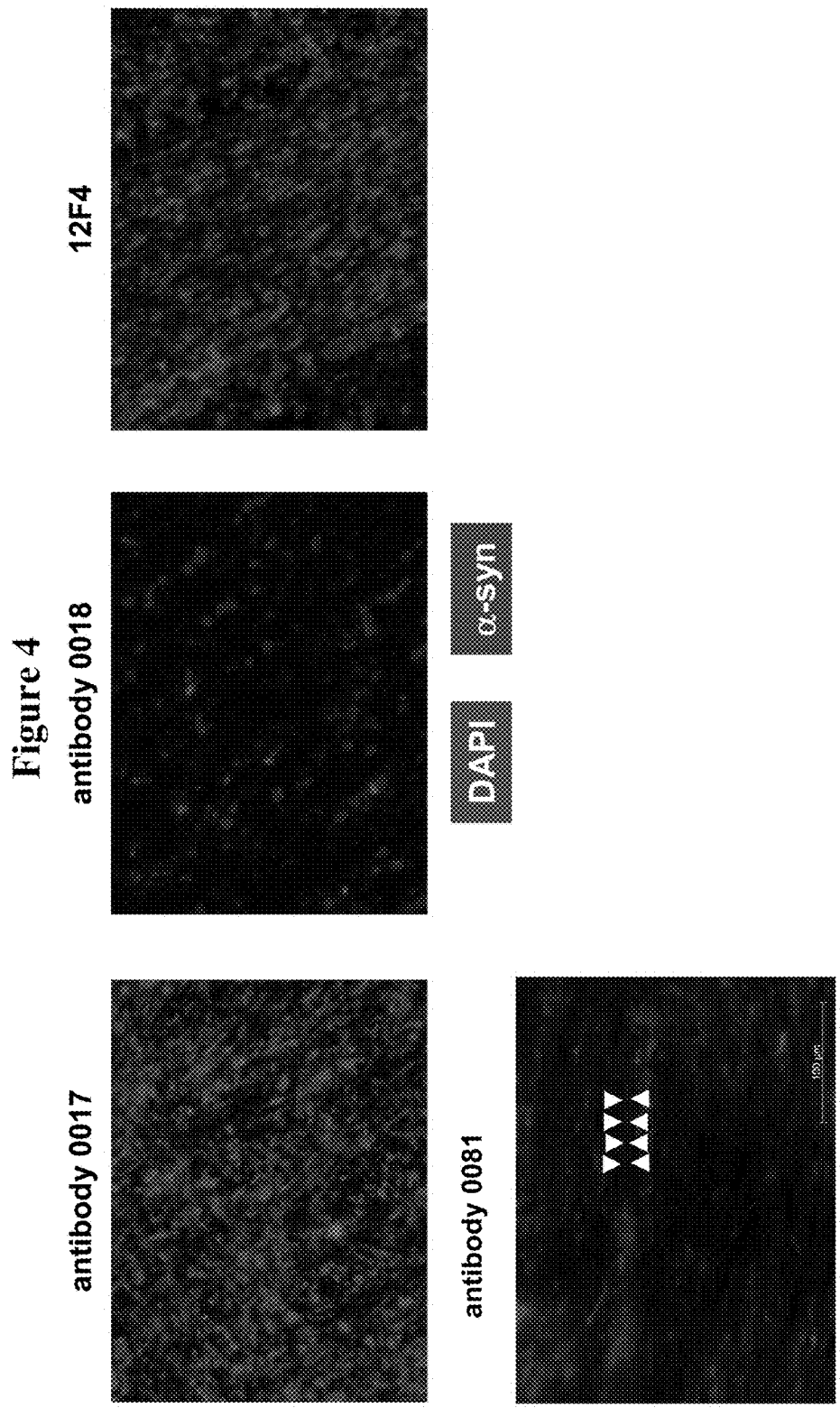
FIG. 4: Alpha-synuclein staining in brain stem of an alpha-synuclein[A30P]-transgenic mouse; Fresh frozen 10 µm sagittal brain sections; 40× magnification; all images at identical illumination conditions; arrowheads indicate Lewy neurite-like inclusions.

In FIG. 4 the different staining behavior of antibodies 0017 and 0018 and reference antibody 12F4 in sagittal brain sections of alpha-synuclein mutant A30P transgenic mouse is shown.

Figure 5:
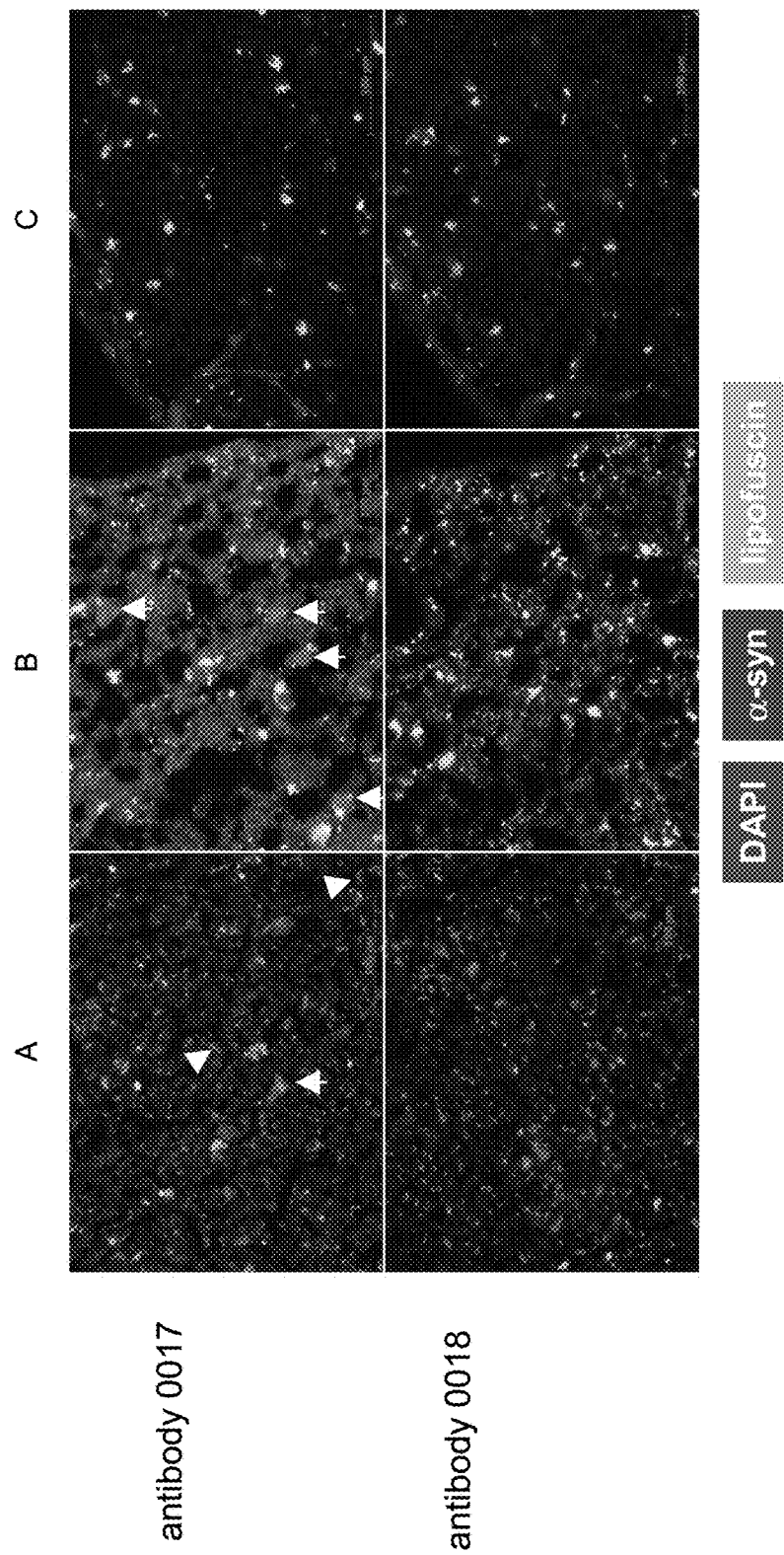
FIG. 5: Staining of antibodies 0017 and 0018 in human brain cortex of a Parkinson's Disease patient (A), an Alzheimer's Disease patient with Parkinson's Disease comorbidity (B) and progressive supranuclear palsy (PSP, tauopathy) (C); arrow: Lewy-body like inclusions; arrowhead: Lewy neurite-like inclusions.

In FIG. 5 the different staining behavior of antibodies 0017 and 0018 in human brain cortex of a Parkinson's Disease patient (A), an Alzheimer's Disease patient with Parkinson's Disease comorbidity (B) and progressive supranuclear palsy (C) is shown. The application of antibody 0017 resulted in a diffuse parenchymal as well as Lewy body and Lewy neurite staining. Antibody 0018 shows a weaker parenchymal staining and mostly stains Lewy bodies and Lewy neurites. Thus, antibodies 0017 and 0018 show different staining pattern for alpha-synuclein aggregates in brain sections of Parkinson's Disease patients.

Figure 6:
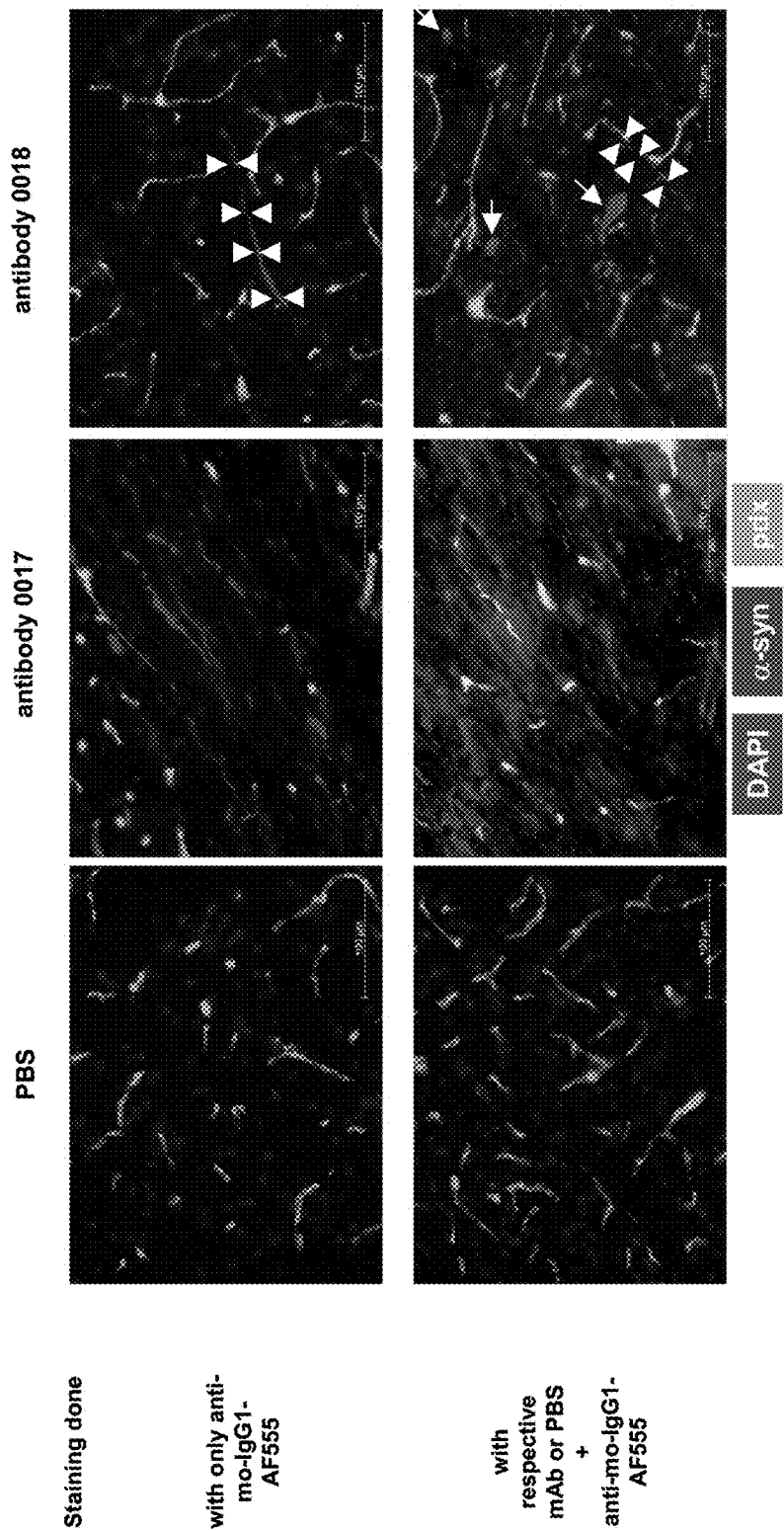
FIG. 6: Labeling of cerebral alpha-synuclein pathology in alpha-synuclein mutant A30P transgenic mice upon acute peripheral injection of specific mAbs (2×60 mg/kg antibody or PBS for 5 d) into 15 month old alpha-synuclein mutant A30P transgenic mice; Fresh frozen 20 µm sagittal brain sections were stained with anti-murine IgG1-antibody-AF555 conjugate or with the respective anti-alpha-synuclein antibody and anti-murine IgG1-antibody-AF555 conjugate; 40× magnification of brain stem region; all images at comparable illumination; arrow: Lewy-body like inclusions; arrowhead: Lewy neurite-like inclusions.

In FIG. 6 the labeling of cerebral alpha-synuclein pathology in alpha-synuclein mutant A30P transgenic mice upon acute peripheral injection of specific mAbs is shown. Anti-alpha synuclein antibody (2×60 mg/kg for 5 d) or PBS was applied to 15 month old alpha-synuclein mutant A30P transgenic mice. Fresh frozen 20 μm sagittal brain sections were stained with anti-murine IgG1-antibody-AF555 conjugate or with the respective anti-alpha-synuclein antibody and anti-murine IgG1-antibody-AF555 conjugate.

Figure 7A:
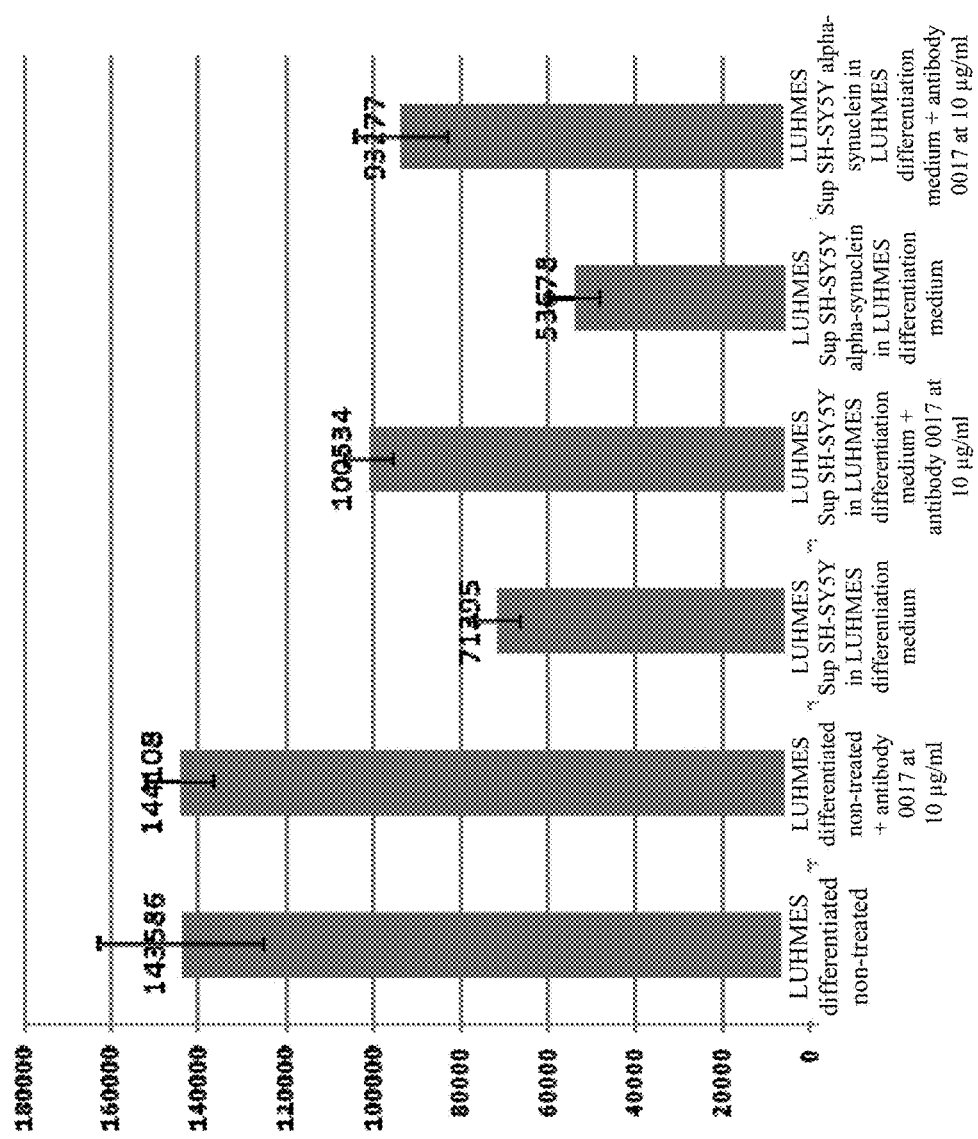
FIGS. 7A-7C: Cellular toxicity of conditioned media from recombinant alpha-synuclein from SHSY5Y cells on LUHMES cells.
Figure 7B:
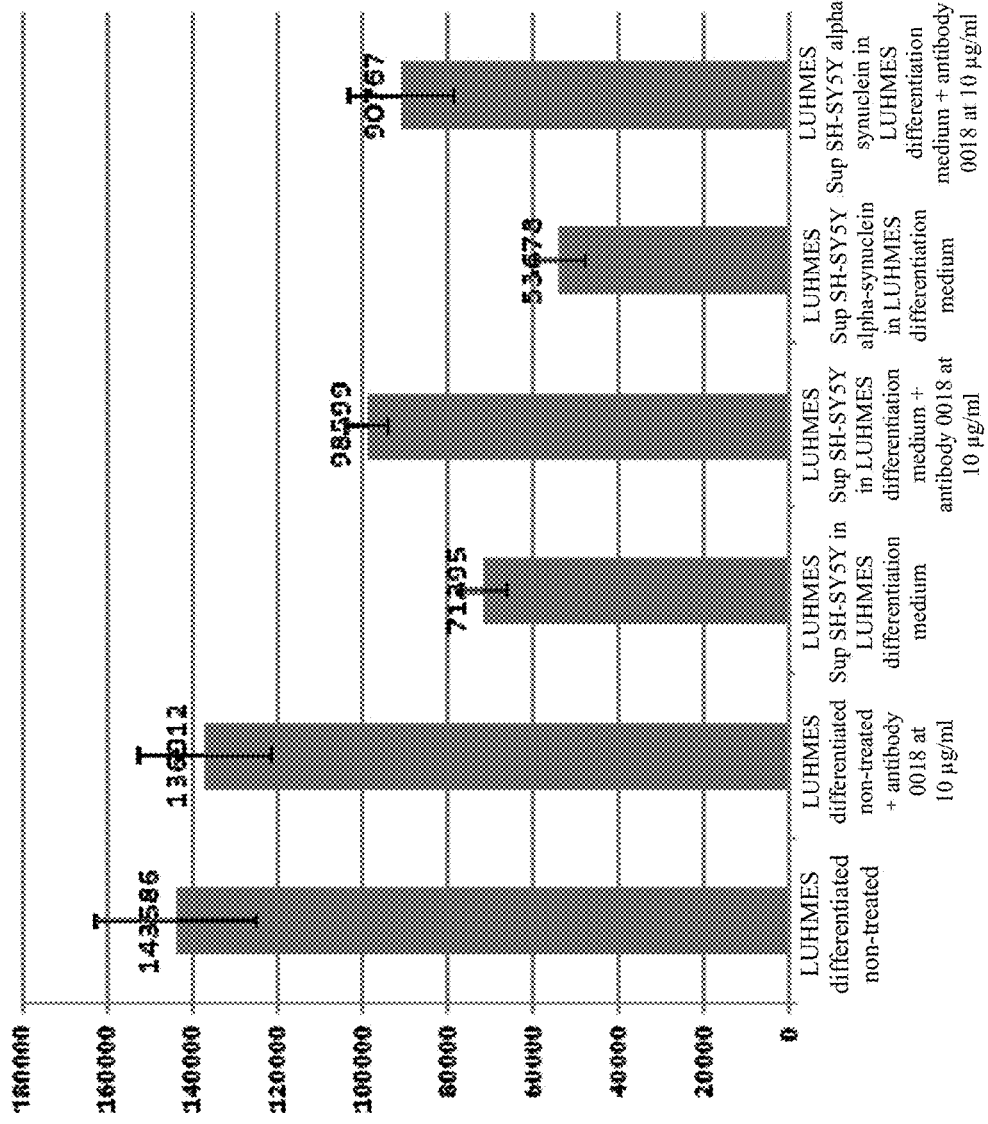
Figure 7C:
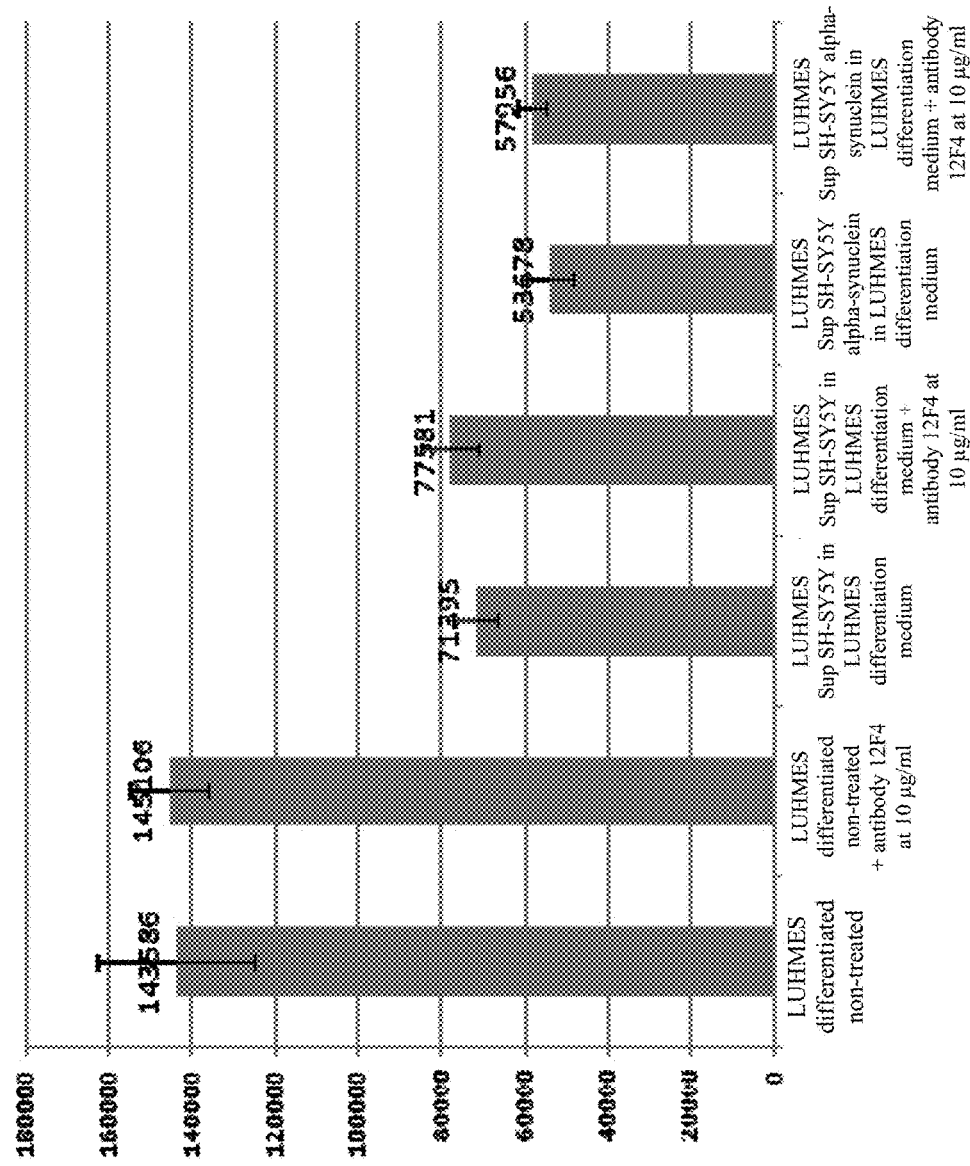
Figure 8:
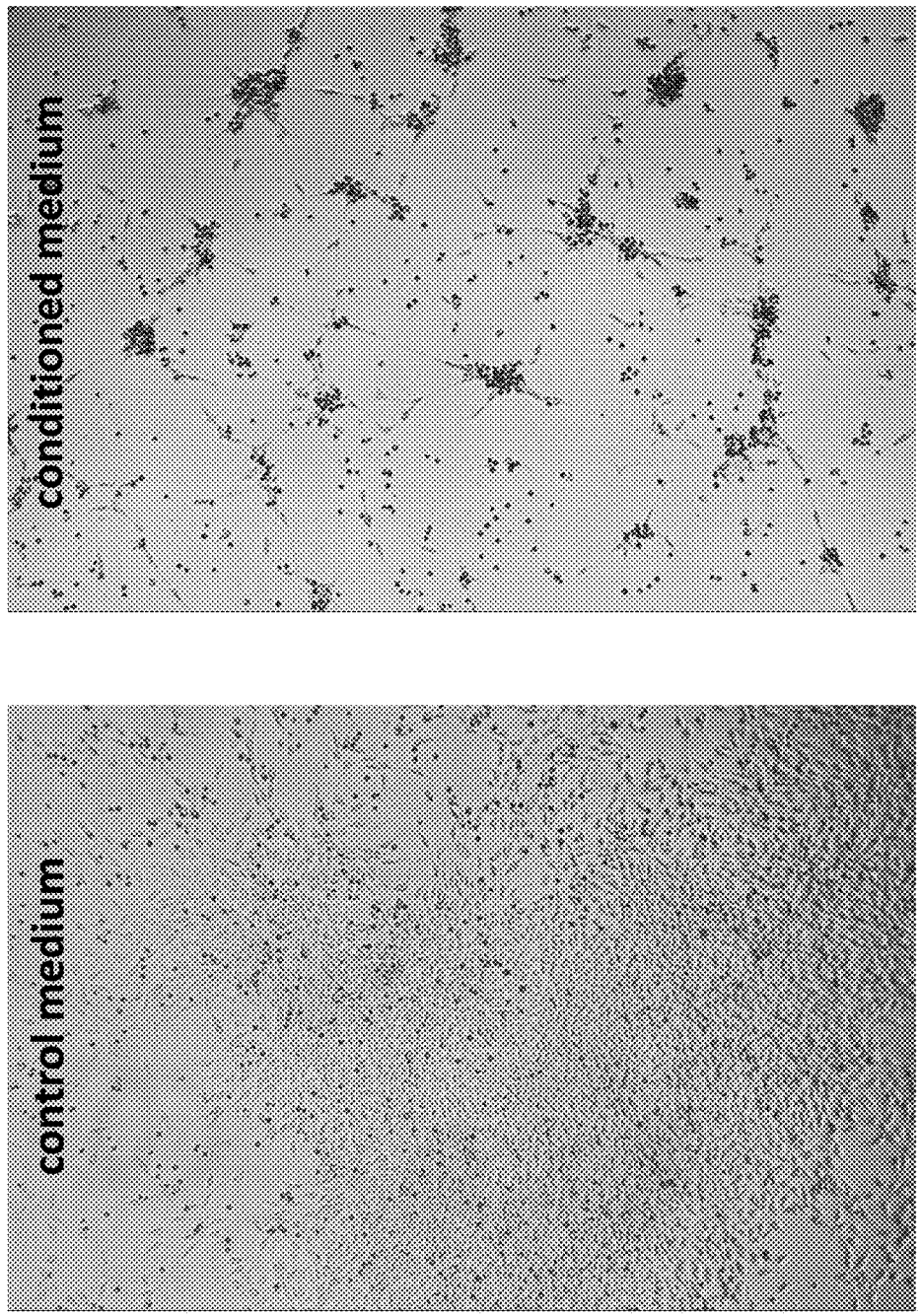
FIG. 8: Treatment of LUHMES cells with conditioned media from recombinantly alpha-synuclein expressing SHSY5Y cells; 3 day treatment on freshly plated LUHMES cells with a) control medium=differentiation medium for LUHMES cells and b) conditioned medium=LUHMES differentiation medium harvested after 6 days from recombinantly alpha-synuclein expressing SHSY5Y cells.

From FIGS. 7A-7C it can be seen that antibodies 0017 and 0018 are able to immunodeplete alpha-synuclein oligomers from extracellular media and thereby these antibodies reduce toxicity of alpha-synuclein oligomers.

In one aspect, the invention provides isolated antibodies that bind to human alpha-synuclein. In certain embodiments, the anti-human alpha-synuclein antibody:
  binds to a peptide that has the amino acid sequence of SEQ ID NO: 01 and binds to monomeric but not to fibrillar alpha-synuclein, or
  binds to the same epitope as an antibody that has a pair of variable domains of SEQ ID NO: 26 and 27 or SEQ ID NO: 38 and 39 and binds to fibrillar alpha-synuclein but not to monomeric alpha-synuclein,
  inhibits alpha-synuclein induced toxicity in neurons and glia cells,
  inhibits cell-to-cell transmission of alpha-synuclein aggregation,
  reduces alpha-synuclein induced caspase activity (e.g. in LUHMES cells).

In one aspect, the invention provides an anti-human alpha-synuclein antibody comprising at least one, or two, or three, or four, or five, or six HVRs selected from (a) HVR-H1 comprising the amino acid sequence of SEQ ID NO: 02; (b) HVR-H2 comprising the amino acid sequence of SEQ ID NO: 03; (c) HVR-H3 comprising the amino acid sequence of SEQ ID NO: 04; (d) HVR-L1 comprising the amino acid sequence of SEQ ID NO: 05; (e) HVR-L2 comprising the amino acid sequence of SEQ ID NO: 06; and (f) HVR-L3 comprising the amino acid sequence of SEQ ID NO: 07.

In one aspect, the invention provides an anti-human alpha-synuclein antibody comprising at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 04; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12.

In one aspect, the invention provides an anti-human alpha-synuclein antibody comprising at least one, or two, or three, or four, or five, or six HVRs selected from (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 17; (d) HVR-L1 comprising the amino acid sequence of SEQ ID NO: 18; (e) HVR-L2 comprising the amino acid sequence of SEQ ID NO: 19; and (f) HVR-L3 comprising the amino acid sequence of SEQ ID NO: 20.

In one aspect, the invention provides an anti-human alpha-synuclein antibody comprising at least one, or two, or three, or four, or five, or six HVRs selected from (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 17; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In one aspect, the invention provides an anti-human alpha-synuclein antibody comprising at least one, or two, or three, or four, or five, or six HVRs selected from (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33.

In one aspect, the invention provides an anti-human alpha-synuclein antibody comprising at least one, or two, or three, or four, or five, or six HVRs selected from (a) HVR-H1 comprising the amino acid sequence of SEQ ID NO: 28; (b) HVR-H2 comprising the amino acid sequence of SEQ ID NO: 34; (c) HVR-H3 comprising the amino acid sequence of SEQ ID NO: 30; (d) HVR-L1 comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

In one aspect, the invention provides an antibody comprising at least one, at least two, or all three VH HVR sequences selected from
i) (a) HVR-H1 comprising the amino acid sequence of SEQ ID NO: 02; (b) HVR-H2 comprising the amino acid sequence of SEQ ID NO: 03; and (c) HVR-H3 comprising the amino acid sequence of SEQ ID NO: 04; or ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 04, or iii) (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17, or iv) (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 17, or v) (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30, or vi) (a) HVR-H1 comprising the amino acid sequence of SEQ ID NO: 28; (b) HVR-H2 comprising the amino acid sequence of SEQ ID NO: 34; and (c) HVR-H3 comprising the amino acid sequence of SEQ ID NO: 30.

In one embodiment, the antibody comprises i) (a) HVR-H1 comprising the amino acid sequence of SEQ ID NO: 02; (b) HVR-H2 comprising the amino acid sequence of SEQ ID NO: 03; and (c) HVR-H3 comprising the amino acid sequence of SEQ ID NO: 04; or ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 04, or iii) (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17, or iv) (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 17, or v) (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30, or vi) (a) HVR-H1 comprising the amino acid sequence of SEQ ID NO: 28; (b) HVR-H2 comprising the amino acid sequence of SEQ ID NO: 34; and (c) HVR-H3 comprising the amino acid sequence of SEQ ID NO: 30.

In another embodiment the antibody further comprises at least one, at least two, or all three VL HVR sequences selected from i) (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07; or ii) (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12, or iii) (a) HVR-L1 comprising the amino acid sequence of SEQ ID NO: 18; (b) HVR-L2 comprising the amino acid sequence of SEQ ID NO: 19; and (c) HVR-L3 comprising the amino acid sequence of SEQ ID NO: 20, or iv) (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25, or v) (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33, or vi) (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37.

In a further embodiment, the antibody comprises i) (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07; or ii) (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12, or iii) (a) HVR-L1 comprising the amino acid sequence of SEQ ID NO: 18; (b) HVR-L2 comprising the amino acid sequence of SEQ ID NO: 19; and (c) HVR-L3 comprising the amino acid sequence of SEQ ID NO: 20, or iv) (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25, or v) (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33, or vi) (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37.

In one aspect, the invention provides an antibody comprising i) (a) HVR-H1 comprising the amino acid sequence of SEQ ID NO: 02; (b) HVR-H2 comprising the amino acid sequence of SEQ ID NO: 03; (c) HVR-H3 comprising the amino acid sequence of SEQ ID NO: 04; (d) HVR-L1 comprising the amino acid sequence of SEQ ID NO: 05; (e) HVR-L2 comprising the amino acid sequence of SEQ ID NO: 06; and (f) HVR-L3 comprising the amino acid sequence of SEQ ID NO: 07, or ii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 04; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, or iii) (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 17; (d) HVR-L1 comprising the amino acid sequence of SEQ ID NO: 18; (e) HVR-L2 comprising the amino acid sequence of SEQ ID NO: 19; and (f) HVR-L3 comprising the amino acid sequence of SEQ ID NO: 20, or iv) (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 17; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25, or v) (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33, or vi) (a) HVR-H1 comprising the amino acid sequence of SEQ ID NO: 28; (b) HVR-H2 comprising the amino acid sequence of SEQ ID NO: 34; (c) HVR-H3 comprising the amino acid sequence of SEQ ID NO: 30; (d) HVR-L1 comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

In any of the above embodiments, the anti-alpha synuclein antibody is humanized. In one embodiment, an anti-human alpha-synuclein antibody comprises HVRs as in any of the above embodiments, and further comprises an acceptor human framework, e.g. a human immunoglobulin framework or a human consensus framework.

In another embodiment the VH or VL contains substitutions (e.g., conservative substitutions), insertions, or deletions relative to the reference sequence, but an anti-human alpha-synuclein antibody comprising that sequence retains the ability to bind to human alpha-synuclein.

In certain embodiments, a total of 1 to 3 amino acids have been substituted, inserted and/or deleted in each of the HVR sequences as described herein before.

In a further aspect, the invention provides an antibody that binds to the same epitope as an anti-human alpha-synuclein antibody provided herein.

For example, in certain embodiments, an antibody is provided that binds to the same epitope as an anti-human alpha-synuclein antibody comprising a) a VH sequence of SEQ ID NO: 13 and a VL sequence of SEQ ID NO: 14, or b) a VH sequence of SEQ ID NO: 26 and a VL sequence of SEQ ID NO: 27, or c) a VH sequence of SEQ ID NO: 38 and a VL sequence of SEQ ID NO: 39.

In certain embodiments, an antibody is provided that binds to an epitope within a fragment of human alpha-synuclein consisting of amino acids 101-111 of SEQ ID NO: 40.

In certain embodiments, an antibody is provided that binds to a free N-terminal epitope (free N-terminal methionine residue) within a fragment of human alpha-synuclein consisting of amino acids 1-15 of SEQ ID NO: 40.

In one embodiment an antibody is provided that bind to human alpha-synuclein that has a free N-terminal methionine residue and that binds to a conformational epitope within residues 1 to 15 and 188-195 of human alpha-synuclein.

In a further aspect of the invention, an anti-human alpha-synuclein antibody according to any of the above embodiments is a monoclonal antibody, including a chimeric, humanized or human antibody. In one embodiment, an anti-human alpha-synuclein antibody is an antibody fragment, e.g., a Fv, Fab, Fab', scFv, diabody, or F(ab')2 fragment. In another embodiment, the antibody is a full length antibody, e.g., an intact IgG1 or IgG4 antibody or other antibody class or isotype as defined herein.

In a further aspect, an anti-human alpha-synuclein antibody according to any of the above embodiments may incorporate any of the features, singly or in combination, as described in Sections 1-7 below:

1. Antibody Affinity

In certain embodiments, an antibody provided herein has a dissociation constant (Kd) of ≤100 nM, ≤10 nM, ≤1 nM, or between 1 nM and 100 nM (e.g. $10^{-7}$ M or less, e.g. from $10^{-7}$ M to $10^{-9}$ M).

In one embodiment, Kd is measured by a radiolabeled antigen binding assay (RIA). In one embodiment, an RIA is performed with the Fab version of an antibody of interest and its antigen. For example, solution binding affinity of FABs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 g/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached.

Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes.

Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds 106 $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. No. 5,571,894 and U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. No. 5,821,337, U.S. Pat. No. 7,527,791, U.S. Pat. No. 6,982,321, and U.S. Pat. No. 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. No. 6,075,181 and U.S. Pat. No. 6,150,584 describing XENOMOUSE™ technology; U.S. Pat. No. 5,770,429 describing HuMab® technology; U.S. Pat. No. 7,041,870 describing K-M MOUSE® technology, and US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for human alpha-synuclein and the other is for any other antigen. In certain embodiments, bispecific antibodies may bind to two different epitopes of human alpha-synuclein. Bispecific antibodies may also be used to localize cytotoxic agents to cells which express human alpha-synuclein. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to human alpha-synuclein as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc☐RI, Fc☐RII and Fc☐RIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361).

Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371, 826).

See also Duncan, A. R. and Winter, G., Nature 322 (1988) 738-740; U.S. Pat. No. 5,648,260; U.S. Pat. No. 5,624,821; and WO 94/29351 concerning other examples of F-region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

f) Fusions with a Blood-Brain-Barrier Shuttle Module

Monoclonal antibodies have vast therapeutic potential for treatment of neurological or central nervous system (CNS) diseases, but their passage into the brain is restricted by the blood-brain-barrier (BBB). Past studies have shown that a very small percentage (approximately 0.1%) of an IgG circulating in the bloodstream crosses through the BBB into the CNS (Felgenhauer, K., Klin. Wschr. 52 (1974) 1158-1164), where the CNS concentration of the antibody may be insufficient to permit a robust effect.

In certain embodiments, an antibody provided herein may be further modified to contain one or more blood-brain-barrier shuttle modules that are known in the art and readily available.

The one or more blood-brain-barrier shuttle module can be fused to any terminus of the light or heavy chain. In one preferred embodiment the blood-brain-barrier shuttle module is fused to the C-terminus of the heavy chain.

The C-terminus of the heavy chain can be a complete C-terminus ending with the amino acid residues PGK. The C-terminus of the heavy chain can be a shortened C-terminus in which one or two of the C-terminal amino acid residues have been removed. In one preferred embodiment the C-terminus of the heavy chain is a shortened C-terminus ending PG.

The one or more blood-brain-barrier shuttle modules can be fused to the respective antibody chain either directly or via linker peptide. In one preferred embodiment the linker peptide has the amino acid sequence GGSGGGGSGGGGSGGGGS (SEQ ID NO: 41).

The blood-brain-barrier shuttle module can be an antibody scFv fragment. In one embodiment the blood-brain-barrier shuttle module is a scFv comprising in N- to C-terminal order a light chain variable domain—a light chain constant domain—a linker peptide—a heavy chain variable domain—the heavy chain constant domain 1.

In one preferred embodiment the blood-brain-barrier shuttle module is the scFv fragment of the anti-transferrin receptor-antibody 8D3 with a $(G4S)_6$ linker peptide or a humanized variant thereof.

The term humanized variant thereof denotes a molecule that has been obtained by grafting the CDRs of the murine 8D3 antibody on a human framework with the optional introduction of one to three mutations independently of each other in each of the framework regions (FRs) and/or the hypervariable regions (HVRs).

In one aspect, the present invention provides an anti-human alpha-synuclein antibody fusion polypeptide comprising an anti-human alpha-synuclein antibody, two peptide linker and two monovalent binding entities which bind to a blood-brain-barrier receptor, wherein the linker couples the anti-human alpha-synuclein antibody to the monovalent binding entities which bind to the blood-brain-barrier receptor.

In one aspect, the present invention provides an anti-human alpha-synuclein antibody fusion polypeptide comprising an anti-human alpha-synuclein antibody, a peptide linker and one monovalent binding entity which binds to a blood-brain-barrier receptor, wherein the linker couples the anti-human alpha-synuclein antibody to the monovalent binding entity which bind to the blood-brain-barrier receptor.

In one embodiment, the monovalent binding entity which binds to the blood-brain-barrier receptor is selected from the group consisting of proteins, polypeptides and peptides.

In one embodiment, the monovalent binding entity which binds to the blood-brain-barrier receptor comprises a molecule selected from the group consisting of a blood-brain-barrier receptor ligand, a scFv, an Fv, a scFab, a VHH, in one preferred embodiment a scFv or a scFab.

In one embodiment, the blood-brain-barrier receptor is selected from the group consisting of transferrin receptor, insulin receptor, insulin-like growth factor receptor, low density lipoprotein receptor-related protein 8, low density lipoprotein receptor-related protein 1 and heparin-binding epidermal growth factor-like growth factor. In one preferred embodiment the blood-brain-barrier receptor is the transferrin receptor.

In one embodiment, the monovalent binding entity which binds to the blood-brain-barrier receptor comprises one scFab or one scFv directed to the transferrin receptor, more particular a scFab or scFv recognizing an epitope in the transferrin receptor comprised within the amino acid sequence of SEQ ID NO: 52, 53 and 54.

In one embodiment, the monovalent binding entity which binds to the blood-brain-barrier receptor is coupled to the C-terminal end of the heavy chain of the anti-human alpha-synuclein antibody by the linker.

In one embodiment, the peptide linker is an amino acid sequence with a length of at least 15 amino acids, more preferably with a length of 18 to 25 amino acids.

In one embodiment, the anti-human alpha-synuclein antibody is a full length antibody, in one preferred embodiment a full length IgG. The term full length antibody denotes an antibody consisting of two antibody light chain polypeptides and two antibody heavy chain polypeptides wherein in the two antibody heavy chain polypeptides the C-terminal lysine residue (K) can be present or not.

In one preferred embodiment, the anti-human alpha-synuclein antibody fusion polypeptide comprises a full length IgG anti-human alpha-synuclein antibody as brain effector entity, a linker of the sequence GGSGGGGSGGGGSGGGGS (SEQ ID NO: 41) and one scFab as monovalent binding entity which binds to the human transferrin receptor as blood brain receptor, wherein the scFab is coupled by the linker to the C-terminal end (of the Fc part) of one of the heavy chains of the full length anti-human alpha-synuclein antibody, and wherein the scFab recognizes an epitope in the human transferrin receptor comprised within the amino acid sequence of SEQ ID NO: 52, 53 and 54.

In one preferred embodiment, the anti-human alpha-synuclein antibody fusion polypeptide comprises a full length IgG anti-human alpha-synuclein antibody as brain effector entity, a linker of the sequence GGSGGGGSGGGGSGGGGS (SEQ ID NO: 41) and one scFv as monovalent binding entity which binds to the human transferrin receptor as blood brain receptor, wherein the scFab is coupled by the linker to the C-terminal end (of the Fc part) of one of the heavy chains of the full length anti-human alpha-synuclein antibody, and wherein the scFab recognizes an epitope in the human transferrin receptor comprised within the amino acid sequence of SEQ ID NO: 52, 53 and 54.

In one embodiment, the first heavy chain of the anti-human alpha-synuclein antibody comprises a first dimerization module and the second heavy chain of the antibody comprises a second dimerization module allowing heterodimerization of the two heavy chains.

In one embodiment, the first dimerization module of the first heavy chain of the anti-human alpha-synuclein antibody is a knob heavy chain and the dimerization module of the second heavy chain of the anti-human alpha-synuclein antibody is a hole heavy chain (according to the knobs-into-holes strategy).

The anti-human alpha-synuclein antibody fusion polypeptide as reported herein can be used as a medicament, in particular it can be used for the treatment of a neurological disorder such as e.g. Parkinson's Disease.

The anti-human alpha-synuclein antibody fusion polypeptide as reported herein can be used to transport the anti-human alpha-synuclein antibody (brain effector entity) across the blood brain barrier.

In one embodiment, the heavy chain of the anti-human alpha-synuclein antibody that is coupled at its C-terminal end of the Fc-region to the scFab as monovalent binding entity which binds to the human transferrin receptor has the following structure in N- to C-terminal direction:
IgG heavy chain,
peptidic linker coupling the C-terminal end of the Fc-region of the IgG heavy chain to the N-terminal end of the VL domain of the scFab, in one preferred embodiment the peptidic linker has the amino acid sequence GGSGGGGSGGGGSGGGS (SEQ ID NO: 41),
variable light chain domain (VL) and C-kappa light chain domain of the scFab,
peptidic linker coupling the C-terminal end of the C-kappa light chain domain of the scFab to the N-terminal end of the VH domain of the scFab, in one preferred embodiment the peptidic linker has the amino acid sequence $(G_4S)_6GG$ (SEQ ID NO: 55),
variable heavy chain domain (VH) of the scFab antibody and IgG CH1 heavy chain domain.

In one embodiment, the heavy chain of the anti-human alpha-synuclein antibody that is coupled at its C-terminal end of the Fc-region to the scFv as monovalent binding entity which binds to the human transferrin receptor has the following structure in N- to C-terminal direction:
IgG heavy chain,
peptidic linker coupling the C-terminal end of the Fc part of the IgG heavy chain to the N-terminal end of the VL domain of the scFv antibody fragment, in one preferred embodiment the peptidic linker is a peptide with the amino acid sequence GGSGGGGSGGGGSGGGGS (SEQ ID NO: 41),
variable light chain domain (VL),
peptidic linker coupling the C-terminal end of the variable light chain domain to the N-terminal end of the VH domain of the scFv, in one preferred embodiment the peptidic linker is a peptide with the amino acid sequence $(G_4S)_6GG$ (SEQ ID NO: 55),
variable heavy chain domain (VH) of the scFv antibody fragment.

In a second aspect the present invention provides a fusion polypeptide to transport a brain effector entity across the blood-brain-barrier comprising a CH2-CH3 Ig entity, a peptidic linker and one scFab or scFv directed to a blood-brain-barrier receptor, wherein the scFab or scFv is coupled to a C-terminal end of the CH2-CH3 Ig entity by the peptidic linker.

In one embodiment the blood-brain-barrier shuttle module/the scFab or scFv directed to a blood-brain-barrier receptor is derived from a humanized anti-transferrin receptor antibody 8D3 (see e.g. Boado, R. J., et al., Biotechnol. Bioeng. 102 (2009) 1251-1258). The murine heavy chain variable domain has the amino acid sequence of (SEQ ID NO: 56)
EVQLVESGGG LVQPGNSLTL SCVASGFTFS NYGMHWIRQA

PKKGLEWIAM IYYDSSKMNY ADTVKGRFTI SRDNSKNTLY

LEMNSLRSED TAMYYCAVPT SHYVVDVWGQ GVSVTVSS.

The murine light chain variable domain (variant 1) has the amino acid sequence of (SEQ ID NO: 57)
DIQMTQSPAS LSASLEEIVT ITCQASQDIG NWLAWYQQKP

GKSPQLLIYG ATSLADGVPS RFSGSRSGTQ FSLKISRVQV

EDIGIYYCLQ AYNTPWTFGG GTKLELK,
and the murine light chain variable domain (variant 2) has the amino acid sequence of (SEQ ID NO: 58)
DIQMTQSPAS LSASLEEIVT ITCQASQDIG NWLAWYQQKP

GKSPQLLIYG ATSLADGVPS RFSGSRSGTQ FSLKISRVQV

EDIGIYYCLQ AYNTPWTFGG GTKVEIK.

One Blood-Brain-Barrier Shuttle Module

In one aspect the anti-human alpha synuclein antibody fusion polypeptide comprises exactly one blood-brain-barrier shuttle module, wherein the blood-brain-barrier shuttle module comprises the humanized variable domains of the murine anti-human transferrin receptor antibody 8D3, whereby the blood-brain-barrier shuttle module comprising the humanized variable domains of the murine anti-human transferrin receptor antibody 8D3 transports the anti-human alpha-synuclein antibody across the blood-brain-barrier. The variable domains of the anti-human transferrin receptor antibody 8D3 have the amino acid sequence of SEQ ID NO: 56 and 57.

One or Two Blood-Brain-Barrier Shuttle Modules

In one aspect the anti-human alpha synuclein antibody fusion polypeptide comprises one or two blood-brain-barrier shuttle module(s), wherein the blood-brain-barrier shuttle module derived from an antibody which binds with low affinity to a blood-brain-barrier receptor (BBB-R), whereby the blood-brain-barrier shuttle module derived from an antibody which binds with low affinity to a blood-brain-barrier receptor transports the anti-human alpha-synuclein antibody across the blood-brain-barrier.

In another aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). In another such aspect, the BBB-R is a human BBB-R. In one such aspect, the BBB-R is TfR. In another such aspect, the BBB-R is TfR and the antibody does not inhibit TfR activity. In another such aspect, the BBB-R is TfR and the antibody does not inhibit the binding of TfR to transferrin.

In another aspect, the antibody does not impair the binding of the BBB-R to one or more of its native ligands. In another such aspect, the antibody specifically binds to human transferrin receptor (hTfR) in such a manner that it does not inhibit binding of the hTfR to human transferrin.

In another aspect, the anti-BBB-R antibody has an $IC_{50}$ for the BBB-R from about 1 nM to about 100 μM. In another such aspect, the $IC_{50}$ is from about 5 nM to about 100 μM. In another such aspect, the $IC_{50}$ is from about 50 nM to about 100 μM. In another such aspect, the $IC_{50}$ is from about 100 nM to about 100 μM. In another aspect, the antibody has an affinity for the BBB-R from about 5 nM to about 10 μM. In another such aspect, the antibody, when couples to the anti-human alpha-synuclein antibody, has an affinity for the BBB-R from about 30 nM to about 1 μM. In another such aspect, the antibody, when coupled to the anti-human alpha-synuclein antibody, has an affinity for the BBB-R from about 50 nM to about 1 μM. In one aspect, the affinity of the anti-BBB-R antibody or the anti-human alpha-synuclein antibody fusion polypeptide for the BBB-R is measured using scatchard analysis. In another aspect, the affinity of the anti-BBB-R antibody or the anti-human alpha-synuclein antibody fusion polypeptide for the BBB-R is measured using BIACORE analysis. In another aspect, the affinity of the anti-BBB-R antibody or the anti-human alpha-synuclein antibody fusion polypeptide for the BBB-R is measured using a competition ELISA.

Use of the Blood-Brain-Barrier Shuttle Containing Antibody Fusion Polypeptides

In another embodiment, herein is provided a method of increasing exposure of the CNS to an anti-human alpha synuclein antibody, wherein the anti-human alpha synuclein antibody is coupled to an antibody or antibody fragment which binds with low affinity to a BBB-R, thereby increasing the exposure of the CNS to the anti-human alpha synuclein antibody. In another aspect, the increase in CNS exposure to the anti-human alpha synuclein antibody is measured relative to the CNS exposure of an anti-human alpha synuclein antibody coupled with a typical antibody not having lowered affinity for the BBB-R. In another aspect, the increase in CNS exposure to the anti-human alpha synuclein antibody is measured as a ratio of the amount of the anti-human alpha synuclein antibody found in the CNS relative to the amount found in the serum after administration. In another such aspect, the increase in CNS exposure results in a ratio of greater than 0.1%. In another aspect, the increase in CNS exposure to the anti-human alpha synuclein antibody is measured relative to the CNS exposure of the anti-human alpha synuclein antibody in the absence of a coupled anti-BBB-R antibody. In another aspect, the increase in CNS exposure to the anti-human alpha synuclein antibody is measured by imaging. In another aspect, the increase in CNS exposure to the anti-human alpha synuclein antibody is measured by an indirect readout such as a modification of one or more physiological symptoms.

A method of increasing retention in the CNS of an anti-human alpha synuclein antibody administered to a subject, wherein the anti-human alpha synuclein antibody is coupled to an antibody or antibody fragment, which binds with low affinity to a BBB-R, such that the retention in the CNS of the anti-human alpha synuclein antibody is increased.

In another embodiment, the invention provides a method of optimizing the pharmacokinetics and/or pharmacodynamics of an anti-human alpha synuclein antibody to be efficacious in the CNS of a subject, wherein the anti-human alpha synuclein antibody is coupled to an antibody or antibody fragment, which binds with low affinity to a BBB-R, whereby the antibody or antibody fragment is selected such that its affinity for the BBB-R after coupling to the anti-human alpha synuclein antibody results in an amount of transport of the antibody or antibody fragment conjugated to the anti-human alpha synuclein antibody across the BBB that optimizes the pharmacokinetics and/or pharmacodynamics of the anti-human alpha synuclein antibody in the CNS.

In another embodiment the invention provides a method of treating a neurological disorder in a mammal comprising treating the mammal with an antibody or antibody fragment, which binds a BBB-R and which is coupled to an anti-human alpha synuclein antibody, wherein the antibody has been selected to have a low affinity for the BBB-R and thereby improves CNS uptake of the antibody and coupled anti-human alpha synuclein antibody. In one embodiment, the treating results in lessening or elimination of disorder symptoms. In another aspect, the treating results in amelioration of the neurological disorder.

In one embodiment of all previous aspects, the anti-BBB-R antibody has an $IC_{50}$ for the BBB-R from about 1 nM to about 100 μM. In another such embodiment, the $IC_{50}$ is from about 5 nM to about 100 μM. In another such embodiment, the $IC_{50}$ is from about 50 nM to about 100 μM. In another such embodiment, the $IC_{50}$ is from about 100 nM to about 100 μM. In another embodiment, the antibody has an affinity for the BBB-R from about 5 nM to about 10 μM. In another embodiment, the antibody, when couples to the anti-human alpha-synuclein antibody, has an affinity for the BBB-R from about 30 nM to about 1 μM. In another embodiment, the antibody, when coupled to the anti-human alpha-synuclein antibody, has an affinity for the BBB-R from about 50 nM to about 1 μM. In one embodiment, the affinity of the anti-BBB-R antibody or the anti-human alpha-synuclein antibody fusion polypeptide for the BBB-R is measured using scatchard analysis. In another embodiment, the affinity of the anti-BBB-R antibody or the anti-human alpha-synuclein antibody fusion polypeptide for the BBB-R is measured using BIACORE analysis. In another embodiment, the affinity of the anti-BBB-R antibody or the anti-human alpha-synuclein antibody fusion polypeptide for the BBB-R is measured using a competition ELISA.

In another embodiment, the anti-human alpha synuclein antibody fusion polypeptide is labeled. In another embodiment, the anti-BBB-R antibody or fragment does not impair the binding of the BBB-R to one or more of its native ligands. In another embodiment, the anti-BBB-R antibody specifically binds to hTfR in such a manner that it does not inhibit binding of the hTfR to human transferrin. In another embodiment, the anti-human alpha synuclein antibody fusion polypeptide is administered to a mammal. In another embodiment, the mammal is a human. In another embodiment, the mammal has a neurological disorder. In another embodiment, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angehnlman's syndrome, Liddle syndrome, Parkinson's disease, Pick's disease, Paget's disease, cancer, and traumatic brain injury.

B. Recombinant Methods and Compositions

Antibodies may be produced using recombinant methods and compositions, e.g., as described in U.S. Pat. No. 4,816,567. In one embodiment, isolated nucleic acid encoding an anti-human alpha-synuclein antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-human alpha-synuclein antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human alpha-synuclein antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68;

MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-human alpha-synuclein antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, alphaLISA, Western blot, antibody or reverse phase array, etc.

In an exemplary ELISA or alphaLISA assay, alpha-synuclein in solution (cell supernatant, cell or tissue lysates, body fluids etc.) is bound by a capture antibody, which specifically binds to a first epitope on alpha-synuclein, or alpha-synuclein in a certain conformation and a detection antibody coupled to a detection entity, which specifically binds to a second epitope or conformation of alpha-synuclein. The readout is based on the detection entity (chemiluminescence, fluorescence, energy transfer induced luminescence etc.). In some instances the same antibody can be used in the same assay as capture and detection antibody to detect aggregated forms of alpha-synuclein (see e.g. Tokuda, T. et al., Neurology 75 (2010) 1766-1772).

In the case of antibody array, antibodies are spotted onto glass or nitrocellulose chips. The slides are blocked and incubated with alpha-synuclein containing solution, washed to remove unbound antibodies and bound antibodies are detected with a fluorescently labeled corresponding secondary antibody. The fluorescence signal is measured by a fluorescence slide scanner. Similarly for a reverse phase array, recombinant alpha-synuclein, cell supernatant, cell or tissue lysates, body fluids etc. are spotted onto glass or nitrocellulose chips. The slides are blocked and individual arrays are incubated with an antibody against a specific epitope on alpha-synuclein. Unbound antibodies are washed off and bound antibodies are detected with a fluorescently labeled corresponding secondary antibody. The fluorescence signal is measured by a fluorescence slide scanner (Dernick, G., et al., J. Lipid Res. 52 (2011) 2323-2331).

In the example of Western blot, aggregated recombinant alpha-synuclein or alpha-synuclein derived from cell supernatant, cell or tissue lysates, body fluids etc. is separated by molecular weight in SDS PAGE or native gel conditions and blotted onto a nitrocellulose or PVDF membrane. After blocking the membrane is incubated with antibodies specific to amino acid sequence or conformations of alpha-synuclein. Thereafter the membrane is washed to remove unbound antibody.

Bound antibodies are detected by corresponding secondary antibodies coupled to detection entities for chemiluminescence or fluorescence or other means of detection. Antibodies specific to amino acid sequences of alpha-synuclein will bind to alpha-synuclein in various aggregated forms and hence molecular weights as long as the epitope is not masked by the aggregation. On the other hand, conformation specific antibodies will detect only certain aggregated forms of alpha-synuclein revealing only bands at specific molecular weights (see e.g. Towbin, H., et al., Proc. Natl. Acad. Sci. USA 76 (1979) 4350-4353; Burnette, W. N., Anal. Biochem. 112 (1981) 195-203).

In another aspect, competition assays may be used to identify an antibody that competes with antibody 0017, antibody 0018 or antibody 0081 for binding to human alpha-synuclein. In certain embodiments, such a competing antibody binds to the same epitope (e.g., a linear or a conformational epitope) that is bound by an antibody as reported herein such as antibody 0017, antibody 0018 and antibody 0081. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996).

In an exemplary competition assay, immobilized human alpha-synuclein is incubated in a solution comprising a first labeled antibody that binds to human alpha-synuclein (e.g., antibody 0017, antibody 0018 or antibody 0081) and a second unlabeled antibody that is being tested for its ability to compete with the first antibody for binding to human alpha-synuclein. As a control, immobilized human alpha-synuclein is incubated in a solution comprising the first labeled antibody but not the second unlabeled antibody. After incubation under conditions permissive for binding of the first antibody to human alpha-synuclein, excess unbound antibody is removed, and the amount of label associated with immobilized human alpha-synuclein is measured. If the amount of label associated with immobilized human alpha-synuclein is substantially reduced in the test sample relative to the control sample, then that indicates that the second antibody is competing with the first antibody for binding to human alpha-synuclein (see e.g., Harlow, E. and Lane, D., Antibodies: A Laboratory Manual, Chapter 14, Cold Spring Harbor Laboratory, Cold Spring Harbor, N.Y. (1988)).

2. Activity Assays

In one aspect, assays are provided for identifying anti-human alpha-synuclein antibodies thereof having biological activity. Biological activity may include, e.g., protection from/reduction of/inhibition of alpha-synuclein induced cytotoxicity, and/or protection from/reduction of/inhibition of cell-to-cell transmission of oligomeric human alpha-synuclein, and/or reduction of alpha-synuclein-induced caspase activity in human neuronal cells. Antibodies having such biological activity in vivo and/or in vitro are also provided.

In certain embodiments, an antibody of the invention is tested for such biological activity.

The protective biological activity can be assessed by adding conditioned medium containing secreted alpha-synuclein, which causes cell death on recipient neuronal cells. This toxicity can be reversed by adding protective antibodies as described herein. The toxic nature of secreted alpha-synuclein has been established previously (Emmanouilidou, E., et al., J. Neurosci., 30 (2010) 6838-6851).

D. Methods and Compositions for Diagnostics and Detection

In certain embodiments, any of the anti-human alpha-synuclein antibodies provided herein is useful for detecting the presence of human alpha-synuclein in a biological sample. The term "detecting" as used herein encompasses quantitative or qualitative detection. In certain embodiments, a biological sample comprises a cell or tissue, such as brain tissue.

In one embodiment, an anti-human alpha-synuclein antibody for use in a method of diagnosis or detection is provided. In a further aspect, a method of detecting the presence of human alpha-synuclein in a biological sample is provided. In certain embodiments, the method comprises contacting the biological sample with an anti-human alpha-synuclein antibody as described herein under conditions permissive for binding of the anti-human alpha-synuclein antibody to human alpha-synuclein, and detecting whether a complex is formed between the anti-human alpha-synuclein antibody and human alpha-synuclein. Such method may be an in vitro or in vivo method. In one embodiment, an anti-human alpha-synuclein antibody is used to select subjects eligible for therapy with an anti-human alpha-synuclein antibody, e.g. where human alpha-synuclein is a biomarker for selection of patients.

Exemplary disorders that may be diagnosed using an antibody of the invention include neurodegeneration with brain iron accumulation type 1 (NBIA1), pure autonomic failure, Down's syndrome, complex of Guam, and several Lewy body disorders, such as diffuse Lewy body disease (DLBD), the Lewy body variant of Alzheimer's disease (LBVAD), certain forms of Gaucher's disease, and Parkinson's Disease dementia (PDD).

In certain embodiments, labeled anti-human alpha-synuclein antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

E. Pharmaceutical Formulations

Pharmaceutical formulations of an anti-human alpha-synuclein antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide [[list drugs that might be combined with the anti-human alpha-synuclein antibody]]. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

F. Therapeutic Methods and Compositions

Any of the anti-human alpha-synuclein antibodies provided herein may be used in therapeutic methods.

In one aspect, an anti-human alpha-synuclein antibody for use as a medicament is provided. In further aspects, an anti-human alpha-synuclein antibody for use in treating Parkinson's Disease is provided. In certain embodiments, an anti-human alpha-synuclein antibody for use in a method of treatment is provided. In certain embodiments, the invention provides an anti-human alpha-synuclein antibody for use in a method of treating an individual having Parkinson's Disease comprising administering to the individual an effective amount of the anti-human alpha-synuclein antibody. In one such embodiment, the method further comprises administering to the individual an effective amount of at least one additional therapeutic agent, e.g., as described below. In further embodiments, the invention provides an anti-human alpha-synuclein antibody for use in inhibiting alpha-synuclein induced cytotoxicity in human neurons and glia cells, or inhibiting cell-to-cell transmission of oligomeric human alpha-synuclein between neurons and glia cells, or reducing alpha-synuclein-induced caspase activity. In certain embodiments, the invention provides an anti-human alpha-synuclein antibody for use in a method of inhibiting alpha-synuclein induced cytotoxicity in human neurons and glia cells, or inhibiting cell-to-cell transmission of oligomeric human alpha-synuclein between neurons and glia cells, or reducing alpha-synuclein-induced caspase activity in an individual comprising administering to the individual an effective of the anti-human alpha-synuclein antibody to inhibit alpha-synuclein induced cytotoxicity in human neurons and glia cells, or inhibit cell-to-cell transmission of oligomeric human alpha-synuclein between neurons and glia cells, or reduce alpha-synuclein-induced caspase activity. An "individual" according to any of the above embodiments is preferably a human.

In a further aspect, the invention provides for the use of an anti-human alpha-synuclein antibody in the manufacture or preparation of a medicament. In one embodiment, the medicament is for treatment of Parkinson's Disease. In a further embodiment, the medicament is for use in a method of treating Parkinson's Disease comprising administering to an individual having Parkinson's Disease an effective amount of the medicament. In one such embodiment, the method further comprises administering to the individual an effective amount of at least one additional therapeutic agent, e.g., as described below. In a further embodiment, the medicament is for inhibiting alpha-synuclein induced cytotoxicity in human neurons and glia cells, or for inhibiting cell-to-cell transmission of oligomeric human alpha-synuclein between neurons and glia cells, or for reducing alpha-synuclein-induced caspase activity. In a further embodiment, the medicament is for use in a method of inhibiting alpha-synuclein induced cytotoxicity in human neurons and glia cells, or inhibiting cell-to-cell transmission of oligomeric human alpha-synuclein between neurons and glia cells, or reducing alpha-synuclein-induced caspase activity in an individual comprising administering to the individual an amount effective of the medicament to inhibit alpha-synuclein induced cytotoxicity in human neurons and glia cells, or to inhibit cell-to-cell transmission of oligomeric human alpha-synuclein between neurons and glia cells, or to reduce alpha-synuclein-induced caspase activity. An "individual" according to any of the above embodiments may be a human.

In a further aspect, the invention provides a method for treating Parkinson's Disease. In one embodiment, the method comprises administering to an individual having such Parkinson's Disease an effective amount of an anti-human alpha-synuclein antibody. In one such embodiment, the method further comprises administering to the individual an effective amount of at least one additional therapeutic agent, as described below. An "individual" according to any of the above embodiments may be a human.

In a further aspect, the invention provides a method for inhibiting alpha-synuclein induced cytotoxicity in human neurons and glia cells, or inhibiting cell-to-cell transmission of oligomeric human alpha-synuclein between neurons and glia cells, or reducing alpha-synuclein-induced caspase in an individual. In one embodiment, the method comprises administering to the individual an effective amount of an anti-human alpha-synuclein antibody to inhibit alpha-synuclein induced cytotoxicity in human neurons and glia cells, or to inhibit cell-to-cell transmission of oligomeric human alpha-synuclein between neurons and glia cells, or to reduce alpha-synuclein-induced caspase activity. In one embodiment, an "individual" is a human.

In a further aspect, the invention provides pharmaceutical formulations comprising any of the anti-human alpha-synuclein antibodies provided herein, e.g., for use in any of the above therapeutic methods. In one embodiment, a pharmaceutical formulation comprises any of the anti-human alpha-synuclein antibodies provided herein and a pharmaceutically acceptable carrier. In another embodiment, a pharmaceutical formulation comprises any of the anti-human alpha-synuclein antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-human alpha-synuclein antibody and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-human alpha-synuclein antibody.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-human alpha-synuclein antibody.

IV. Specific Embodiments

1. An antibody that specifically binds to human alpha-synuclein, wherein the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in LUHMES cells.
2. The antibody according to item 1, characterized in that the caspase activity is caspase 3 and/or caspase 7 activity.
3. The antibody according to any one of items 1 to 2, characterized in that the antibody is for use in the treatment of synucleinopathies.
4. The antibody according to item 3, characterized in that the antibody is for use in the treatment of Parkinson's Disease.
5. The antibody according to any one of items 1 to 4, characterized in that the antibody specifically binds to a peptide consisting of the amino acid sequence GKNEEGAPQEG (SEQ ID NO: 01).
6. The antibody according to any one of items 1 to 5, characterized in that the antibody has a binding affinity for monomeric human alpha-synuclein of less than 10E-09 M and more than 10E-07 M.
7. The antibody according to any one of items 1 to 6, characterized in that the antibody specifically binds to monomeric and oligomeric human alpha-synuclein and does not bind to fibrillar human alpha-synuclein.
8. The antibody according to any one of items 1 to 7, characterized in that the antibody comprises in the heavy chain variable domain the HVRs of SEQ ID NO: 02 to 04 and in the light chain variable domain the HVRs of SEQ ID NO: 05 to 07.
9. The antibody according to any one of items 1 to 7, characterized in that the antibody comprises in the heavy chain variable domain the HVRs of SEQ ID NO: 08, 09 and 04 and in the light chain variable domain the HVRs of SEQ ID NO: 10 to 12.
10. The antibody according to any one of items 8 to 9, characterized in that the antibody comprises a heavy chain variable domain consisting of SEQ ID NO: 13 and a light chain variable domain consisting of SEQ ID NO: 14.
11. The antibody according to any one of items 1 to 10, characterized in that the antibody has been obtained by humanizing an antibody comprising a heavy chain variable domain consisting of SEQ ID NO: 13 and a light chain variable domain consisting of SEQ ID NO: 14.
12. The antibody according to any one of items 1 to 7, characterized in that the antibody is a humanized antibody and comprises in the heavy chain variable domain the HVRs of SEQ ID NO: 02 to 04 and in the light chain variable domain the HVRs of SEQ ID NO: 05 to 07, wherein in each HVR up to 3 amino acid residues can be changed.
13. The antibody according to any one of items 1 to 7, characterized in that the antibody is a humanized antibody and comprises in the heavy chain variable domain the HVRs of SEQ ID NO: 08, 09 and 04 and in the light chain variable domain the HVRs of SEQ ID NO: 10 to 12, wherein in each HVR up to 3 amino acid residues can be changed.
14. The antibody according to any one of items 1 to 7 and 12 to 13, characterized in that the antibody is a humanized antibody and the heavy chain variable domain is a humanized form of the (is derived from the) heavy chain variable domain consisting of SEQ ID NO: 13 and the light chain variable domain is a humanized form of the (is derived from the) light chain variable domain consisting of SEQ ID NO: 14.
15. The antibody according to any one of items 1 to 4, characterized in that the antibody binds to the same epitope as an antibody comprising in the heavy chain the HVRs of SEQ ID NO: 15 to 17 and in the light chain the HVRs of SEQ ID NO: 18 to 20.
16. The antibody according to any one of items 1 to 4, characterized in that the antibody binds to the same epitope as an antibody comprising in the heavy chain the HVRs of SEQ ID NO: 21, 22 and 17 and in the light chain the HVRs of SEQ ID NO: 23 to 25.
17. The antibody according to any one of items 15 and 16, characterized in that the antibody comprises a heavy chain variable domain consisting of SEQ ID NO: 26 and a light chain variable domain consisting of SEQ ID NO: 27.
18. The antibody according to any one of items 1 to 4, characterized in that the antibody has been obtained by humanizing an antibody comprising a heavy chain variable domain consisting of SEQ ID NO: 26 and a light chain variable domain consisting of SEQ ID NO: 27.
19. The antibody according to any one of items 1 to 4, characterized in that the antibody is a humanized antibody and comprises in the heavy chain variable domain the HVRs of SEQ ID NO: 15 to 17 and in the light chain variable domain the HVRs of SEQ ID NO: 18 to 20, wherein in each HVR up to 3 amino acid residues can be changed.
20. The antibody according to any one of items 1 to 4, characterized in that the antibody is a humanized antibody and comprises in the heavy chain variable domain the HVRs of SEQ ID NO: 21, 22 and 17 and in the light chain variable domain the HVRs of SEQ ID NO: 23 to 25, wherein in each HVR up to 3 amino acid residues can be changed.
21. The antibody according to any one of items 1 to 4 and 19 to 20, characterized in that the antibody is a humanized antibody and the heavy chain variable domain is a humanized form of the (is derived from the) heavy chain variable domain consisting of SEQ ID NO: 26 and the light chain variable domain is a humanized form of the (is derived from the) light chain variable domain consisting of SEQ ID NO: 27.
22. The antibody according to any one of items 1 to 4, characterized in that the antibody binds to the same epitope as an antibody comprising in the heavy chain the HVRs of SEQ ID NO: 28 to 30 and in the light chain the HVRs of SEQ ID NO: 31 to 33.
23. The antibody according to any one of items 1 to 4, characterized in that the antibody binds to the same epitope as an antibody comprising in the heavy chain the HVRs of SEQ ID NO: 28, 34 and 30 and in the light chain the HVRs of SEQ ID NO: 35 to 37.
24. The antibody according to any one of item 22 to 23, characterized in that the antibody comprises a heavy chain variable domain consisting of SEQ ID NO: 38 and a light chain variable domain consisting of SEQ ID NO: 39.
25. The antibody according to any one of items 1 to 4, characterized in that the antibody has been obtained by humanizing an antibody comprising a heavy chain variable domain consisting of SEQ ID NO: 38 and a light chain variable domain consisting of SEQ ID NO: 39.
26. The antibody according to any one of items 1 to 4, characterized in that the antibody is a humanized antibody and comprises in the heavy chain variable domain the HVRs of SEQ ID NO: 28 to 30 and in the light chain variable domain the HVRs of SEQ ID NO: 31 to 33, wherein in each HVR up to 3 amino acid residues can be changed.
27. The antibody according to any one of items 1 to 4, characterized in that the antibody is a humanized antibody and comprises in the heavy chain variable domain the HVRs of SEQ ID NO: 28, 34 and 30 and in the light chain variable domain the HVRs of SEQ ID NO: 35 to 37, wherein in each HVR up to 3 amino acid residues can be changed.
28. The antibody according to any one of items 1 to 4 and 26 to 27, characterized in that the antibody is a humanized antibody and the heavy chain variable domain is a humanized form of the (is derived from the) heavy chain variable domain consisting of SEQ ID NO: 38 and the light chain variable domain is a humanized form of the (is derived from the) light chain variable domain consisting of SEQ ID NO: 39.
29. The antibody according to any one of items 1 to 4 and 15 to 28, characterized in that the antibody specifically binds to fibrillar human alpha-synuclein and does not bind to non-fibrillar human alpha-synuclcin
30. The antibody according to any one of items 1 to 29, characterized in that the antibody is conjugated to a blood-brain-barrier shuttle module.
31. The antibody according to item 30, characterized in that the blood-brain-barrier shuttle module is an antibody or antibody fragment that specifically binds to LRP1, LRP8, human transferrin receptor or human insulin-like growth factor receptor.
32. The antibody according to any one of items 1 to 31, characterized in that the antibody is a monoclonal antibody.
33. The antibody according to any one of items 1 to 32, characterized in that the antibody is a humanized antibody or a chimeric antibody.
34. The antibody according to any one of items 1 to 33, characterized in that the antibody is an antibody fragment that binds to human alpha-synuclein and
  i) inhibits alpha-synuclcin induced cytotoxicity in human neurons and glia cells, and/or
  ii) inhibits cell-to-cell transmission of oligomeric human alpha-synuclein between neurons and glia cells, and/or
  iii) reduces alpha-synuclein-induced caspase activity in LUHMES cells.
35. The antibody according to any one of items 1 to 34, characterized in that the antibody is
  a) a full length antibody of the human subclass IgG1, or
  b) a full length antibody of the human subclass IgG4, or
  c) a full length antibody of the human subclass IgG1 with the mutations L234A, L235A and P329G,
  d) a full length antibody of the human subclass IgG4 with the mutations S228P, L235E and P329G,
  e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
  f) a full length antibody of the human subclass IgG4 with the mutations S228P and P329G in both heavy chains and the mutations T366W and S354C in one heavy chain and the mutations T366S, L368A, Y407V and Y349C in the respective other heavy chain.
36. An isolated nucleic acid encoding the antibody according to any one of items 1 to 35.
37. A host cell comprising the nucleic acid of item 36.
38. A method of producing an antibody comprising the steps of culturing the host cell of item 37 so that the antibody is produced.
39. The method according to item 38, characterized in that the method further comprises the step of recovering the antibody from the cell or the cultivation medium.

40. A pharmaceutical formulation comprising the antibody according to any one of items 1 to 35 and a pharmaceutically acceptable carrier.
41. The pharmaceutical formulation according to item 40, characterized in further comprising an additional therapeutic agent.
42. The antibody according to any one of items 1 to 35 for use as a medicament.
43. The antibody according to any one of items 1 to 35 for use in treating synucleinopathy.
44. The antibody according to any one of items 1 to 35 for use in treating Parkinson's Disease.
45. The antibody according to any one of items 1 to 35 for use in inhibiting alpha-synuclein induced cytotoxicity in human neurons and glia cells.
46. The antibody according to any one of items 1 to 35 for use in inhibiting cell-to-cell transmission of oligomeric human alpha-synuclein between neurons and glia cells.
47. The antibody according to any one of items 1 to 35 for use in reducing alpha-synuclein-induced caspase activity in neuronal cells or glia cells.
48. Use of the antibody according to any one of items 1 to 35 in the manufacture of a medicament.
49. The use of item 48, wherein the medicament is for treatment of Parkinson's Disease.
50. The use of item 48, wherein the medicament is for inhibiting alpha-synuclein induced cytotoxicity in human neurons and glia cells.
51. The use of item 48, wherein the medicament is for inhibiting cell-to-cell transmission of oligomeric human alpha-synuclein between neurons and glia cells.
52. The use of item 48, wherein the medicament is for reducing alpha-synuclein-induced caspase activity in neuronal cells or glia cells.
53. A method of treating an individual having Parkinson's Disease comprising administering to the individual an effective amount of the antibody according to any one of items 1 to 35.
54. A method of inhibiting alpha-synuclein induced cytotoxicity in human neurons and glia cells in an individual comprising administering to the individual an effective amount of the antibody according to any one of items 1 to 35 to inhibit alpha-synuclein induced cytotoxicity in human neurons and glia cells.
55. A method of inhibiting cell-to-cell transmission of oligomeric human alpha-synuclein between neurons and glia cells in an individual comprising administering to the individual an effective amount of the antibody according to any one of items 1 to 35 to inhibit alpha-synuclein induced cytotoxicity in human neurons and glia cells.
56. The use of an anti-human alpha synuclein antibody according to any one of items 1 to 35 in the inhibition of alpha-synuclein induced cytotoxicity in human neurons and glia cells.
57. The use of an anti-human alpha synuclein antibody according to any one of items 1 to 35 in the inhibition of cell-to-cell transmission of oligomeric human alpha-synuclein between neurons and glia cells.
58. The use of an anti-human alpha synuclein antibody according to any one of items 1 to 35 in the reduction of alpha-synuclein-induced caspase activity in neuronal cells or glia cells.
59. An antibody that specifically binds to human alpha-synuclein and comprises at least one, at least two, or all three VH HVR sequences selected from
  i) (a) HVR-H1 comprising the amino acid sequence of SEQ ID NO: 02; (b) HVR-H2 comprising the amino acid sequence of SEQ ID NO: 03; and (c) HVR-H3 comprising the amino acid sequence of SEQ ID NO: 04; or
  ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 04, or
  iii) (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17, or
  iv) (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 17, or
  v) (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30, or
  vi) (a) HVR-H1 comprising the amino acid sequence of SEQ ID NO: 28; (b) HVR-H2 comprising the amino acid sequence of SEQ ID NO: 34; and (c) HVR-H3 comprising the amino acid sequence of SEQ ID NO: 30.
60. An antibody that specifically binds to human alpha-synuclein and comprises as VH HVR sequences
  i) (a) HVR-H1 comprising the amino acid sequence of SEQ ID NO: 02; (b) HVR-H2 comprising the amino acid sequence of SEQ ID NO: 03; and (c) HVR-H3 comprising the amino acid sequence of SEQ ID NO: 04; or
  ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 04, or
  iii) (a) HVR-H1 comprising the amino acid sequence of SEQ ID NO: 15; (b) HVR-H2 comprising the amino acid sequence of SEQ ID NO: 16; and (c) HVR-H3 comprising the amino acid sequence of SEQ ID NO: 17, or
  iv) (a) HVR-H1 comprising the amino acid sequence of SEQ ID NO: 21; (b) HVR-H2 comprising the amino acid sequence of SEQ ID NO: 22; and (c) HVR-H3 comprising the amino acid sequence of SEQ ID NO: 17, or
  v) (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30, or
  vi) (a) HVR-H1 comprising the amino acid sequence of SEQ ID NO: 28; (b) HVR-H2 comprising the amino acid sequence of SEQ ID NO: 34; and (c) HVR-H3 comprising the amino acid sequence of SEQ ID NO: 30.
61. The antibody according to any one of items 59 to 60, characterized in further comprising at least one, at least two, or all three VL HVR sequences selected from
  i) (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07; or ii) (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12, or iii) (a) HVR-L1 comprising the amino acid sequence of SEQ ID NO: 18; (b) HVR-L2 comprising the amino acid sequence of SEQ ID NO: 19; and (c) HVR-L3 comprising the amino acid sequence of SEQ ID NO: 20, or iv) (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25, or v) (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33, or vi) (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37.

62. The antibody according to item 60, characterized in further comprising as VL HVR sequences
   i) (a) HVR-L1 comprising the amino acid sequence of SEQ ID NO: 05; (b) HVR-L2 comprising the amino acid sequence of SEQ ID NO: 06; and (c) HVR-L3 comprising the amino acid sequence of SEQ ID NO: 07; or
   ii) (a) HVR-L1 comprising the amino acid sequence of SEQ ID NO: 10; (b) HVR-L2 comprising the amino acid sequence of SEQ ID NO: 11; and (c) HVR-L3 comprising the amino acid sequence of SEQ ID NO: 12, or
   iii) (a) HVR-L1 comprising the amino acid sequence of SEQ ID NO: 18; (b) HVR-L2 comprising the amino acid sequence of SEQ ID NO: 19; and (c) HVR-L3 comprising the amino acid sequence of SEQ ID NO: 20, or
   iv) (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25, or
   v) (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33, or
   vi) (a) HVR-L1 comprising the amino acid sequence of SEQ ID NO: 35; (b) HVR-L2 comprising the amino acid sequence of SEQ ID NO: 36; and (c) HVR-L3 comprising the amino acid sequence of SEQ ID NO: 37.

63. An antibody that specifically binds to human alpha-synuclein and comprises as HVR sequences
   i) (a) HVR-H1 comprising the amino acid sequence of SEQ ID NO: 02; (b) HVR-H2 comprising the amino acid sequence of SEQ ID NO: 03; (c) HVR-H3 comprising the amino acid sequence of SEQ ID NO: 04; (d) HVR-L1 comprising the amino acid sequence of SEQ ID NO: 05; (e) HVR-L2 comprising the amino acid sequence of SEQ ID NO: 06; and (f) HVR-L3 comprising the amino acid sequence of SEQ ID NO: 07, or
   ii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 04; (d) HVR-L1 comprising the amino acid sequence of SEQ ID NO: 10; (e) HVR-L2 comprising the amino acid sequence of SEQ ID NO: 11; and (f) HVR-L3 comprising the amino acid sequence of SEQ ID NO: 12, or
   iii) (a) HVR-H1 comprising the amino acid sequence of SEQ ID NO: 15; (b) HVR-H2 comprising the amino acid sequence of SEQ ID NO: 16; (c) HVR-H3 comprising the amino acid sequence of SEQ ID NO: 17; (d) HVR-L1 comprising the amino acid sequence of SEQ ID NO: 18; (e) HVR-L2 comprising the amino acid sequence of SEQ ID NO: 19; and (f) HVR-L3 comprising the amino acid sequence of SEQ ID NO: 20, or
   iv) (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 17; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25, or
   v) (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33, or
   vi) (a) HVR-H1 comprising the amino acid sequence of SEQ ID NO: 28; (b) HVR-H2 comprising the amino acid sequence of SEQ ID NO: 34; (c) HVR-H3 comprising the amino acid sequence of SEQ ID NO: 30; (d) HVR-L comprising the amino acid sequence of SEQ ID NO: 35; (e) HVR-L2 comprising the amino acid sequence of SEQ ID NO: 36; and (f) HVR-L3 comprising the amino acid sequence of SEQ ID NO: 37.

64. An antibody specifically binding to human alpha-synuclein wherein the human alpha-synuclein has a free N-terminal methionine residue.

65. The antibody according to item 64, wherein the antibody is specifically binding to human and mouse alpha-synuclein wherein the human and mouse alpha-synuclein have a free N-terminal methionine residue.

66. The antibody according to any one of items 64 to 65, wherein the alpha-synuclein is monomeric alpha-synuclein.

67. The antibody according to any one of items 64 to 65, wherein the alpha-synuclein is oligomeric alpha-synuclein.

68. The antibody according to any one of items 64 to 67, wherein the alpha-synuclein is monomeric and oligomeric alpha-synuclein.

69. The antibody according to any one of items 64 to 68, wherein the antibody binds to the same epitope as an antibody comprising in the heavy chain the HVRs of SEQ ID NO: 15 to 17 and in the light chain the HVRs of SEQ ID NO: 18 to 20.

70. The antibody according to any one of items 64 to 69, wherein the antibody binds to the same epitope as an antibody comprising in the heavy chain the HVRs of SEQ ID NO: 21, 22 and 17 and in the light chain the HVRs of SEQ ID NO: 23 to 25.
71. The antibody according to any one of items 64 to 70, wherein the antibody binds to the same epitope as an antibody comprising a heavy chain variable domain of SEQ ID NO: 26 and a light chain variable domain of SEQ ID NO: 27.
72. The antibody according to any one of items 64 to 68, wherein the antibody comprises in the heavy chain the HVRs of SEQ ID NO: 15 to 17 and in the light chain the HVRs of SEQ ID NO: 18 to 20.
73. The antibody according to any one of items 64 to 68, wherein the antibody comprises in the heavy chain the HVRs of SEQ ID NO: 21, 22 and 17 and in the light chain the HVRs of SEQ ID NO: 23 to 25.
74. The antibody according to any one of items 64 to 68, wherein the antibody has been obtained by humanizing an antibody comprising a heavy chain variable domain of SEQ ID NO: 26 and a light chain variable domain of SEQ ID NO: 27.
75. The antibody according to any one of items 64 to 68, wherein the antibody is a humanized antibody and comprises in the heavy chain variable domain the HVRs of SEQ ID NO: 15 to 17 and in the light chain variable domain the HVRs of SEQ ID NO: 18 to 20, wherein in each HVR 0 to 3 amino acid residues have been changed.
76. The antibody according to any one of items 64 to 68, wherein the antibody is a humanized antibody and comprises in the heavy chain variable domain the HVRs of SEQ ID NO: 21, 22 and 17 and in the light chain variable domain the HVRs of SEQ ID NO: 23 to 25, wherein in each HVR 0 to 3 amino acid residues have been changed.
77. The antibody according to any one of items 64 to 68, wherein the antibody is a humanized antibody and the heavy chain variable domain is derived from a heavy chain variable domain of SEQ ID NO: 26 and a light chain variable domain is derived from a light chain variable domain of SEQ ID NO: 27.
78. An antibody that binds to the same epitope as an antibody comprising in the heavy chain the HVRs of SEQ ID NO: 15 to 17 and in the light chain the HVRs of SEQ ID NO: 18 to 20.
79. An antibody comprising in the heavy chain the HVRs of SEQ ID NO: 15 to 17 and in the light chain the HVRs of SEQ ID NO: 18 to 20.
80. An antibody comprising in the heavy chain the HVRs of SEQ ID NO: 21, 22 and 17 and in the light chain the HVRs of SEQ ID NO: 23 to 25.
81. A (variant) antibody that has been obtained from an antibody comprising a heavy chain variable domain of SEQ ID NO: 26 and a light chain variable domain of SEQ ID NO: 27.
82. The antibody according to any one of items 64 to 68, wherein the antibody is a humanized antibody that has been obtained by humanizing an antibody comprising a heavy chain variable domain of SEQ ID NO: 26 and a light chain variable domain of SEQ ID NO: 27.
83. A (humanized) antibody comprising in the heavy chain variable domain the HVRs of SEQ ID NO: 15 to 17 and in the light chain variable domain the HVRs of SEQ ID NO: 18 to 20, wherein in each HVR 0 to 3 amino acid residues have been changed.
84. A (humanized) antibody comprising in the heavy chain variable domain the HVRs of SEQ ID NO: 21, 22 and 17 and in the light chain variable domain the HVRs of SEQ ID NO: 23 to 25, wherein in each HVR 0 to 3 amino acid residues have been changed.
85. A (humanized) antibody wherein the heavy chain variable domain is derived from a heavy chain variable domain of SEQ ID NO: 26 and the light chain variable domain is derived from a light chain variable domain of SEQ ID NO: 27.
86. The antibody according to any one of items 64 to 85, wherein the antibody is conjugated to a blood-brain-barrier shuttle module.
87. The antibody according to item 86, wherein the blood-brain-barrier shuttle module is an antibody or antibody fragment that specifically binds to LRP1, LRP8, human transferrin receptor or human insulin-like growth factor receptor.
88. The antibody according to any one of items 64 to 87, wherein the antibody is a monoclonal antibody.
89. The antibody according to any one of items 64 to 88, wherein the antibody is a humanized antibody or a chimeric antibody.
90. The antibody according to any one of items 64 to 89, wherein the antibody is
   a) a full length antibody of the human subclass IgG1, or
   b) a full length antibody of the human subclass IgG4, or
   c) a full length antibody of the human subclass IgG with the mutations L234A, L235A and P329G,
   d) a full length antibody of the human subclass IgG4 with the mutations S228P, L235E and P329G,
   e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
   f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain.
91. An anti-human alpha-synuclein antibody, characterized in that
   a) the antibody comprises two antibody heavy chains each comprising a heavy chain variable domain and a heavy chain constant region, wherein
      i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
      ii) the constant region is a human IgG1 constant region, wherein the C-terminal lysine residue can be present or absent, and
      iii) the constant region comprises the amino acid changes L234A, L235A and P329G,
   b) the antibody comprises two antibody light chains each comprising a light chain variable domain and a light chain constant domain, wherein
      i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
      ii) the constant region is a human kappa light chain constant region or a human lambda light chain constant region.
92. An anti-human alpha-synuclein antibody, characterized in that
   a) the antibody comprises two antibody heavy chains each comprising a heavy chain variable domain and a heavy chain constant region, wherein
      i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
      ii) the constant region is a human IgG1 constant region, wherein the C-terminal lysine residue can be present or absent, and iii) the constant region comprises the amino acid changes L234A, L235A and P329G,
b) the antibody comprises two antibody light chains each comprising a light chain variable domain and a light chain constant domain, wherein
i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
ii) the constant region is a human kappa light chain constant region or a human lambda light chain constant region.

93. An anti-human alpha-synuclein antibody, characterized in that
a) the antibody comprises two antibody heavy chains each comprising a heavy chain variable domain and a heavy chain constant region, wherein
i) the variable domain is a humanized form of the non-human (rabbit) variable domain of SEQ ID NO: 26,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain is a humanized form of the non-human (rabbit) variable domain of SEQ ID NO: 27,
ii) the constant region is a human kappa light chain constant region or a human lambda light chain constant region.

94. An anti-human alpha-synuclein antibody, characterized in that
a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
ii) the constant region is a human kappa light chain constant region or a human lambda light chain constant region.

95. An anti-human alpha-synuclein antibody, characterized in that
a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
ii) the constant region is a human kappa light chain constant region or a human lambda light chain constant region.

96. An anti-human alpha-synuclein antibody, characterized in that
a) the antibody comprises two antibody heavy chains each comprising in N- to C-terminal direction a heavy chain variable domain, a heavy chain constant region, a peptidic linker and a scFab or scFv antibody fragment, which specifically binds to human transferrin receptor, wherein
i) the variable domain is a humanized form of the rabbit variable domain of SEQ ID NO: 26,
ii) the constant region is a human IgG1 constant region, wherein the C-terminal lysine residue can be present or absent, and
iii) the constant region comprises the amino acid changes L234A, L235A and P329G,
b) the antibody comprises two antibody light chains each comprising a light chain variable domain and a light chain constant domain, wherein
i) the variable domain is a humanized form of the rabbit variable domain of SEQ ID NO: 27,
ii) the constant region is a human kappa light chain constant region or a human lambda light chain constant region.

97. An anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
ii) the constant region is a human IgG1 constant region, wherein the C-terminal lysine residue can be present or absent,
iii) the constant region comprises the amino acid changes L234A, L235A and P329G, and
iv) the constant region comprises either the amino acid changes T366W and S354C or the amino acid changes T366S, L368A, Y407V and Y349C, b) the antibody comprises a second antibody heavy chain comprising in N- to C-terminal direction a heavy chain variable domain and a heavy chain constant region, wherein
   i) the variable domain comprises the HVRs of SEQ ID NO: 15, SEQ ID NO: 16 and SEQ ID NO: 17, wherein in each HVR independently of each other 0, 1, 2 or 3 amino acid residues are changed,
   ii) the constant region is a human IgG1 constant region, wherein the C-terminal lysine residue can be present or absent,
   iii) the constant region comprises the amino acid changes L234A, L235A and P329G, and
   iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
   i) the variable domain comprises the HVRs of SEQ ID NO: 18, SEQ ID NO: 19 and SEQ ID NO: 20, wherein in each HVR independently of each other 0, 1, 2 or 3 amino acid residues are changed,
   ii) the constant region is a human kappa light chain constant region or a human lambda light chain constant region.

98. An anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
   i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
   ii) the constant region is a human IgG1 constant region, wherein the C-terminal lysine residue can be present or absent,
   iii) the constant region comprises the amino acid changes L234A, L235A and P329G, and
   iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
   i) the variable domain comprises the HVRs of SEQ ID NO: 21, SEQ ID NO: 22 and SEQ ID NO: 17, wherein in each HVR independently of each other 0, 1, 2 or 3 amino acid residues are changed,
   ii) the constant region is a human IgG1 constant region, wherein the C-terminal lysine residue can be present or absent,
   iii) the constant region comprises the amino acid changes L234A, L235A and P329G, and
   iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
   i) the variable domain comprises the HVRs of SEQ ID NO: 23, SEQ ID NO: 24 and SEQ ID NO: 25, wherein in each HVR independently of each other 0, 1, 2 or 3 amino acid residues are changed,
   ii) the constant region is a human kappa light chain constant region or a human lambda light chain constant region.

99. An anti-human alpha-synuclein antibody, characterized in that
a) the antibody comprises a first antibody heavy chain comprising in N- to C-terminal direction a heavy chain variable domain, a heavy chain constant region, a peptidic linker and a scFab or scFv antibody fragment, which specifically binds to human transferrin receptor, wherein
   i) the variable domain is a humanized form of the rabbit variable domain of SEQ ID NO: 26,
   ii) the constant region is a human IgG1 constant region, wherein the C-terminal lysine residue can be present or absent,
   iii) the constant region comprises the amino acid changes L234A, L235A and P329G, and
   iv) the constant region comprises either the amino acid changes T366W and S354C or the amino acid changes T366S, L368A, Y407V and Y349C,
b) the antibody comprises a second antibody heavy chain comprising in N- to C-terminal direction a heavy chain variable domain and a heavy chain constant region, wherein
   i) the variable domain is a humanized form of the rabbit variable domain of SEQ ID NO: 26,
   ii) the constant region is a human IgG1 constant region, wherein the C-terminal lysine residue can be present or absent,
   iii) the constant region comprises the amino acid changes L234A, L235A and P329G, and
   iv) the constant region comprises the amino acid changes T366W and S354C if the first antibody heavy chain comprises the amino acid changes T366S, L368A, Y407V and Y349C or the constant region comprises the amino acid changes T366S, L368A, Y407V and Y349C if the first antibody heavy chain comprises the amino acid changes T366W and S354C,
c) the antibody comprises two antibody light chains each comprising a light chain variable domain and a light chain constant domain, wherein
   i) the variable domain is a humanized form of the rabbit variable domain of SEQ ID NO: 27,
   ii) the constant region is a human kappa light chain constant region or a human lambda light chain constant region.

100. The antibody according to any one of items 94 to 99, wherein the antibody fragment, which specifically binds to human transferrin receptor, comprises a heavy chain variable domain that is a humanized form of the heavy chain variable domain of SEQ ID NO: 56 and a light chain variable domain that is a humanized form of the light chain variable domain of SEQ ID NO: 57.

101. The antibody according to any one of items 64 to 100, wherein the antibody
   i) inhibits alpha-synuclein induced cytotoxicity in human neurons and glia cells, and/or
   ii) inhibits cell-to-cell transmission of oligomeric human alpha-synuclein between neurons and glia cells, and/or
   iii) reduces alpha-synuclein-induced caspase activity in human neuronal cells, and/or
   iv) specifically binds to alpha-synuclein that has a free N-terminal methionine residue and does not specifically bind to alpha-synuclein has a modified N-terminal methionine residue.

V. Examples

The following are examples of methods and compositions of the invention. It is understood that various other embodiments may be practiced, given the general description provided above.

Materials and Methods
Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an *E. coli* plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Cell Clones
antibody 0017=ASYN-233HC_110-IV=aSyn.S019.006A08
antibody 0018=ASYN-064HC_110-II=aSyn.S003.006A11
antibody 0081=ASYN-235HC_110-IV=aSyn.S019.005A08
antibody 0070=antibody 0017+blood-brain-barrier shuttle module
antibody 0076=antibody 0018+blood-brain-barrier shuttle module

Example 1

Preparation of the Antigen

Materials
Proteins: —lyophilized human wild-type alpha-synuclein (100 µg, 200 µg, or 500 µg aliquots);
human mutant TP alpha-synuclein (8.2 mg/ml, dialyzed in 50 mM HEPES/100 mM NaCl)
Buffers and solutions (stored at room temperature and protected from direct sunlight exposure):
   PB stock (5×): 250 mM phosphate buffer, pH 7.0 (0.22 µm filtered)
   EtOH stock: ethanol absolute pro analysis grade (EMSURE) (Merck; Cat. No. 1.00989.1000)
   HPLC grade water (LiChrosolv, Merck)
   50 mM HEPES/100 mM NaCl, pH 7.4 (0.22 rpm filtered)
   TBS (50 mM Tris/100 mM NaCl) pH 7.0 (0.22 µm filtered)
   BioPORTER protein delivery reagent (Genlantis, Cat. No. BP502424)

Preparation of A1-Oligomers

For reference see Danzer, K. M., et al., J. Neurosci. 27 (2007) 9220-9232, and Danzer, K. M., et al., J. Neurochem. 111 (2009) 192-203.

Lyophilized alpha-synuclein was solubilized in HPLC water to obtain a solution about 70 µM in alpha-synuclein (100 µl per 100 µg protein). The solution was sonicated for 30 sec. in water bath sonicator using a tube floating device. Thereafter 500 µl HPLC grade water, 200 µl 250 mM PB pH 7.0, 200 µl EtOH absolute pro analysis were added. The mixture was vortexed at full speed for 10 sec. Afterwards a 100 µg/ml alpha-synuclein solution in 50 mM PB pH 7.0/20% ethanol was generated. For reference sample the same buffers in the absence of alpha-synuclein were mixed. The solution was shaken for 4 h at room temperature on a nutator. After shaking the solutions were frozen on dry-ice for immediate lyophilization. The lyophilization was performed overnight at room temperature under constant spinning (e.g. in a Speedvac). The lyophilisate was resuspended in 0.5 ml of 50 mM PB pH 7.0 with 10% ethanol. The ethanol was evaporated at 20-21° C. for 24 h in the fume hood with open cap (Eppendorf Thermomixer 5436, speed 5). Thereafter the cap was closed and shaking was continued at room temperature for 6 days. The A1-oligomers were concentrated up to 1 mg/ml with Vivaspin 500 (30 kD cut-off) and pooled for immunization. For long-term storage the oligomers were kept at −80° C. Quality control for proper oligomer formation was done by SDS-PAGE and EM.

Preparation of C1-Oligomers

For reference see Danzer, K. M., et al., J. Neurosci. 27 (2007) 9220-9232, and Danzer, K. M., et al., J. Neurochem. 111 (2009) 192-203.

Lyophilized alpha-synuclein was solubilized in HPLC grade water to get a solution with a concentration of about 70 µM (100 µl per 100 µg protein). The solution was sonicated for 30 sec. in a water bath sonicator using a tube floating device. Thereafter 500 µl HPLC grade water, 200 µl 250 mM PB pH 7.0, 200 µl ethanol absolute pro analysis were added. The mixture was vortexed at full speed for 10 sec. Solutions of 100 µg/ml alpha-synuclein in 50 mM PB pH 7.0/20% ethanol were generated. For control samples the same buffers in the absence of alpha-synuclein were mixed. The solutions were shaken for 16 h at room temperature on a nutator (e.g. overnight). The C1-oligomers were concentrated up to 1 mg/ml with Vivaspin 500 (30 kD cut-off) and pooled for immunization. For long-term storage the oligomers were kept at −80° C. Quality control for proper oligomer formation was done by SDS-PAGE and EM.

Preparation of TP Mutant Alpha-Synuclein Oligomers

Adapted from Karpinar, D. P., et al., EMBO J. 28 (2009) 3256-3268.

Aliquots of 100 µl of 8.2 mg/ml (about 590 mM) TP alpha-synuclein in 50 mM HEPES/100 mM NaCl pH 7.4 were stirred with a 2×5 mm micro magnetic stir bar at 37° C. (200 rpm) for 6 days. Quality control for proper oligomer formation was done by SDS-PAGE and EM.

Alpha-Synuclein Fibril Formation and Mixing with BioPORTER

Adapted from to Luk, K. C., et al., Biochem. 46 (2007) 12522-12526, and Luk, K. C., et al., Proc. Natl. Acad. Sci. USA 106 (2009) 20051-20056.

Lyophilized and vacuumized alpha-synuclein aliquot (from −80° C.) was brought to room temperature (RT) for 10-15 min without opening the vacuumized bag. In the meantime the orbital tube mixer was pre-heated to 37° C. Thereafter the bag containing the tubes was opened and if needed water drops on the outside of the tube were cleaned off. 100 µg of lyophilized alpha-synuclein were dissolved in 100 µl TBS pH 7. The tubes were put into an orbital tube mixer and incubated at 37° C./1000 rpm for 96 h. Thereafter the tube was spun down at full speed (20,000 g) for 10 minutes at room temperature. Of the supernatant 90 µl were removed. The pellet was resuspended with 90 µl of fresh TBS (assuming about 1 mg/ml concentration). Quality control for proper fibril formation was done by SDS-PAGE and EM. For long term storage the sample was kept at −80° C.

Shortly before immunizing 100 µl of 1 mg/ml well suspended fibrils were added to 20 µl BioPORTER reagent dry-film and vigorously mixed by vortexing and water bath sonication. The solution was incubated for 10 min. at room temperature before using for immunization.

Example 2

Immunization of Rabbits

Three New Zealand White rabbits were immunized with a mixture of alpha-synuclein C1 oligomers, alpha-synuclein fibrils and alpha-synuclein TP mutant oligomers (400 µg of each component for the first immunization; 200 µg of each component for consecutive immunizations; preparation see Example 1). Animals received the immunogen, emulsified with complete Freund's adjuvant, by intradermal application at day 0, and by alternating intramuscular and subcutaneous applications at days 7, 14, 35, 63 and 91. Blood (10% of estimated total blood volume) was taken at days 21, 41, 69 and 97. Serum was prepared, which was used for titer determination by ELISA (see below). Peripheral mononuclear cells were isolated, which were used as a source of antigen-specific B-cells in the B-cell cloning process (Examples 3 and 4).

Determination of Serum Titers

Titers were determined separately for each component of the immunogen mixture. Alpha-synuclein C1 oligomers, alpha-synuclein fibrils, or alpha-synuclein TP mutant oligomers were immobilized on a 96-well NUNC Maxisorb plate at 0.6 µg/ml, 100 µl/well, in PBS (phosphate buffered saline solution), followed by: blocking of the plate with 2% CroteinC in PBS, 200 µl/well; application of serial dilutions of antisera, in duplicates, in 0.5% CroteinC in PBS, 100 µl/well; detection with HRP-conjugated (horseradish peroxidase-conjugated) donkey anti-rabbit IgG antibody (Jackson Immunoresearch) diluted 1:16,000 in 0.5% CroteinC in PBS, 100 µl/well. For all steps, plates were incubated for one hour at 37° C. Between all steps, plates were washed three-times with 0.05% Tween 20 in PBS. Signal was developed by addition of BM Blue POD Substrate soluble (Roche Diagnostics GmbH, Mannheim, Germany), 100 µl/well, and stopped by addition of 1 M HCl, 100 µl/well. Absorbance was read out at 450 nm, against 690 nm as reference. Titer was defined as dilution of antisera resulting in half-maximal signal.

Example 3

Isolation of Anti-Human Alpha-Synuclein Antibody Producing B-Cells

Isolation of Rabbit Peripheral Blood Mononuclear Cells (PBMC)

Three rabbits (described in the Example 2) were used as a source of blood. EDTA containing whole blood was diluted two-fold with 1× PBS (phosphate buffered saline; PAA, Pasching, Austria) before density centrifugation using lympholyte mammal (Cedarlane Laboratories, Burlington, Ontario, Canada) according to the specifications of the manufacturer. The PBMCs were washed twice with 1×PBS.

EL-4 B5 Medium

RPMI 1640 (Pan Biotech, Aidenbach, Germany) supplemented with 10% FCS (Hyclone, Logan, Utah, USA), 2 mM Glutamine, 1% penicillin/streptomycin solution (PAA, Pasching, Austria), 2 mM sodium pyruvate, 10 mM HEPES (PAN Biotech, Aidenbach, Germany) and 0.05 mM β-mercaptoethanol (Gibco, Paisley, Scotland).

Depletion of Macrophages/Monoctes

Sterile 6-well plates (cell culture grade) were used to deplete macrophages and monocytes through unspecific adhesion. Each well was filled at maximum with 4 ml medium and up to $6\times10^6$ PBMCs from the immunized rabbit and allowed to bind for 1 h at 37° C. in the incubator. The cells in the supernatant (peripheral blood lymphocytes (PBLs)) were used for the antigen panning step.

Coating of Plates

Sterile cell culture 6-well plates were coated with a mixture of two different human alpha-synuclein oligomers (1 µg/ml C1 oligomer and 1 µg/ml TP mutant oligomer) in carbonate buffer (0.1 M sodium bicarbonate, 34 mM disodium hydrogen carbonate, pH 9.55) over night at 4° C. Plates were washed in sterile PBS three times before use.

Enrichment of B-Cells on Human Alpha-Synuclein Oligomers 6-well tissue culture plates coated with human alpha-synuclein oligomers were seeded with up to $6\times10^6$ PBLs per 4 ml medium and allowed to bind for 1 h at 37° C. in the incubator. After the enrichment step on the alpha-synuclein oligomers non-adherent cells were removed by carefully washing the wells 1-2 times with 1×PBS. The remaining sticky cells were detached by trypsin for 10 min. at 37° C. in the incubator. Trypsination was stopped with EL-4 B5 medium. The cells were kept on ice until the immune fluorescence staining.

Immune Fluorescence Staining and Flow Cytometry

The anti-IgG antibody FITC conjugate (AbD Serotec, Düsseldorf, Germany) was used for single cell sorting. For surface staining, cells from the depletion and enrichment step were incubated with the anti-IgG antibody FITC conjugate in PBS and incubated for 45 min. in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells.

A Becton Dickinson FACSAria equipped with a computer and the FACSDiva software (BD Biosciences, USA) were used for single cell sort.

B-Cell Cultivation

The cultivation of the rabbit B-cells was prepared by a method similar to that described by Zubler et al. (J. Exp. Med. 160 (1984) 1170-1183). Briefly, single sorted rabbit B-cells were incubated in 96-well plates with 200 l/well EL-4 B5 medium containing Pansorbin Cells (1:100000) (Calbiochem (Merck), Darmstadt, Deutschland), 5% rabbit thymocyte supernatant (charge 20100908, in-house production) and gamma-irradiated murine EL-4-B5 thymoma cells ($2.5\times10^4$/well) for 7 days at 37° C. under 5% $CO_2$. The supernatants of the B-cell cultivation were removed for screening. In parallel the mRNA of the remaining cells were immediately preserved in 100 µl RLT buffer (Qiagen, Hilden, Germany) and the lysates were frozen at −80° C.

Example 4

Determination of Antibody Variable Domain Encoding Nucleic Acids

PCR Amplification of V-Domains and Sequencing

Total RNA was prepared using the NucleoSpin 8/96 RNA kit (Macherey & Nagel; Cat-No. 740709.4, 740698) according to manufacturer's protocol. All steps were done on an epMotion 5075 liquid handling system (Eppendorf). RNA was eluted with 60 µl RNAse free water. 6 µl of RNA was used to generate cDNA by reverse transcriptase reaction using the Superscript III First-Strand Synthesis SuperMix (Invitrogen; Cat-No. 18080-400) and an oligo dT-primer according to the manufacturer's instructions. 4 µl of cDNA were used to amplify the immunoglobulin heavy and light chain variable regions (VH and VL) with the AccuPrime SuperMix (Invitrogen; Cat-No. 12344-040) in a final volume of 50 µl using the primers rbHCfinal.up (AAGCTT-GCCACCATGGAGACTGGGC TGCGCTGGCTTC; SEQ ID NO: 42) and rbHCfinal.do (CCATTGGTG AGGGTGC-CCGAG; SEQ ID NO: 43) for the heavy chain and rbLC-final.up (AAGCTTGCCACCATGGACAYGAGGGC-CCCCACTC; SEQ ID NO: 44) and rbLCfinal.do (CAGAGTRCTGCTGAGGTrGTAGGTAC; SEQ ID NO: 45) for the light chain. The PCR conditions were as follows: hot start at 94° C. for 5 min.; 35 cycles of 20 s. at 94° C., 20 s. at 70° C., 45 s. at 68° C., and a final extension at 68° C. for 7 min.

Eight microliters of the 50 µl PCR solution were loaded on a 48 E-Gel 2% (Invitrogen; Cat-No. G8008-02). Positive PCR reactions were cleaned using the NucleoSpin Extract II kit (Macherey & Nagel; Cat-No. 740609250) according to manufacturer's protocol and eluted in 50 µl elution buffer. 12 µl of purified PCR products were sequenced directly in both directions using the rbHCfinal.up and rbHCfinal.do for heavy chains and rbLCfinal.up and rbLCfinal.do for light chains.

Example 5

Humanization of Rabbit Anti-Human Alpha-Synuclein Antibodies

The rabbit anti-human alpha-synuclein antibodies can be humanized according to standard techniques, such as CDR grafting.

Example 6

Generation of Recombinant Expression Vectors a) Generation of Vectors for the Expression of Immunoglobulin Heavy Chains Using the Mouse IgG1 Constant Region The mouse IgG1 encoding fusion gene comprising the mouse IgG1 constant region (CH1, hinge, CH2, CH3) and an anti-alpha synuclein-antibody VH domain derived from rabbit was assembled by fusing a DNA fragment coding for the respective anti-alpha-synuclein-specific antibody VH domain to a sequence element coding the mouse IgG1 constant region.

The mouse IgG1 constant region has the following amino acid sequence:

```
                                              (SEQ ID NO: 46)
AKTTPPSVYP LAPGSAAQTN SMVTLGCLVK GYFPEPVTVT

WNSGSLSSGV HTFPAVLQSD LYTLSSSVTV PSSTWPSETV

TCNVAHPASS TKVDKKIVPR DCGCKPCICT VPEVSSVFIF

PPKPKDVLTI TLTPKVTCVV VDISKDDPEV QFSWFVDDVE

VHTAQTQPRE EQFNSTFRSV SELPIMHQDW LNGKEFKCRV

NSAAFPAPIE KTISKTKGRP KAPQVYTIPP PKEQMAKDKV

SLTCMITDFF PEDITVEWQW NGQPAENYKN TQPIMDTDGS

YFVYSKLNVQ KSNWEAGNTF TCSVLHEGLH NHHTEKSLSH

SPGK.
```

The expression vector also comprised an origin of replication from the vector pUC18, which allows replication of this plasmid in E. coli, and a beta-lactamase gene which confers ampicillin resistance in E. coli.

The transcription unit of the antibody heavy chain comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a heavy chain variable (VH) domain encoding nucleic acid,
- a mouse IgG1 constant region encoding nucleic acid, and
- the bovine growth hormone polyadenylation sequence (BGH pA).

b) Generation of Vectors for the Expression of Immunoglobulin Light Chains Using the Mouse Ig-Kappa Constant Region The mouse kappa light chain encoding fusion gene comprising the mouse Ig-kappa constant region (CL-kappa) and an anti-alpha synuclein-antibody VL (kappa) domain derived from rabbit was assembled by fusing a DNA fragment coding for the respective anti-alpha-synuclein-antibody VL (kappa) domain to a sequence element coding for the mouse Ig-kappa constant region.

The mouse Ig-kappa constant region has the following amino acid sequence:

```
                                              (SEQ ID NO: 47)
RADAAPTVSI FPPSSEQLTS GGASVVCFLN NFYPKDINVK

WKIDGSERQN GVLNSWTDQD SKDSTYSMSS TLTLTKDEYE

RHNSYTCEAT HKTSTSPIVK SFNRNEC.
```

The expression vector also comprised an origin of replication from the vector pUC18, which allows replication of this plasmid in E. coli, and a beta-lactamase gene which confers ampicillin resistance in E. coli.

The transcription unit of the antibody kappa light chain comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a light chain variable (VL) domain encoding nucleic acid,
- a mouse Ig-kappa constant region encoding nucleic acid, and the bovine growth hormone polyadenylation sequence (BGH pA).

c) Generation of Vectors for the Expression of Immunoglobulin Light Chains Using the Mouse Ig-Lambda Constant Region The mouse lambda light chain encoding fusion gene comprising the mouse Ig-lambda constant region (CL-lambda) and an anti-alpha synuclein-antibody VL (lambda) domain derived from rabbit was assembled by fusing a DNA fragment coding for the respective anti-alpha-synuclein-antibody VL (lambda) domain to a sequence element coding for the mouse Ig-lambda constant region.

The mouse Ig-lambda constant region has the following amino acid sequence:

```
                                          (SEQ ID NO: 48)
GQPKSSPSVT LFPPSSEELE TNKATLVCTI TDFYPGVVTV

DWKVDGTPVT QGMETTQPSK QSNNKYMASS YLTLTARAWE

RHSSYSCQVT HEGHTVEKSL SRADCS.
```

The expression vector also comprised an origin of replication from the vector pUC18, which allows replication of this plasmid in *E. coli*, and a beta-lactamase gene which confers ampicillin resistance in *E. coli*.

The transcription unit of the antibody lambda light chain comprises the following functional elements in 5' to 3' direction:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- a variable light chain (VL) domain encoding nucleic acid,
- a mouse Ig-lambda constant region encoding nucleic acid, and
- the bovine growth hormone polyadenylation sequence (BGH pA).

d) Generation of Vectors for the Expression of Immunoglobulin Chains Conjugated to a Blood-Brain-Barrier Shuttle Module In case of expression vectors coding for IgG heavy chain constructs, the IgG part of the molecule was in a genomic organization, i.e. introns were present in the signal peptide, between the VH and CH1 domains, between the CH1 domain and the hinge region, between the hinge region and the CH2 domain, and between the CH2 and CH3 domains. Thereto (C-terminal/at the 3' end) a cDNA element coding for the brain shuttle module was fused. To produce antibody molecules bearing only one brain shuttle module per complete antibody molecule the "knob-into-hole" technology was employed.

The hole-heavy chain comprises the following mutations: T366W.

The knob-heavy chain comprises the following mutations: T366S/L368A/Y407V.

Optionally an artificial disulfide bond can be introduced between the residue 354 of the hole-heavy chain and the residue 349 of the knob-heavy chain. The additionally required mutations are S354C in the hole-heavy chain and Y349C in the knob heavy chain.

In case of expression vectors coding for Ig light chain constructs, the Ig-kappa or Ig-lambda part of the molecule was in a genomic organization, i.e. introns were present in the signal peptide and between the VL and CL domains.

In addition to the expression unit/cassette including the desired gene to be expressed the basic/standard mammalian expression plasmid contains i) Generation of Vectors for the Expression of Immunoglobulin Heavy Chains Containing a Shuttle Module Using the Human IgG1 Constant Region with "Hole" Mutation The human IgG1 encoding fusion gene comprising the human IgG1 constant region (CH1, hinge, CH2, CH3) and an anti-alpha synuclein-antibody VH domain derived from rabbit was assembled by fusing a DNA fragment coding for the respective anti-alpha-synuclein-antibody VH domain to a sequence element coding for the human IgG1 constant region containing the "hole" mutation. The construct was in a genomic organization, i.e. introns were present in the signal peptide, between the VH and CH1 domains, between the CH1 domain and the hinge region, between the hinge region and the CH2 domain, and between the CH2 and CH3 domains.

The human Ig1 constant region has the following amino acid sequence:

```
                                          (SEQ ID NO: 49)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVESCSV MHEALHNHYT

QKSLSLSPGK.
```

The human Ig1 hole constant region has the following amino acid sequence:

```
                                          (SEQ ID NO: 50)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLWC LVKGFYPSDI AVEWESNGQP ENNYKTTPPV

LDSDGSFFLY SKLTVDKSRW QQGNVFSCSV MHEALHNHYT

QKSLSLSPGK.
```

The expression vector also comprised an origin of replication from the vector pUC18, which allows replication of this plasmid in *E. coli*, and a beta-lactamase gene which confers ampicillin resistance in *E. coli*.

The transcription unit of the hole-antibody heavy chain comprises the following functional elements in 5' to 3' direction:
- the immediate early enhancer and promoter from the human cytomegalovirus (P-CMV),
- a human heavy chain immunoglobulin 5'-untranslated region (5'UTR), a murine immunoglobulin heavy chain signal sequence,
a heavy chain variable (VH) domain encoding nucleic acid,
a human IgG1 constant region with "hole" mutation encoding nucleic acid,
optionally a GS-linker encoding nucleic acid fused to a blood-brain-barrier shuttle module encoding nucleic acid, and
the bovine growth hormone polyadenylation sequence (BGH pA).

ii) Generation of Vectors for the Expression of Immunoglobulin Heavy Chains Containing a Shuttle Module Using the Human IgG1 Constant Region with "Knob" Mutation The human IgG1 encoding fusion gene comprising the human IgG1 constant region (CH1, hinge, CH2, CH3) and an anti-alpha synuclein-antibody VH domain derived from rabbit was assembled by fusing a DNA fragment coding for the respective anti-alpha-synuclein-antibody VH domain to a sequence element coding for the human IgG1 constant region containing the "knob" mutation. The construct was in a genomic organization, i.e. introns were present in the signal peptide, between the VH and CH1 domains, between the CH1 domain and the hinge region, between the hinge region and the CH2 domain, and between the CH2 and CH3 domains.

The human Ig1 knob constant region has the following amino acid sequence:

```
                                            (SEQ ID NO: 51)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLSC AVKGFYPSDI AVEWESNGQP ENNYKTTPPV

LDSDGSFFLV SKLTVDKSRW QQGNVFSCSV MHEALHNHYT

QKSLSLSPGK.
```

The expression vector also comprised an origin of replication from the vector pUC18, which allows replication of this plasmid in *E. coli*, and a beta-lactamase gene which confers ampicillin resistance in *E. coli*.

The transcription unit of the knob-antibody heavy chain comprises the following functional elements in 5' to 3' direction:
the immediate early enhancer and promoter from the human cytomegalovirus (P-CMV),
a human heavy chain immunoglobulin 5'-untranslated region (5'UTR),
a murine immunoglobulin heavy chain signal sequence,
a heavy chain variable (VH) domain encoding nucleic acid,
a human IgG1 constant region with "knob" mutation encoding nucleic acid,
optionally a GS-linker encoding nucleic acid fused to a blood-brain-barrier shuttle module encoding nucleic acid, and
the bovine growth hormone polyadenylation sequence (BGH pA).

iii) Generation of Vectors for the Expression of Immunoglobulin Kappa Light Chains Using the Human Ig-Kappa Constant Region The human Ig-kappa light chain encoding fusion gene comprising the human Ig-kappa constant region (CL-kappa) and an anti-alpha synuclein-antibody VL (kappa) domain derived from rabbit was assembled by fusing a DNA fragment coding for the respective anti-alpha-synuclein-antibody VL (kappa) domain to a sequence element coding for the human Ig-kappa constant region. The construct was in a genomic organization, i.e. introns were present in the signal peptide and between the VL (kappa) and the CL-kappa domains.

The expression vector also comprised an origin of replication from the vector pUC18, which allows replication of this plasmid in *E. coli*, and a beta-lactamase gene which confers ampicillin resistance in *E. coli*.

The transcription unit of the antibody kappa light chain comprises the following functional elements in 5' to 3' direction:
the immediate early enhancer and promoter from the human cytomegalovirus (P-CMV)
a human heavy chain immunoglobulin 5'-untranslated region (5'UTR),
a murine immunoglobulin heavy chain signal sequence,
a light chain variable (VL) domain encoding nucleic acid,
a human IgG kappa constant region,
optionally a GS-linker encoding nucleic acid fused to a blood-brain-barrier shuttle module encoding nucleic acid, and
the bovine growth hormone polyadenylation sequence (BGH pA).

iv) Generation of Vectors for the Expression of Immunoglobulin Lambda Light Chains Using the Human Ig-Lambda Constant Region The human Ig-lambda light chain encoding fusion gene comprising the human Ig-lambda constant region (CL-lambda) and an anti-alpha synuclein-antibody VL (lambda) domain derived from rabbit was assembled by fusing a DNA fragment coding for the respective anti-alpha-synuclein-antibody VL (lambda) domain to a sequence element coding for the human Ig-lambda constant region. The construct was in a genomic organization, i.e. introns were present in the signal peptide and between the VL (lambda) and the CL-lambda domains.

The expression vector also comprised an origin of replication from the vector pUC18, which allows replication of this plasmid in *E. coli*, and a beta-lactamase gene which confers ampicillin resistance in *E. coli*.

The transcription unit of the antibody lambda light chain comprises the following functional elements in 5' to 3' direction:
the immediate early enhancer and promoter from the human cytomegalovirus (P-CMV)
a human heavy chain immunoglobulin 5'-untranslated region (5'UTR),
a murine immunoglobulin heavy chain signal sequence,
a light chain variable (VL) domain encoding nucleic acid,
a human IgG lambda constant region,
optionally a GS-linker encoding nucleic acid fused to a blood-brain-barrier shuttle module encoding nucleic acid, and
the bovine growth hormone polyadenylation sequence (BGH pA).

Example 7

Recombinant Production of Anti-Human Alpha-Synuclein Antibodies

The antibodies were produced in transiently transfected HEK293 cells (human embryonic kidney cell line 293-derived) cultivated in F17 Medium (Invitrogen Corp.). For transfection of the respective vectors as described in Example 6 "293-Free" Transfection Reagent (Novagen) was used. The antibodies and antibody-blood-brain-barrier shuttle-fusions were expressed from individual expression plasmids. Transfections were performed as specified in the manufacturer's instructions. Recombinant antibody-containing cell culture supernatants were harvested three to seven days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

Example 8

Purification of Recombinant Anti-Human Alpha-Synuclein Antibodies

The antibody-containing culture supernatants were filtered and purified by two chromatographic steps.

The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.1, which was immediately after elution adjusted to pH 6.0 with 1 M Tris-base, pH 9.0.

Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass., USA) and stored at −80° C.

TABLE average yields per liter culture supernatant

| antibody | average yields per liter culture supernatant |
| --- | --- |
| 0017 | 10 mg |
| 0018 | 9.2 mg |
| 0070 | 6.1 mg |
| 0076 | 7.3 mg |
| 0081 | 15 mg |
| 12F4-shuttle | 14.3 mg |

Example 9

Characterization of Binding Specificity Using Surface Plasmon Resonance

BIAcore 2000, 3000 or T200 instruments (GE Healthcare, BIAcore, Uppsala, Sweden) were applied in all described methods. All immobilization steps and binding assays were performed at 25° C. Immobilizations and binding assays were performed (if not special mentioned) at 5 or 30 µl $min^{-1}$, respectively.

a) Characterization of Monomeric Alpha-Synuclein Binding to Immobilized Monoclonal Antibodies
Buffers: Immobilization buffer:
  10 mM Hepes, 150 mM NaCl, 0.05% polysorbate 20 (P20) at pH 7.5
  Capturing and Binding buffer:
  10 mM Hepes, pH 7.5, 150 mM NaCl, 3 mM EDTA, 0.05% P20
Binding Assay of Purified Monomeric α-Synuclein-hexaHis to Immobilized Monoclonal Antibodies on the Capturing Antibody i) Immobilization of Goat Anti-Mouse Immunoglobulin IgG (Capture Antibody)

Immobilization of goat anti-mouse IgG (mouse antibody capture kit; Cat-No. BR-1008-38; GE Healthcare, Uppsala, Sweden) was performed in buffer containing 10 m M Hepes, 150 m M NaCl, 0.05% P20 at pH 7.5. In the first step the carboxyl groups of CM5 sensor chip surface were transformed to the reactive succinimide esters by contacting the sensor surface seven minutes with a solution of 0.2 M N-ethyl-N-dimethyl amino polycarbodiimide (EDC) and 0.05 M N-hydroxysuccinimide (NHS). After the activation, the sensor surface was contacted 3 min. with the goat anti-mouse IgG at 30 µg/ml in 10 mM sodium acetate buffer (pH 5.0). IgG was immobilized to the level of about 3000 RUs (response units). Finally, the excess of activated carboxylic groups on the surface was quenched with ethanolamine (1 M, pH 8.5, 7 min.).

ii) Capturing of Anti-Alpha Synuclein Antibodies

The monoclonal anti-alpha synuclein antibodies (100 nM solution in running buffer) were captured on the immobilized IgG antibody until an amount of captured antibody of 200-250 RUs was reached. One channel of the sensor chip was used with immobilized goat anti-mouse antibody as reference channel.

iii) Binding Experiment of Monomeric Alpha-Synuclein with an N-Terminal Hexa-Histidine Tag Binding experiment was performed in a buffer containing 10 mM Hepes, 150 mM NaCl, 3 mM EDTA, 0.05% P20 at pH 7.5. The purified monomeric alpha-synuclein-hexaHis was titrated up to 334 nM (5 points, dilution factor of 2) over the surface of captured monoclonal anti-alpha synuclein-antibodies. After each titration of purified monomeric alpha-synuclein-hexaHis, the complex of alpha-synuclein and monoclonal anti-alpha synuclein-antibody was removed from the chip with short pulses of a 10 mM glycine-HCl solution (pH 1.7). New monoclonal anti-alpha synuclein antibodies were captured on the chip surface thereafter.

b) Characterization of Monoclonal Anti-Alpha Synuclein-Antibodies Binding to Monomeric Alpha-Synuclein Immobilized Via his-Tag on a NTA (Nitrilotriacetic Acid) Chip
Buffers: Immobilization buffer:
  10 mM Hepes, 150 mM NaCl, 0.05% P20, pH 7.5
  Binding buffer:
  10 mM Hepes, pH 7.5, 150 mM NaCl, 3 mM EDTA, 0.05% P20 i) Immobilization of Purified Monomeric Alpha-Synuclein on NTA Sensor Surface

Immobilization of monomeric α-synuclein-hexaHis (N-terminal) on NTA (nitrilotriacetic acid) sensor surface was performed in running buffer containing 10 mM Hepes, 150 mM NaCl, 0.05% P20 at pH 7.5. NTA sensor surface was first washed three-times each for 1 min. with 0.35 M EDTA at a flow of 5 l/min. Thereafter, the sensor surface was loaded with $Ni^{2+}$-ions by a 1 min. contact of the chip surface with 500 μM $NiCl_2$ in running buffer and additionally activated for 7 min. with 0.2 M EDC and 0.05 M NHS solution. Furthermore, hexaHis labeled alpha-synuclein in running buffer (<0.1 μg/ml) was contacted with the sensor surface to achieve low density surface (up to 5 RUs) enabling further detection of monovalent binding of monoclonal anti-alpha synuclein-antibodies to alpha-synuclein. Finally, remaining groups of active ester were deactivated for 5 min. with 1 M Tris, pH 7.5. A flow channel without immobilized alpha-synuclein was used as a reference channel.

ii) Binding Assay with Monoclonal Antibodies with Immobilized α-Synuclein

Binding assay was performed in a buffer containing 10 mM Hepes, 150 mM NaCl, 3 mM EDTA, 0.05% P20 at pH 7.5. The monoclonal anti-alpha synuclein-antibodies were analyzed at single concentration of 100 nM for Yes/No binding response or were titrated in running buffer up to concentration of 100 nM (single injections of 5 concentrations with dilution factor of 2) to estimate binding kinetic and affinity to monomeric alpha-synuclein. After monitoring of binding curve for each concentration of each anti-alpha synuclein-antibody, the alpha-synuclein surface was regenerated with two short pulses of 100 mM phosphoric acid (2×1 min.) to wash off the bound antibody and enable monitoring of another antibody binding.

c) Characterization of Monoclonal Anti-Alpha Synuclein-Antibodies Binding to Monomeric Alpha-Synuclein Immobilized on DOPC:DOPS Liposomes on L1 Sensor Buffers: Immobilization and binding buffer:
    50 mM Hepes, 150 mM NaCl, pH 7.5 i) Preparation of DOPC:DOPS Liposomes 25 mg/ml (7:3 (w/w)) mixture of lipids DOPC:DOPS (1,2-dioleoyl-sn-glycero-3-phosphocholine:1,2-dioleoyl-sn-glycero-3-phospho-L-serine) in chloroform was evaporated in a glass flask with argon stream under vacuum hood to obtain lipid film on the flask wall. The lipid film was hydrated in Hepes buffer (50 mM Hepes, 150 mM NaCl, pH 7.5) to obtain a 5 mM buffer lipid solution. The lipid solution was extruded with Mini-Extruder (Avanti Polar Lipids, Alabaster, USA) by passing of the lipid solution 15 times through 100 nm extruder-filters to obtain liposomes solution. The quality and size of liposomes were proved by dynamic light scattering.

ii) Immobilization of Purified Monomeric α-Synuclein on DOPC:DOPS Liposomes

Immobilization of alpha-synuclein-hexaHis (N-terminal tag) on DOPC:DOPS liposomes was performed in a buffer containing 50 mM Hepes, 150 mM NaCl at pH 7.5. All flow channels of an L1 sensor surface were first washed 1 min. with a solution of 20 mM Chaps to obtain a stable baseline. The DOPC:DOPS liposome solution obtained by the extrusion was diluted 5-times in running buffer and loaded on the sensor surface of all flow channels to obtain immobilization levels of about 3000 RUs. All flow channels were blocked in the next step with BSA (bovine serum albumin) solution at 0.1 mg/ml to reduce nonspecific binding of alpha-synuclein on/to the sensor surface. Alpha-synuclein was diluted in running buffer to a concentration of 5.0 μg/ml and immobilized on liposomes to low density (<30 RUs) on the selected flow channels enabling detection of monovalent antibodies binding to alpha-synuclein. A flow channel with immobilized liposomes but without alpha-synuclein was used as a reference channel.

iii) Binding Assay with Monoclonal Antibodies to Immobilized Alpha-Synuclein on DOPC:DOPS Liposomes In the binding assay each antibody was analyzed at single concentration of 100 nM for Yes/No binding response or was titrated in running buffer over active and reference channels up to concentration of 100 nM (5 points with dilution factor of 2) to estimate binding kinetic and affinity to alpha-synuclein. After monitoring of antibody binding the sensor surface was regenerated for 1 min. with 20 mM Chaps and equilibrated with running buffer for the next immobilization of liposomes.

d) Characterization of Monoclonal Anti-Alpha Synuclein-Antibodies Binding to Alpha-Synuclein Preformed-Fibrils (PFF)

Buffers: Immobilization buffer:
    10 mM Hepes, 150 mM NaCl, 0.05% P20, pH 7.5
Binding buffer:
    10 mM Hepes, pH 7.5, 150 mM NaCl, 3 mM EDTA, 0.05% P20 i) Immobilization of α-Synuclein Preformed-Fibrils on NTA Sensor Surface

His-tag immobilization of alpha-synuclein PFF (containing N-terminally hexaHis-tag labeled alpha-synuclein and unlabeled alpha-synuclein in ratio 1:10) was performed on NTA sensor in running buffer containing 10 mM Hepes, 150 mM NaCl, 0.05% P20 at pH 7.5. NTA sensor surface was first washed 1 min. with a 0.35 M EDTA solution at a flow of 5 μl/min. Thereafter the sensor surface was loaded with $Ni^{2+}$-ions by 1 min. contact of the surface with 500 μM $NiCl_2$ solution in running buffer and additionally activated for 7 min. with 0.2 M EDC and 0.05 M NHS solution. Diluted solution of alpha-synuclein PFF in running buffer was contacted with the sensor surface to achieve various fibrils densities on the sensor surface (about 20 RUs, about 200 RUs and about 2000 RUs). Deactivation of remaining free groups of active ester was performed for 5 min. with 1 M Tris at pH 7.5. One of flow channels, where no alpha-synuclein fibrils were immobilized, was used as a reference channel.

ii) Binding Assay with Monoclonal Antibodies to Immobilized PFF

Binding of each anti-alpha-synuclein-antibody was monitored in the titration experiment up to a concentration of 100 nM (5 points, dilution factor of 2) on all four channels in parallel. After monitoring of the binding curve for each antibody, the alpha-synuclein PFF surface was regenerated with short pulses (2×1 min.) of 100 mM phosphoric acid to wash off the bound antibody.

Results:

The binding of different alpha-synuclein-antibodies as reported herein also as fusions with a blood-brain-barrier shuttle module and of certain reference antibodies as determined with SPR as described above is shown in the Table below.

TABLE

Binding of anti-alpha-synuclein antibodies to different alpha-synuclein forms.

| antibody | binding to monomeric alpha-synuclein antibody immobilzed | binding to monomeric alpha-synuclein synuclein immobilized | binding to monomeric alpha-synuclein in liposomes | binding to alpha-synuclein preformed fibrils |
|---|---|---|---|---|
| 0017 | Yes | Yes | Yes | Yes |
| 0018 | No | No | No | Yes |
| 0070 | not tested | Yes | not tested | Yes |
| 0076 | not tested | No | not tested | Yes |

TABLE-continued

Binding of anti-alpha-synuclein antibodies to different alpha-synuclein forms.

| antibody | binding to monomeric alpha-synuclein antibody immobilzed | binding to monomeric alpha-synuclein immobilized | binding to monomeric alpha-synuclein in liposomes | binding to alpha-synuclein preformed fibrils |
|---|---|---|---|---|
| 0081 | not tested | No | not tested | Yes |
| sc211 (reference) | Yes | Yes | Yes | Yes |
| 12F4 (reference) | No | No | No | Yes |
| 12F4-shuttle (reference) | not tested | Yes | not tested | Yes |
| 4B12 (reference) | Yes | Yes | Yes | Yes |
| syn1 (reference) | Yes | Yes | Yes | Yes | antibody 0070 is the blood-brain-barrier shuttle fusion of antibody 0017 with the scFv of the anti-transferrin receptor-antibody 8D3;

antibody 0076 is the blood-brain-barrier shuttle fusion of antibody 0018 with the scFv of the anti-transferrin receptor-antibody 8D3.

Example 10

Immunohistochemistry Analysis and Cytotoxicity Assays

Immunohistochemistry Analysis of PD Brain Sections

Cryosections (10 μm) of human Parkinson Disease patient brain were stained with 5.0 μg/ml primary IgG of antibody 0017, antibody 0018 or antibody 0057 (murine Fc) and counterstained with 5.0 μg/ml rabbit anti-alpha-synuclein antibody (Cell Signaling; Cat. No. 2628S).

As secondary antibodies, Alexa Fluor 488 conjugated goat anti-mouse IgG antibody (H+L) (Invitrogen, Cat. No. A11001) and Alexa Fluor 594 conjugated goat anti-rabbit IgG antibody (H+L) (high cross-adsorbed, Invitrogen, Cat. No. A11037) were used.

Specimens were imaged on a LEICA confocal microscope (SP5x) using 63× lens 1.2NA, 1.6× Zoom, Pinhole @ 1.0AU.

Alexa 488 was excited @ 497 nm (10% WLL); Emission@505-571 nm (98% HyD).

Alexa 594 was excited @ 590 nm (8% WLL); Emission@596-680 nm (92% HyD). Images were averaged by 5× line averaging.

Figure 12:
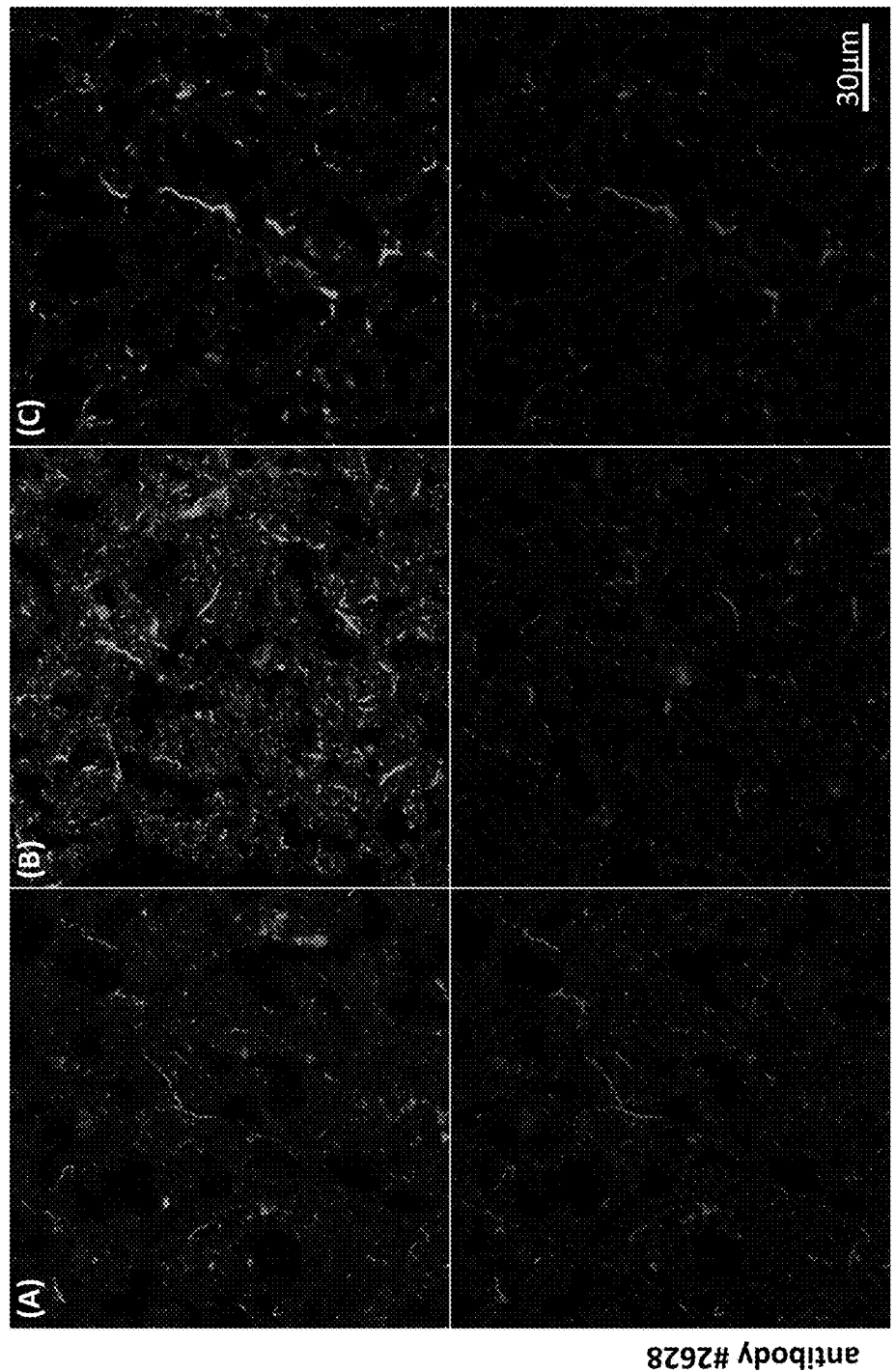
FIG. 12: Confocal microscopy analysis of immunohistochemically analyzed cryosections of Parkinson's Disease patient's brain sections (identical setting for all images): (A) antibody 0017, (B) antibody 0018, (C) 12F4 reference antibody.

Results see FIG. 12.

Human Neuronal Cell (LUHMES) Functional Cell Model for Alpha Synuclein Mediated Toxicity Protection by Therapeutic Antibodies LUHMES cells were differentiated for 5 days in 384 well plates as described in detail below. 24 h after seeding conditioned cell culture supernatants from SHSY5Y cells growing in LUHMES differentiation media were added to the plates at a 1:1 dilution to induce exosomal mediated alpha-synuclein toxicity. Control cultures received LUHMES differentiation media. Antibodies to be tested were added together with conditioned SHSY5Y media at a final concentration of 10 μg/ml. Cell viability was determined after additional 4 days by CellTiterGlo assay (Promega, Cat. No. REF G7571). Viability values are displayed as CPS counts.

Cell Culture Methods

Coating, Medium and Additives:

Poly-L-Ornithine: Sigma-Aldrich, Cat. No. P-3655-100 mg

Fibronectin (solution): Sigma-Aldrich, Cat. No. F-1141-5 mg

Advanced DMEM/F-12: Gibco/Invitrogen, Cat. No. 12634-010

N-2: Gibco/Invitrogen, Cat. No. 17502048 or PAA F005-004

L-Glutamine: Sigma-Aldrich, Cat. No. G7513

FGF: R&D Systems, Cat. No. 4114-TC (1 mg)

GDNF: R&D Systems, Cat. No. 212-GD (50 pig)

Tetracycline: Sigma-Aldrich, Cat. No. T-7660 cAMP: Sigma-Aldrich, Cat. No. D0627

LUHMES Culture and Differentiation:

Coating (all plates and flasks have to be Nunclon):

| Coating | 5 ml | 7 ml | 10 ml | 14 ml | 20 ml |
|---|---|---|---|---|---|
| Milli Q H$_2$O | 4.75 ml | 6.65 ml | 9.5 ml | 13.3 ml | 19 ml |
| PLO (1 mg/ml) | 250 μl | 350 μl | 500 μl | 700 μl | 1000 μl |
| Fibronectin (1 mg/ml) | 5 μl | 7 μl | 10 μl | 14 μl | 20 l |

The coating Solution was filled into plates and flasks (T75 Flask: 7 ml; T175 Flask: 14 ml; 96-well Platte: 50 μl per Well, 24-well-plate: 250 μl per well, 12 well-plate: 500 μl per well, 6 well-plate: 1 ml per well). The plates and flasks were incubated for at least 3 h (or overnight) at 37° C. After incubation the coating-solution was aspirated. Flasks were washed twice with Milli Q water. Before usage the plates and flasks were dried under the laminar flow bench.

Proliferation-Medium:

| Proliferation-medium | 10 ml | 20 ml | 30 ml | 40 ml | 50 ml |
|---|---|---|---|---|---|
| Advanced DMEM/F12 | 9.8 ml | 19.6 ml | 29.4 ml | 39.2 ml | 49 ml |
| L-Gln (200 mM) | 100 μl | 200 μl | 300 μl | 400 μl | 500 μl |
| N2 (100×) | 100 μl | 200 μl | 300 μl | 400 μl | 500 μl |
| FGF (160 μg/ml) | 2.5 μl | 5 μl | 7.5 μl | 10 μl | 12.5 μl |

Differentiation-Medium:

| Differentiation-medium | 10 ml | 20 ml | 30 ml | 40 ml | 50 ml |
|---|---|---|---|---|---|
| Advanced DMEM/F12 | 9.7 ml | 19.4 ml | 29.1 ml | 38.8 ml | 48.5 ml |
| L-Gln (200 mM) | 100 μl | 200 μl | 300 μl | 400 μl | 500 μl |
| N2 (100×) | 100 μl | 200 μl | 300 μl | 400 μl | 500 μl |
| cAMP (100 mM) | 100 μl | 200 μl | 300 μl | 400 μl | 500 μl |
| Tetracycline (1 mg/ml) | 10 μl | 20 μl | 30 μl | 40 μl | 50 μl |
| GDNF (20 μg/ml) | 1 μl | 2 μl | 3 μl | 4 μl | 5 μl |

Subculture:

Cells that were cultivated in a 75 cm$^2$ flask in proliferation-medium were splitted when they reached 80% of confluence. First the cells were washed twice with 10 ml of PBS. Then 4 ml of ATV-Trypsin was added (2 ml of the 2×ATV-Trypsin stock solution is mixed before with 2 ml of PBS). The cells were incubated for 3 min. at 37° C. When cells were detached 21 ml Advanced DMEM/F12 medium without additives was added. The cell-suspension was centrifuged in a 50 ml Falcon tube at 300×g for 5 min. The supernatant was removed and the cells were resuspended in 5 ml of Advanced DMEM/F12 medium without additives. The cells were counted in a Neubauer-chamber.

For subculture the cells were splitted after 2, 3 or 4 d. If the aim is two days, $2*10^6$ cells (splitting 1:5) were seeded into a 75 cm² flask. For a 3 day-culture $1*10^6$ cells (splitting 1:10) and for a four day-culture 500,000 cells (splitting 1:20) are enough. Cells were seeded into a 75 cm² flask containing 10 ml of proliferation-medium.

Pre-Differentiation:

The pre-differentiation of LUHMES cells took place in a 175 cm² flask. Therefore $6*10^6$ cells were seeded into 20 ml of proliferation medium. After 24 h of attachment and proliferation the medium was exchanged. Proliferation medium was replaced by differentiation medium. After an additional 48 h the pre-differentiation was finished.

Cells were seeded into multi-well plates. Therefore the medium was aspirated. Cells were washed twice with 10 ml of PBS. Thereafter 8 ml of ATV-Trypsin (4 ml of 2×ATV-trypsin stock solution was mixed before with 4 ml of PBS) was added. Cells were incubated for 3 to 5 min. at 37° C. 42 ml Advanced DMEM/F12 without additives was added. The cell-suspension was centrifuged in a 50 ml Falcon tube at 300×g for 5 min. The supernatant was removed and the cells were resuspended in 10 ml of differentiation medium. Cells were counted in a Neubauer-chamber.

Differentiation:

Further differentiation was carried out in coated cell culture plates.

| Cell culture plate | 6 well | 12 well | 24 well | 48 well | 96 well |
|---|---|---|---|---|---|
| Growth area [cm²] | 9.6 | 3.5 | 1.9 | 1.1 | 0.33 |
| Volume of medium | 2 ml | 1 ml | 500 μl | 300 μl | 100 μl |
| Cell number per well [*1000] | 1000 | 500 | 200-250 | 100-150 | 30-50 |

Figure 9:
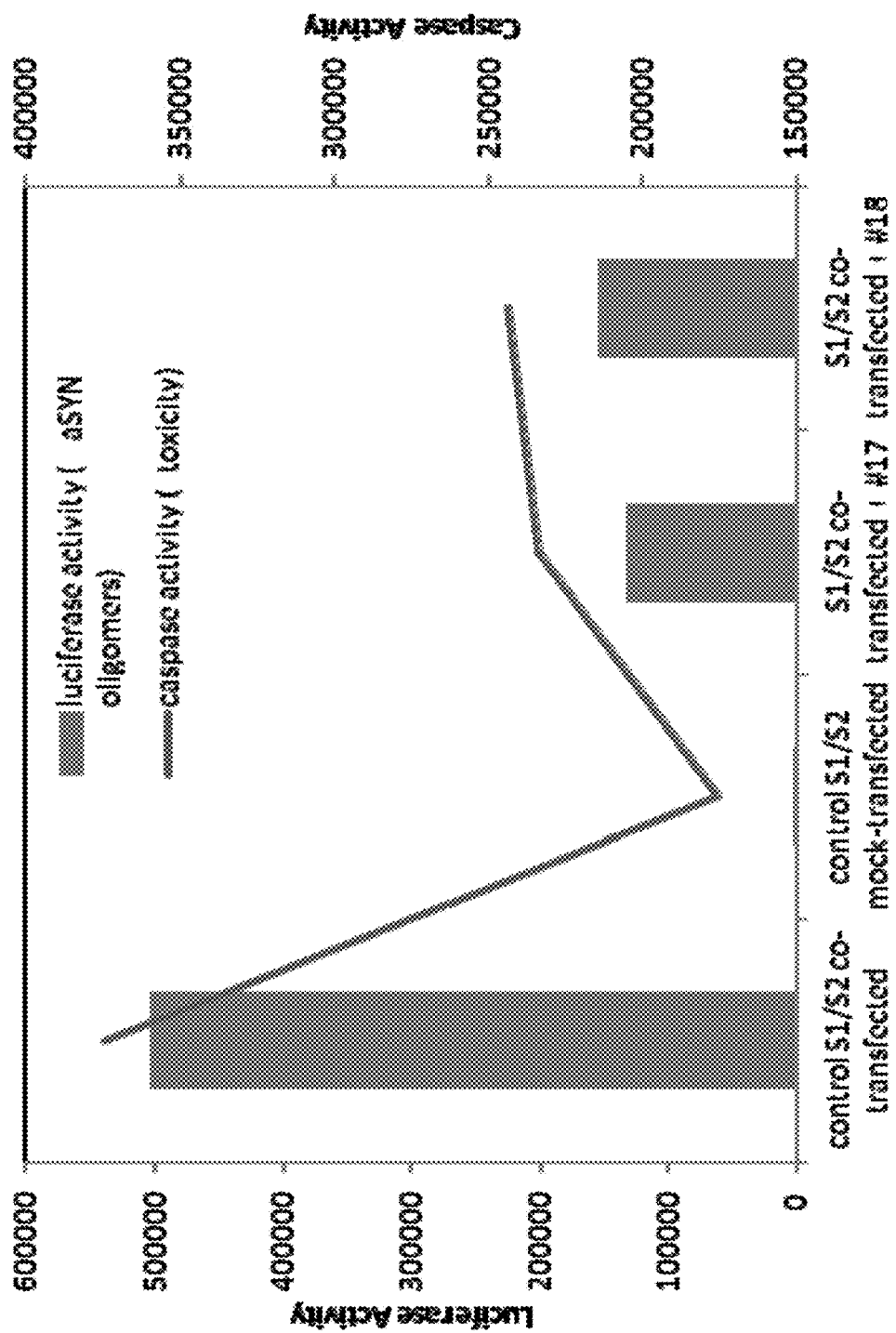
FIG. 9: Antibodies 0017 and 0018 are able to immunodeplete alpha-synuclein oligomers from extracellular media and thereby these antibodies reduce toxicity of alpha-synuclein oligomers.

The cells were diluted with differentiation medium and seeded with the proper volume of differentiation medium into the cell culture plates. After an additional 72 h differentiation is completed. For results see FIGS. 7 and 9.

Example 11

Thermal Stability

The denaturation points (melting points, $T_m$) of the monoclonal anti-alpha-synuclein antibodies (2 μM) were determined by a thermal shift assay using Sypro Orange as reporter fluorophore.

Figure 10:
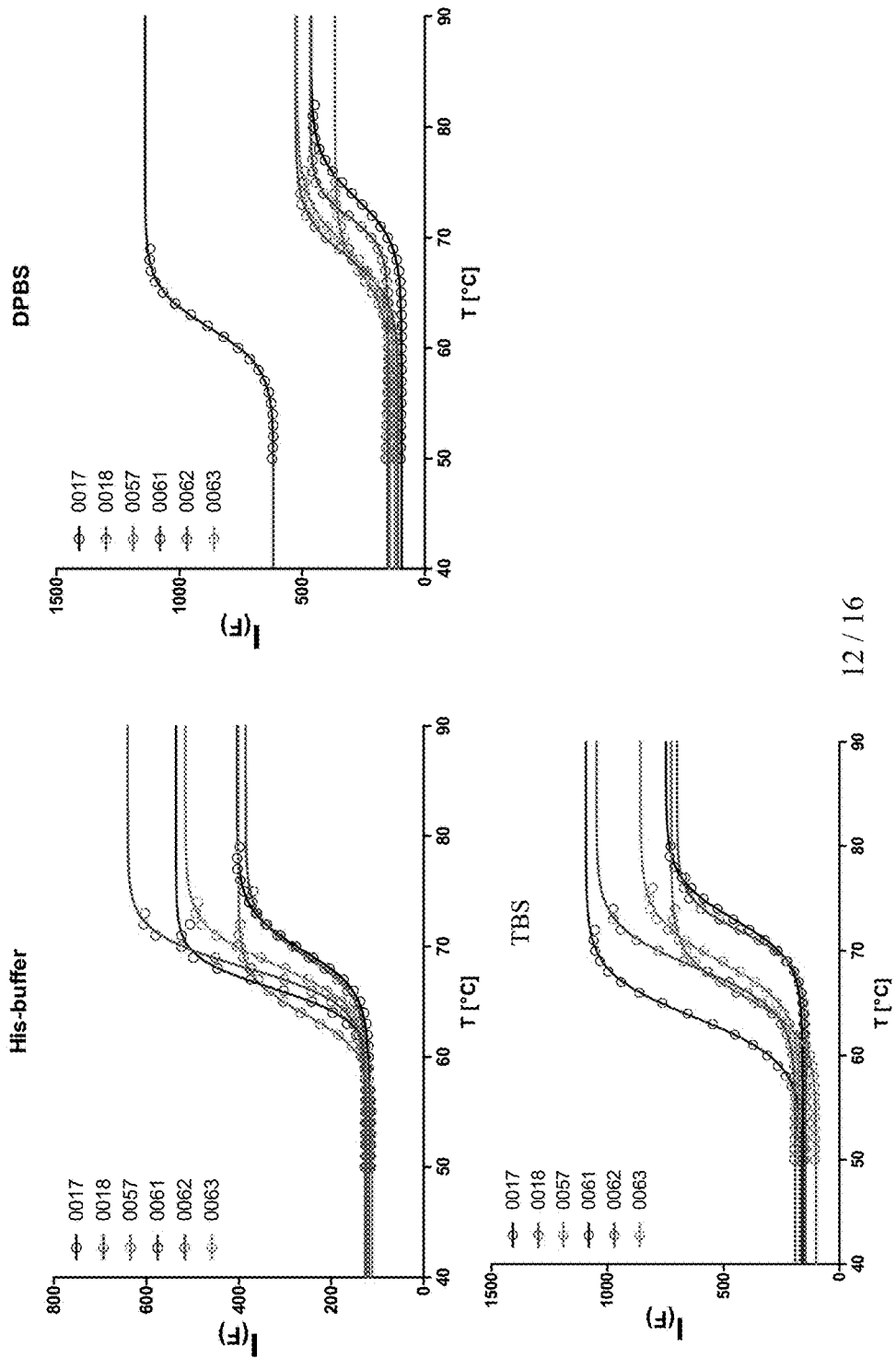
FIG. 10: Raw data of the melting transition (open circles, 40° C. —highest values) and corresponding fits (solid lines) as determined according to Example 11.

The melting transitions were fitted with a Boltzmann sigmoidal equation and the inflection point at half-maximum signal amplitude was defined as the melting temperature $T_m$, where half of the antibody is denatured (FIG. 10). $T_m$-values between 60° C. and 75° C. were determined.

TABLE melting points ($T_m$) of selected anti-alpha-synuclein antibodies

| | $T_m$ [° C.] | | |
|---|---|---|---|
| mAb | His-buffer | DPBS | TBS |
| 0017 | 69.7 | 73.6 | 73.0 |
| 0018 | 69.2 | 71.9 | 71.8 |
| 0057 | 63.9 | 66.6 | 65.7 |

Example 12

Epitope Mapping

Epitope Mapping was performed on custom made PepStar™ peptide microarrays, provided by JPT Peptide Technologies. Peptide sequences had a length of 15 amino acid residues and were designed to cover the whole sequence of human alpha-synuclein (UniProt accession number: P37840). Neighboring peptides had an overlapping sequence of 11 amino acids. Additional peptides comprise sequences with known sites of disease-relevant alpha-synuclein mutations (A30P, A53T, E57K) and sequences to assess cross-reactivity to rodent alpha-synuclein. Furthermore, 12 peptides/proteins were spotted which serve as controls for reactivity and specificity of primary and secondary antibodies. Proteins were as follows: Bovine Serum albumin, human IgG, rabbit IgG, mouse IgG, human tau protein, human alpha-synuclein, human beta-synuclein, human gamma-synuclein, human IgM, mouse IgM, phospho-Tyrosine peptide, human alpha-triple proline mutated-synuclein (A30P, A56P, A76P).

Epitope Mapping was performed according to manufacturer's instructions.

TABLE

Data of selected anti-alpha-synuclein-antibodies according to peptide mapping.

| antibody | epitope |
|---|---|
| 0017 | aa97-111: KDQLGKNEEGAPQEG |
| | aa101-15: GKNEEGAPQEGILED |
| | linear epitope, no species and |
| | isoform cross-reactivity |
| | predicted |
| 0018 | no peptide detected, |
| | detection of TP synuclein |
| 12F4 (reference antibody) | no peptide detected, |
| | detection of TP synuclein |
| syn211 (reference antibody) | aa113-127: LEDMPVDPDNEAYEM |
| | aa117-:131 PVDPDNEAYEMPSEE |
| | detection of TP synuclein |

Example 13

Acute In Vivo Labeling of Alpha-Synuclein Pathology by Anti-Alpha Synuclein Antibody-Blood-Brain-Barrier Shuttle Module Conjugates Study Design Three groups of 15-month-old Thy1-(A30P)alpha-synuclein transgenic mice (Kahle mice; n=3 per group) and wild-type controls (n=1 per group) were injected with three different anti-alpha synuclein-antibody-blood-brain-barrier shuttle module conjugates:
    antibody 0070→antibody 0017-scFab8D3 conjugate
    antibody 0076→antibody 0018-scFab8D3 conjugate
    reference→12F4-scFab8D3 conjugate
One transgenic mouse and one wild-type mouse were included as non-injected control. The study encompassed a total of 14 mice.

Staining/Detection of Bound mAb-Brain Shuttle in the Brain Tissue

Target occupancy in the brain was detected with an AF555-taged anti-huIgG-antibody on 20 m cryostat brain sections (4 per mouse; acetone fixed, blocked with NGS). A co-staining was performed: blood vessels (anti-podocalyxin, AF647); DAPI.

Result

Parenchyma of brain stem: varies from large neuritic/alpha-synuclein accumulated structures to diffuse punctate staining similar to a synaptic staining.

Neuritic pathology (=the major pathological feature in this mouse model) is restricted to brain stem and is highly variable from mouse to mouse.

Entire brain and also in non-transgenic mice: mostly punctate staining; similar to a synaptic staining.

Figure 11:
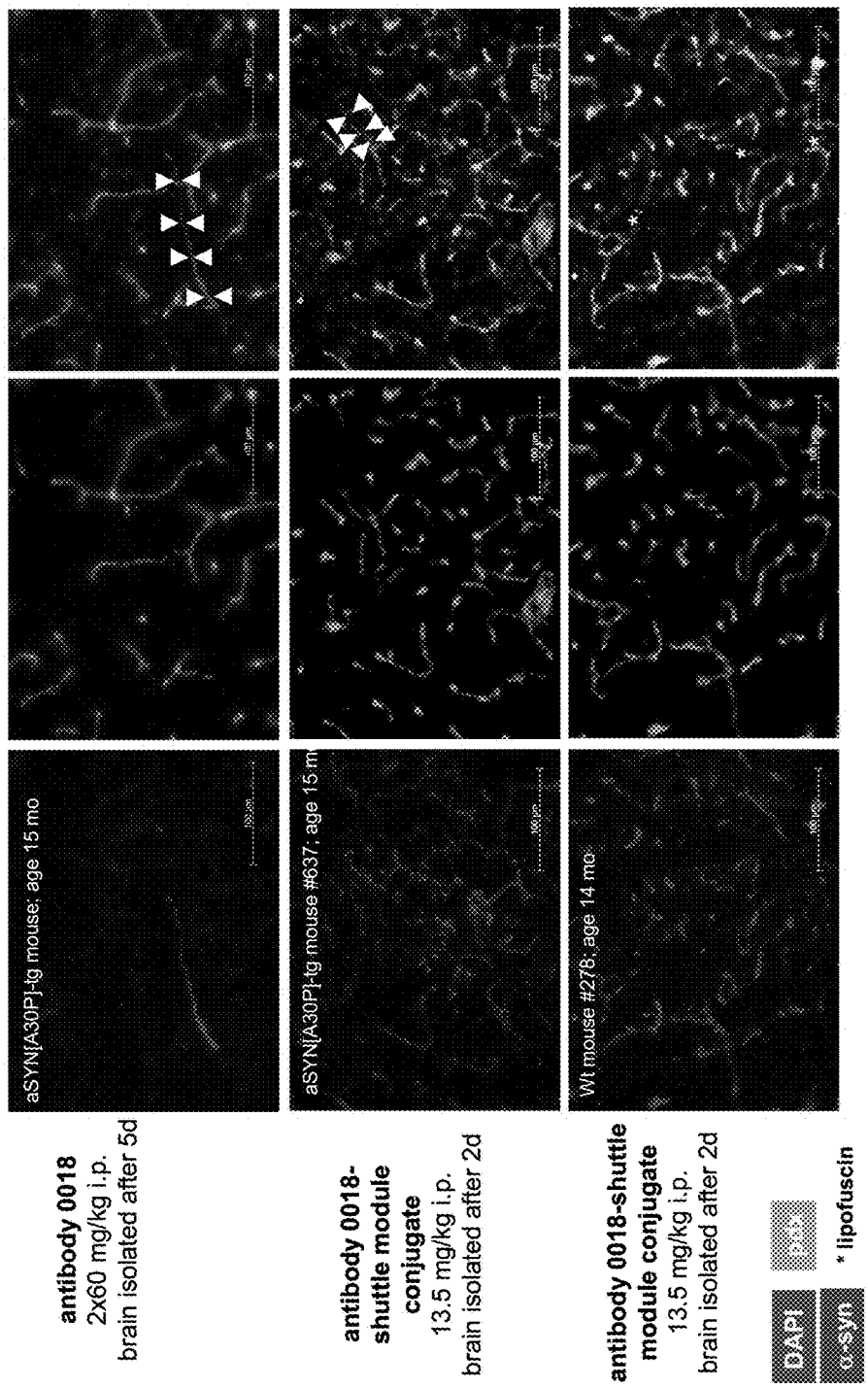
FIG. 11: Labeling of brain alpha-synuclein pathology, vasculature, and parenchyma in alpha-synuclein mutant A30P transgenic mice upon acute peripheral injection of an anti-alpha synuclein-antibody-blood-brain-barrier shuttle module conjugate.

See FIG. 11.

Example 14

CelluSpots™ Synthesis and Epitope Mapping

The peptide array for epitope analysis of antibody 0018 was prepared by employing the Intavis CelluSpots™ technology. In this approach, peptides were synthesized with an automated synthesizer (Intavis MultiPep RS) on modified cellulose disks which are dissolved after synthesis. The solutions of the individual peptides that remain covalently linked to macromolecular cellulose were then spotted onto coated microscope slides. The CelluSpots™ synthesis was carried out stepwise utilizing 9-fluorenylmethoxycarbonyl (Fmoc) chemistry on amino-modified cellulose disks in a 384-well synthesis plate. In each coupling cycle, the corresponding amino acids were activated with a solution of DIC/HOBt in DMF. Between coupling steps, non-reacted (i.e. free) amino groups were capped with a mixture of acetic anhydride, diisopropylethyl amine and 1-hydroxybenzotriazole. Upon completion of the synthesis, the cellulose disks were transferred to a 96-well plate and treated with a mixture of trifluoroacetic acid (TFA), dichloromethane, triisopropylsilane (TIS) and water for side chain deprotection. After removal of the cleavage solution, the cellulose bound peptides are dissolved with a mixture of TFA, TFMSA (trifluoro ethanesulfonic acid), TIS and water, precipitated with diisopropyl ether and re-suspended in DMSO. These peptide solutions were subsequently spotted onto Intavis CelluSpots™ slides using an Intavis slide spotting robot.

For epitope analysis, the prepared slides were washed with ethanol and thereafter with TBS (TRIS-buffered saline solution; 50 mM Tris, 137 mM NaCl, 2.7 mM KCl, pH 8) before a blocking step was carried out for 16 hours at 4° C. with 5 mL 10× Western Blocking Reagent (Roche Diagnostics GmbH, Mannheim, Germany), 2.5 g sucrose in TBS, 0.1% Tween-20. After washing with TBS-T (TBS+0.1% Tween-20), the slides were incubated with a solution (1 µg/mL) of antibody 0018 in TBS comprising 0.1% Tween-20 at ambient temperature for 2 hours. After washing, the slides were incubated for detection with an anti-mouse or anti-rabbit secondary antibody conjugated to horseradish peroxidase (HRP) (1:20000 in TBS-T) followed by incubation with DAB (3,3'-diaminobenzidine) substrate/peroxide buffer (Roche Diagnostics GmbH, Mannheim, Germany). ELISA-positive SPOTs were quantified and through assignment of the corresponding peptide sequences the antibody binding epitopes were identified.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A monoclonal antibody comprising a heavy chain variable domain comprising a CDRH1 sequence, a CDRH2 sequence, and a CDRH3 sequence, wherein the CDRH1 sequence is SEQ ID NO: 28, the CDRH2 sequence is SEQ ID NO: 29 or 34, and the CDRH3 sequence SEQ ID NO: 30, and a light chain variable domain comprising a CDRL1 sequence, a CDRL2 sequence, and a CDRL3 sequence, wherein the CDRL1 sequence is SEQ ID NO: 31 or 35, the CDRL2 sequence is SEQ ID NO: 32 or 36; and the CDRL3 sequence is SEQ ID NO: 33 or 37.

2. The antibody according to claim 1, wherein the antibody binds to alpha-synuclein that is monomeric or oligomeric alpha-synuclein.

3. The antibody according to claim 1, wherein the antibody is a humanized antibody or a chimeric antibody.

4. The antibody according to claim 1, wherein the antibody is conjugated to a blood-brain-barrier shuttle module, wherein the blood-brain-barrier shuttle module is an antibody or antibody fragment that binds to LRP1, LRP8, human transferrin receptor or human insulin-like growth factor receptor.

5. The antibody according to claim 1, wherein the antibody further comprises:

a) an Fc region of an immunoglobulin heavy chain of human subclass IgG1, b) an Fc region of an immunoglobulin heavy chain of human subclass IgG4, c) an Fc region of an immunoglobulin heavy chain of human subclass IgG1 with amino acid residue substitutions L234A, L235A and P329G, d) an Fc region of an immunoglobulin heavy chain of human subclass IgG4 with amino acid residue substitutions S228P, L235E and P329G, e) a first Fc region of an immunoglobulin heavy chain of human subclass IgG1 with amino acid residue substitutions L234A, L235A, P329G, T366W and S354C and a second Fc region of an immunoglobulin heavy chain of human subclass IgG1 with amino acid residue substitutions L234A, L235A, P329G, T366S, L368A, Y407V and Y349C, or f) a first Fc region of an immunoglobulin heavy chain of human subclass IgG4 with amino acid residue substitutions S228P, L235E, P329G, T366W and S354C and a second Fc region of an immunoglobulin heavy chain of human subclass IgG4 with amino acid residue substitutions S228P, L235E, P329G, T366S, L368A, Y407V and Y349C.

6. A pharmaceutical formulation comprising the antibody according to claim 1 and a pharmaceutically acceptable carrier.

7. A method for treating synucleinopathy, said method comprising administering an antibody of claim 1 to a subject in need thereof.

8. A method for treating Parkinson's Disease said method comprising administering an antibody of claim 1 to a subject in need thereof.

* * * * *

SEQUENCE LISTING

```
<160> NUMBER OF SEQ ID NOS: 58

<210> SEQ ID NO 1
<211> LENGTH: 11
<212> TYPE: PRT
<213> ORGANISM: Artificial Sequence
<220> FEATURE:
<223> OTHER INFORMATION: human alpha-synuclein fragment

<400> SEQUENCE: 1

Gly Lys Asn Glu Glu Gly Ala Pro Gln Glu Gly
1               5                   10

<210> SEQ ID NO 2
<211> LENGTH: 4
<212> TYPE: PRT
<213> ORGANISM: Artificial Sequence
<220> FEATURE:
<223> OTHER INFORMATION: CDRH1

<400> SEQUENCE: 2

Tyr Ala Met Ile
1
```

```
<210> SEQ ID NO 3
<211> LENGTH: 9
<212> TYPE: PRT
<213> ORGANISM: Artificial Sequence
<220> FEATURE:
<223> OTHER INFORMATION: CDRH2

<400> SEQUENCE: 3

Pro Ser Gly Asn Thr Tyr Tyr Ala Asn
1               5

<210> SEQ ID NO 4
<211> LENGTH: 10
<212> TYPE: PRT
<213> ORGANISM: Artificial Sequence
<220> FEATURE:
<223> OTHER INFORMATION: CDRH3

<400> SEQUENCE: 4

Arg Asp Gly Thr Asp Lys Thr Phe Asn Ile
1               5                   10

<210> SEQ ID NO 5
<211> LENGTH: 6
<212> TYPE: PRT
<213> ORGANISM: Artificial Sequence
<220> FEATURE:
<223> OTHER INFORMATION: CDRL1

<400> SEQUENCE: 5

Asn Val Tyr Gly Asp Asn
1               5

<210> SEQ ID NO 6
<211> LENGTH: 6
<212> TYPE: PRT
<213> ORGANISM: Artificial Sequence
<220> FEATURE:
<223> OTHER INFORMATION: CDRL2

<400> SEQUENCE: 6

Glu Ala Ser Lys Leu Ala
1               5

<210> SEQ ID NO 7
<211> LENGTH: 10
<212> TYPE: PRT
<213> ORGANISM: Artificial Sequence
<220> FEATURE:
<223> OTHER INFORMATION: CDRL3

<400> SEQUENCE: 7

Gly Glu Phe Leu Cys Thr Thr Ser Asp Cys
1               5                   10

<210> SEQ ID NO 8
<211> LENGTH: 5
<212> TYPE: PRT
<213> ORGANISM: Artificial Sequence
<220> FEATURE:
<223> OTHER INFORMATION: CDRH1

<400> SEQUENCE: 8

Ser Tyr Ala Met Ile
1               5
```

```
<210> SEQ ID NO 9
<211> LENGTH: 16
<212> TYPE: PRT
<213> ORGANISM: Artificial Sequence
<220> FEATURE:
<223> OTHER INFORMATION: CDRH2

<400> SEQUENCE: 9

Val Ile Tyr Pro Ser Gly Asn Thr Tyr Tyr Ala Asn Trp Ala Lys Gly
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: CDRL1

<400> SEQUENCE: 10

Gln Ala Ser Gln Asn Val Tyr Gly Asp Asn Tyr Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDRL2

<400> SEQUENCE: 11

Glu Ala Ser Lys Leu Ala Ser
1               5

<210> SEQ ID NO 12
<211> LENGTH: 13
<212> TYPE: PRT
<213> ORGANISM: Artificial Sequence
<220> FEATURE:
<223> OTHER INFORMATION: CDRL3

<400> SEQUENCE: 12

Gln Gly Glu Phe Leu Cys Thr Thr Ser Asp Cys Phe Thr
1               5                   10

<210> SEQ ID NO 13
<211> LENGTH: 115
<212> TYPE: PRT
<213> ORGANISM: Artificial Sequence
<220> FEATURE:
<223> OTHER INFORMATION: heavy chain variable domain

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Ile Asn Ser Tyr Ala
                20                  25                  30

Met Ile Trp Val Arg Gln Ala Pro Gly Glu Gly Leu Glu Trp Ile Gly
            35                  40                  45

Val Ile Tyr Pro Ser Gly Asn Thr Tyr Tyr Ala Asn Trp Ala Lys Gly
        50                  55                  60

Arg Phe Thr Val Ser Arg Thr Ser Thr Val Asp Leu Lys Ile Thr
65                  70                  75                  80

Ser Pro Thr Thr Glu Asp Thr Ala Thr Tyr Phe Cys Ala Arg Arg Asp
                85                  90                  95
```

```
Gly Thr Asp Lys Thr Phe Asn Ile Trp Gly Pro Gly Thr Leu Val Thr
                100                 105                 110

Val Ser Leu
        115

<210> SEQ ID NO 14
<211> LENGTH: 112
<212> TYPE: PRT
<213> ORGANISM: Artificial Sequence
<220> FEATURE:
<223> OTHER INFORMATION: light chain variable domain

<400> SEQUENCE: 14

Gln Val Leu Thr Gln Thr Pro Ser Pro Val Ser Ala Ala Val Gly Gly
1               5                   10                  15

Thr Val Thr Ile Asn Cys Gln Ala Ser Gln Asn Val Tyr Gly Asp Asn
            20                  25                  30

Tyr Leu Ala Trp Tyr Gln Gln Lys Pro Gly Gln Pro Pro Lys Leu Leu
        35                  40                  45

Ile Tyr Glu Ala Ser Lys Leu Ala Ser Gly Val Pro Pro Arg Phe Ser
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Gln Gly Glu Phe Leu Cys Thr
                85                  90                  95

Thr Ser Asp Cys Phe Thr Phe Gly Gly Gly Thr Gly Val Val Val Arg
                100                 105                 110

<210> SEQ ID NO 15
<211> LENGTH: 3
<212> TYPE: PRT
<213> ORGANISM: Artificial Sequence
<220> FEATURE:
<223> OTHER INFORMATION: CDRH1

<400> SEQUENCE: 15

Arg Tyr Ala
1

<210> SEQ ID NO 16
<211> LENGTH: 5
<212> TYPE: PRT
<213> ORGANISM: Artificial Sequence
<220> FEATURE:
<223> OTHER INFORMATION: CDRH2

<400> SEQUENCE: 16

Asn Ser Ser Gly Ala
1               5

<210> SEQ ID NO 17
<211> LENGTH: 14
<212> TYPE: PRT
<213> ORGANISM: Artificial Sequence
<220> FEATURE:
<223> OTHER INFORMATION: CDRH3

<400> SEQUENCE: 17

Trp Thr Tyr Asp Asp Tyr Gly Asp Phe Gln Gly Phe Asn Ile
1               5                   10

<210> SEQ ID NO 18
<211> LENGTH: 9
```

```
<212> TYPE: PRT
<213> ORGANISM: Artificial Sequence
<220> FEATURE:
<223> OTHER INFORMATION: CDRL1

<400> SEQUENCE: 18

Ser Val Tyr Asn Asn Asp Leu Ala
1               5

<210> SEQ ID NO 19
<211> LENGTH: 6
<212> TYPE: PRT
<213> ORGANISM: Artificial Sequence
<220> FEATURE:
<223> OTHER INFORMATION: CDRL2

<400> SEQUENCE: 19

Arg Ala Ser Lys Leu Ala
1               5

<210> SEQ ID NO 20
<211> LENGTH: 11
<212> TYPE: PRT
<213> ORGANISM: Artificial Sequence
<220> FEATURE:
<223> OTHER INFORMATION: CDRL3

<400> SEQUENCE: 20

Gly Gly Tyr Asp Asp Asp Ala Asp Met Gly Ala
1               5                   10

<210> SEQ ID NO 21
<211> LENGTH: 5
<212> TYPE: PRT
<213> ORGANISM: Artificial Sequence
<220> FEATURE:
<223> OTHER INFORMATION: CDRH1

<400> SEQUENCE: 21

Arg Tyr Ala Met Ser
1               5

<210> SEQ ID NO 22
<211> LENGTH: 16
<212> TYPE: PRT
<213> ORGANISM: Artificial Sequence
<220> FEATURE:
<223> OTHER INFORMATION: CDRH2

<400> SEQUENCE: 22

Val Ile Asn Ser Ser Gly Ala Thr Tyr Tyr Ala Ser Trp Ala Lys Gly
1               5                   10                  15

<210> SEQ ID NO 23
<211> LENGTH: 13
<212> TYPE: PRT
<213> ORGANISM: Artificial Sequence
<220> FEATURE:
<223> OTHER INFORMATION: CDRL1

<400> SEQUENCE: 23

Gln Ser Ser Gln Ser Val Tyr Asn Asn Asn Asp Leu Ala
1               5                   10

<210> SEQ ID NO 24
<211> LENGTH: 7
<212> TYPE: PRT
```

<213> ORGANISM: Artificial Sequence
<220> FEATURE:
<223> OTHER INFORMATION: CDRL2

<400> SEQUENCE: 24

Arg Ala Ser Lys Leu Ala Ser
1               5

<210> SEQ ID NO 25
<211> LENGTH: 12
<212> TYPE: PRT
<213> ORGANISM: Artificial Sequence
<220> FEATURE:
<223> OTHER INFORMATION: CDRL3

<400> SEQUENCE: 25

Leu Gly Gly Tyr Asp Asp Ala Asp Met Gly Ala
1               5                   10

<210> SEQ ID NO 26
<211> LENGTH: 119
<212> TYPE: PRT
<213> ORGANISM: Artificial Sequence
<220> FEATURE:
<223> OTHER INFORMATION: heavy chain variable domain

<400> SEQUENCE: 26

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Tyr Ala
                20                  25                  30

Met Ser Trp Val Arg Gln Ala Pro Gly Lys Gly Leu Glu Trp Ile Gly
            35                  40                  45

Val Ile Asn Ser Ser Gly Ala Thr Tyr Tyr Ala Ser Trp Ala Lys Gly
        50                  55                  60

Arg Phe Thr Ile Ser Glu Thr Ser Thr Thr Val Glu Leu Lys Ile Thr
65                  70                  75                  80

Ser Pro Thr Thr Glu Asp Thr Ala Thr Tyr Phe Cys Ala Arg Trp Thr
                85                  90                  95

Tyr Asp Asp Tyr Gly Asp Phe Gln Gly Phe Asn Ile Trp Gly Pro Gly
            100                 105                 110

Thr Leu Val Thr Val Ser Leu
        115

<210> SEQ ID NO 27
<211> LENGTH: 111
<212> TYPE: PRT
<213> ORGANISM: Artificial Sequence
<220> FEATURE:
<223> OTHER INFORMATION: light chain variable domain

<400> SEQUENCE: 27

Ala Val Leu Thr Gln Thr Pro Ser Pro Val Ser Ala Ala Val Gly Gly
1               5                   10                  15

Thr Val Thr Ile Ser Cys Gln Ser Ser Gln Ser Val Tyr Asn Asn Asn
                20                  25                  30

Asp Leu Ala Trp Tyr Gln Gln Lys Pro Gly Gln Pro Pro Lys Leu Leu
            35                  40                  45

Ile Tyr Arg Ala Ser Lys Leu Ala Ser Gly Val Pro Ser Arg Phe Lys
        50                  55                  60

Gly Ser Gly Ser Gly Thr Gln Phe Thr Leu Thr Ile Ser Gly Val Gln

```
            65                  70                  75                  80
Cys Asp Asp Ala Ala Thr Tyr Tyr Cys Leu Gly Gly Tyr Asp Asp
                    85                  90                  95
Ala Asp Met Gly Ala Phe Gly Gly Thr Glu Val Val Lys
                100                 105                 110

<210> SEQ ID NO 28
<211> LENGTH: 5
<212> TYPE: PRT
<213> ORGANISM: Artificial Sequence
<220> FEATURE:
<223> OTHER INFORMATION: CDRH1

<400> SEQUENCE: 28

Arg Asp Thr Met Ile
1               5

<210> SEQ ID NO 29
<211> LENGTH: 10
<212> TYPE: PRT
<213> ORGANISM: Artificial Sequence
<220> FEATURE:
<223> OTHER INFORMATION: CDRH2

<400> SEQUENCE: 29

Ser Ile Tyr Thr Asp Ser Gly Asn Thr Trp
1               5                   10

<210> SEQ ID NO 30
<211> LENGTH: 4
<212> TYPE: PRT
<213> ORGANISM: Artificial Sequence
<220> FEATURE:
<223> OTHER INFORMATION: CDRH3

<400> SEQUENCE: 30

Asn Phe Ser Val
1

<210> SEQ ID NO 31
<211> LENGTH: 6
<212> TYPE: PRT
<213> ORGANISM: Artificial Sequence
<220> FEATURE:
<223> OTHER INFORMATION: CDRL1

<400> SEQUENCE: 31

Val Tyr Asn Ser Asp Arg
1               5

<210> SEQ ID NO 32
<211> LENGTH: 5
<212> TYPE: PRT
<213> ORGANISM: Artificial Sequence
<220> FEATURE:
<223> OTHER INFORMATION: CDRL2

<400> SEQUENCE: 32

Val Ser Lys Leu Ala
1               5

<210> SEQ ID NO 33
<211> LENGTH: 11
<212> TYPE: PRT
<213> ORGANISM: Artificial Sequence
<220> FEATURE:
```

<223> OTHER INFORMATION: CDRL3

<400> SEQUENCE: 33

Leu Gly Gly Tyr Asp Cys Ser Ser Ala Glu Cys
1               5                   10

<210> SEQ ID NO 34
<211> LENGTH: 17
<212> TYPE: PRT
<213> ORGANISM: Artificial Sequence
<220> FEATURE:
<223> OTHER INFORMATION: CDRH2

<400> SEQUENCE: 34

Ser Ile Tyr Thr Asp Ser Gly Asn Thr Trp Tyr Ala Ser Trp Val Lys
1               5                   10                  15

Gly

<210> SEQ ID NO 35
<211> LENGTH: 13
<212> TYPE: PRT
<213> ORGANISM: Artificial Sequence
<220> FEATURE:
<223> OTHER INFORMATION: CDRL1

<400> SEQUENCE: 35

Gln Ala Ser Gln Ser Val Tyr Asn Ser Asp Arg Leu Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CDRL2

<400> SEQUENCE: 36

Asp Val Ser Lys Leu Ala Ser
1               5

<210> SEQ ID NO 37
<211> LENGTH: 13
<212> TYPE: PRT
<213> ORGANISM: Artificial Sequence
<220> FEATURE:
<223> OTHER INFORMATION: CDRL3

<400> SEQUENCE: 37

Leu Gly Gly Tyr Asp Cys Ser Ser Ala Glu Cys Asn Val
1               5                   10

<210> SEQ ID NO 38
<211> LENGTH: 111
<212> TYPE: PRT
<213> ORGANISM: Artificial Sequence
<220> FEATURE:
<223> OTHER INFORMATION: heavy chain variable domain

<400> SEQUENCE: 38

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Arg Asp Thr
                20                  25                  30

Met Ile Trp Val Arg Gln Ala Pro Gly Glu Gly Leu Glu Trp Ile Gly
            35                  40                  45

-continued

Ser Ile Tyr Thr Asp Ser Gly Asn Thr Trp Tyr Ala Ser Trp Val Lys
       50                  55                  60

Gly Arg Phe Thr Ile Ser Lys Thr Ser Ser Thr Val Asp Leu Arg
65                  70                  75                  80

Ile Thr Ser Pro Thr Thr Glu Asp Thr Ala Tyr Phe Cys Ala Arg
                    85                  90                  95

Asn Phe Ser Val Trp Gly Pro Gly Thr Leu Val Thr Val Ser Leu
                100                 105                 110

<210> SEQ ID NO 39
<211> LENGTH: 112
<212> TYPE: PRT
<213> ORGANISM: Artificial Sequence
<220> FEATURE:
<223> OTHER INFORMATION: light chain variable domain

<400> SEQUENCE: 39

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Ser Asp
                20                  25                  30

Arg Leu Ala Trp Phe Gln Gln Met Arg Gly Gln Pro Pro Lys Leu Leu
            35                  40                  45

Ile Tyr Asp Val Ser Lys Leu Ala Ser Gly Val Pro Ser Arg Phe Ser
50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Asp Cys Ser
                85                  90                  95

Ser Ala Glu Cys Asn Val Phe Gly Gly Gly Thr Glu Val Val Val Lys
                100                 105                 110

<210> SEQ ID NO 40
<211> LENGTH: 140
<212> TYPE: PRT
<213> ORGANISM: Homo sapiens

<400> SEQUENCE: 40

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
            115                 120                 125

Ser Glu Glu Gly Tyr Gln Asp Tyr Glu Pro Glu Ala
            130                 135                 140

```
<210> SEQ ID NO 41
<211> LENGTH: 18
<212> TYPE: PRT
<213> ORGANISM: Artificial Sequence
<220> FEATURE:
<223> OTHER INFORMATION: linker peptide

<400> SEQUENCE: 41

Gly Gly Ser Gly Gly Gly Gly Ser Gly Gly Gly Gly Ser Gly Gly
1               5                   10                  15

Gly Ser

<210> SEQ ID NO 42
<211> LENGTH: 37
<212> TYPE: DNA
<213> ORGANISM: Artificial Sequence
<220> FEATURE:
<223> OTHER INFORMATION: rbHCfinal.up

<400> SEQUENCE: 42
aagcttgcca ccatggagac tgggctgcgc tggcttc                              37

<210> SEQ ID NO 43
<211> LENGTH: 21
<212> TYPE: DNA
<213> ORGANISM: Artificial Sequence
<220> FEATURE:
<223> OTHER INFORMATION: rbHCfinal.do

<400> SEQUENCE: 43
ccattggtga gggtgcccga g                                               21

<210> SEQ ID NO 44
<211> LENGTH: 34
<212> TYPE: DNA
<213> ORGANISM: Artificial Sequence
<220> FEATURE:
<223> OTHER INFORMATION: rbLCfinal.up

<400> SEQUENCE: 44
aagcttgcca ccatggacay gagggccccc actc                                 34

<210> SEQ ID NO 45
<211> LENGTH: 26
<212> TYPE: DNA
<213> ORGANISM: Artificial Sequence
<220> FEATURE:
<223> OTHER INFORMATION: rbLCfinal.do

<400> SEQUENCE: 45
cagagtrctg ctgaggttgt aggtac                                          26

<210> SEQ ID NO 46
<211> LENGTH: 324
<212> TYPE: PRT
<213> ORGANISM: Mus musculus

<400> SEQUENCE: 46

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45
```

```
Gly Val His Thr Phe Pro Ala Val Leu Gln Ser Asp Leu Tyr Thr Leu
 50                  55                  60
Ser Ser Ser Val Thr Val Pro Ser Ser Thr Trp Pro Ser Glu Thr Val
 65                  70                  75                  80
Thr Cys Asn Val Ala His Pro Ala Ser Ser Thr Lys Val Asp Lys Lys
                     85                  90                  95
Ile Val Pro Arg Asp Cys Gly Cys Lys Pro Cys Ile Cys Thr Val Pro
                100                 105                 110
Glu Val Ser Ser Val Phe Ile Phe Pro Pro Lys Pro Lys Asp Val Leu
                115                 120                 125
Thr Ile Thr Leu Thr Pro Lys Val Thr Cys Val Val Val Asp Ile Ser
130                 135                 140
Lys Asp Asp Pro Glu Val Gln Phe Ser Trp Phe Val Asp Asp Val Glu
145                 150                 155                 160
Val His Thr Ala Gln Thr Gln Pro Arg Glu Glu Gln Phe Asn Ser Thr
                165                 170                 175
Phe Arg Ser Val Ser Glu Leu Pro Ile Met His Gln Asp Trp Leu Asn
                180                 185                 190
Gly Lys Glu Phe Lys Cys Arg Val Asn Ser Ala Ala Phe Pro Ala Pro
                195                 200                 205
Ile Glu Lys Thr Ile Ser Lys Thr Lys Gly Arg Pro Lys Ala Pro Gln
210                 215                 220
Val Tyr Thr Ile Pro Pro Lys Glu Gln Met Ala Lys Asp Lys Val
225                 230                 235                 240
Ser Leu Thr Cys Met Ile Thr Asp Phe Phe Pro Glu Asp Ile Thr Val
                245                 250                 255
Glu Trp Gln Trp Asn Gly Gln Pro Ala Glu Asn Tyr Lys Asn Thr Gln
                260                 265                 270
Pro Ile Met Asp Thr Asp Gly Ser Tyr Phe Val Tyr Ser Lys Leu Asn
                275                 280                 285
Val Gln Lys Ser Asn Trp Glu Ala Gly Asn Thr Phe Thr Cys Ser Val
                290                 295                 300
Leu His Glu Gly Leu His Asn His His Thr Glu Lys Ser Leu Ser His
305                 310                 315                 320
Ser Pro Gly Lys

<210> SEQ ID NO 47
<211> LENGTH: 107
<212> TYPE: PRT
<213> ORGANISM: Mus musculus

<400> SEQUENCE: 47

Arg Ala Asp Ala Ala Pro Thr Val Ser Ile Phe Pro Pro Ser Ser Glu
 1                   5                  10                  15
Gln Leu Thr Ser Gly Gly Ala Ser Val Val Cys Phe Leu Asn Asn Phe
                 20                  25                  30
Tyr Pro Lys Asp Ile Asn Val Lys Trp Lys Ile Asp Gly Ser Glu Arg
                 35                  40                  45
Gln Asn Gly Val Leu Asn Ser Trp Thr Asp Gln Asp Ser Lys Asp Ser
 50                  55                  60
Thr Tyr Ser Met Ser Ser Thr Leu Thr Leu Thr Lys Asp Glu Tyr Glu
 65                  70                  75                  80
Arg His Asn Ser Tyr Thr Cys Glu Ala Thr His Lys Thr Ser Thr Ser
                 85                  90                  95
```

```
Pro Ile Val Lys Ser Phe Asn Arg Asn Glu Cys
            100                 105

<210> SEQ ID NO 48
<211> LENGTH: 106
<212> TYPE: PRT
<213> ORGANISM: Mus musculus

<400> SEQUENCE: 48

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 49
<211> LENGTH: 330
<212> TYPE: PRT
<213> ORGANISM: Homo sapiens

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 50
<211> LENGTH: 330
<212> TYPE: PRT
<213> ORGANISM: Artificial Sequence
<220> FEATURE:
<223> OTHER INFORMATION: human Ig1 hole constant region

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240
```

Leu Thr Lys Asn Gln Val Ser Leu Trp Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 51
<211> LENGTH: 330
<212> TYPE: PRT
<213> ORGANISM: Artificial Sequence
<220> FEATURE:
<223> OTHER INFORMATION: human Ig1 knob constant region

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

-continued

```
Asn Tyr Lys Thr Thr Pro Pro Val Leu Asp Ser Asp Gly Ser Phe Phe
            275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 52
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 52

Ile Gly Gln Asn Met Val Thr Ile Val Gln Ser Asn Gly Asn Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 53

Asn Met Val Thr Ile Val Gln Ser Asn Gly Asn Leu Asp Pro Val
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: human transferrin receptor fragment

<400> SEQUENCE: 54

Gln Ser Asn Gly Asn Leu Asp Pro Val Glu Ser Pro Glu Gly Tyr
1               5                   10                  15

<210> SEQ ID NO 55
<211> LENGTH: 32
<212> TYPE: PRT
<213> ORGANISM: Artificial Sequence
<220> FEATURE:
<223> OTHER INFORMATION: peptidic linker

<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

<210> SEQ ID NO 56
<211> LENGTH: 118
<212> TYPE: PRT
<213> ORGANISM: Mus musculus

<400> SEQUENCE: 56

Glu Val Gln Leu Val Glu Ser Gly Gly Gly Leu Val Gln Pro Gly Asn
1               5                   10                  15
```

```
Ser Leu Thr Leu Ser Cys Val Ala Ser Gly Phe Thr Phe Ser Asn Tyr
            20                  25                  30

Gly Met His Trp Ile Arg Gln Ala Pro Lys Lys Gly Leu Glu Trp Ile
            35                  40                  45

Ala Met Ile Tyr Tyr Asp Ser Ser Lys Met Asn Tyr Ala Asp Thr Val
50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Val Pro Thr Ser His Tyr Val Val Asp Val Trp Gly Gln Gly Val
            100                 105                 110

Ser Val Thr Val Ser Ser
            115

<210> SEQ ID NO 57
<211> LENGTH: 107
<212> TYPE: PRT
<213> ORGANISM: Mus musculus

<400> SEQUENCE: 57

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
            35                  40                  45

Tyr Gly Ala Thr Ser Leu Ala Asp Gly Val Pro Ser Arg Phe Ser Gly
        50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95

Thr Phe Gly Gly Gly Thr Lys Leu Glu Leu Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: L104V and L106I variant of SEQ ID NO: 57

<400> SEQUENCE: 58

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ala Trp Tyr Gln Gln Lys Pro Gly Lys Ser Pro Gln Leu Leu Ile
            35                  40                  45

Tyr Gly Ala Thr Ser Leu Ala Asp Gly Val Pro Ser Arg Phe Ser Gly
        50                  55                  60

Ser Arg Ser Gly Thr Gln Phe Ser Leu Lys Ile Ser Arg Val Gln Val
65                  70                  75                  80

Glu Asp Ile Gly Ile Tyr Tyr Cys Leu Gln Ala Tyr Asn Thr Pro Trp
                85                  90                  95
```

```
Thr Phe Gly Gly Gly Thr Lys Val Glu Ile Lys
            100                 105
```